US011286283B2

(12) United States Patent
Braun et al.

(10) Patent No.: US 11,286,283 B2
(45) Date of Patent: Mar. 29, 2022

(54) IMMUNOGENIC COMPOSITION

(71) Applicant: GLAXOSMITHKLINE BIOLOGICALS SA, Rixensart (BE)

(72) Inventors: Martin Braun, Schlieren (CH); Amirreza Faridmoayer, Schlieren (CH); Sabina Marietta Gerber, Schlieren (CH); Markus Mueller, Schlieren (CH)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 16/954,306

(22) PCT Filed: Dec. 19, 2018

(86) PCT No.: PCT/EP2018/085854

§ 371 (c)(1),
(2) Date: Jun. 16, 2020

(87) PCT Pub. No.: WO2019/121924

PCT Pub. Date: Jun. 27, 2019

(65) Prior Publication Data

US 2021/0214402 A1 Jul. 15, 2021

(30) Foreign Application Priority Data

Dec. 21, 2017 (GB) ..................................... 1721576

(51) Int. Cl.

| | |
|---|---|
| ***C07K 1/00*** | (2006.01) |
| ***C07K 14/31*** | (2006.01) |
| ***A61K 47/64*** | (2017.01) |
| ***A61K 39/085*** | (2006.01) |
| ***C12N 9/10*** | (2006.01) |
| *A61K 38/00* | (2006.01) |

(52) U.S. Cl.
CPC ............ *C07K 14/31* (2013.01); *A61K 39/085* (2013.01); *A61K 47/6425* (2017.08); *C12N 9/1051* (2013.01); *A61K 38/00* (2013.01)

(58) Field of Classification Search
CPC ..................................................... C07K 14/31
See application file for complete search history.

(56) References Cited

FOREIGN PATENT DOCUMENTS

| | | | |
|---|---|---|---|
| WO | 2010119343 | A2 | 10/2010 |
| WO | 2015048332 | A2 | 4/2015 |

OTHER PUBLICATIONS

International Search Report and Written Opinion in corresponding International Application No. PCT/EP2018/085854 dated Apr. 18, 2019 (10 pages).
Adhikari et al., PLoS ONE, vol. 7, issue 6: 1-11 (2012).
Adhikari et al., Vaccine, vol. 34, issue 50: 6402-6407 (2016).

*Primary Examiner* — Albert M Navarro

(57) ABSTRACT

The present invention discloses modified *Staphylococcus aureus* HIa proteins which show reduced tendency to aggregate, improving protein stability and yield. Said modified HIa proteins optionally also contain glycosylation site consensus sequences. The invention also discloses a conjugate comprising a modified HIa protein and an antigen (for example a *Staphylococcus aureus* saccharide antigen), wherein the antigen is linked to an amino acid residue of the modified HIa protein.

20 Claims, 14 Drawing Sheets

Specification includes a Sequence Listing.

A

IMMUNOGENIC COMPOSITION

SEQUENCE LISTING

The instant application contains a Sequence Listing which has been submitted electronically in ASCII format and is hereby incorporated by reference in its entirety. Said ASCII copy, created on Apr. 1, 2021, is named VB66307 _SL.txt and is 45,406 bytes in size.

TECHNICAL FIELD

The present invention relates to the field of immunogenic compositions and vaccines, their manufacture and the use of such compositions in medicine. More particularly, it relates to a modified HIa protein from *Staphylococcus aureus* and its use as a vaccine antigen. The modified HIa can be used as an antigen in its own right and also as a carrier protein for other antigens, particularly saccharide antigens.

BACKGROUND

*Staphylococcus aureus* is a major cause of invasive human infections, including bacteremia, endocarditis, pneumonia, and wound infections. *S. aureus* develops antibiotic resistance very rapidly, and strains have emerged which are resistant to commonly used antibiotics such as methicillin and even the antibiotic of last resort, vancomycin. Methicillin-resistant *S. aureus* (MRSA) is endemic in hospitals, and community-associated MRSA strains are spreading worldwide, posing a major global challenge.

There is thus an urgent need for a vaccine to prevent staphylococcal disease. Several vaccines have been tested in clinical trials, including capsular polysaccharide (CPS) conjugates, individual protein antigens, and monoclonal antibodies (mAbs) to lipoteichoic acid. However, all have failed at various developmental stages, and to date there is no vaccine against *S. aureus* on the market.

*S. aureus* vaccines that elicit both humoral and cell mediated immune responses are currently under evaluation, and both protein antigens such as alpha toxin (HIa) and CPS are key antigens under consideration for inclusion in a multi-component vaccine. 90% of *S. aureus* strains express either Type 5 or Type 8 capsular polysaccharide, so a vaccine comprising CP5 and CP8 could potentially protect against the majority of circulating *S. aureus* strains. Vaccines comprising *S. aureus* capsular polysaccharides have been used to generate a protective immune response against staphylococci, but vaccines comprising CPS alone have not proved fully effective. A vaccine containing conjugates of *S. aureus* Type 5 and Type 8 capsular polysaccharides conjugated to *Pseudomonas* exoprotein A (StaphVAX—Nabi Biopharmaceuticals) has been tested in clinical trials, where it demonstrated safety and efficacy in PhI and II but failed to achieve the required endpoint in PhIII, as described in WO 03/61558.

Vaccines comprising *S. aureus* CPS conjugated to *Pseudomonas aeruginosa* exoprotein A (EPA) or *S. aureus* HIa using a novel glycoengineering technology have been tested in rabbits and mice (Wacker et al, 2014, Journal of Infectious Diseases 209: 1551-61). The CP-HIa bioconjugate vaccine protected mice against bacteraemia and lethal pneumonia, demonstrating that bioconjugates of *S. aureus* proteins and capsular polysaccharides may be a promising candidate for an effective vaccine against *S. aureus.*

HIa is a toxin, and thus needs to be detoxified in order to be used as a vaccine antigen. Monomers of wild-type HIa assemble to form a hexamer which creates a lipid-bilayer penetrating pore in the membrane of human erythrocytes and other cells, resulting in cell lysis. The cell lytic activity of HIa may be reduced by mutation of amino acid residues involved in pore formation, as described in Menzies and Kernodle (Menzies and Kernodle, 1994, Infect Immun 62, 1843-1847). One such mutant (HIaH35L) showed greatly reduced hexamer formation, had no haemolytic activity and was non-toxic to mice. HIaH35L has since been used in experimental vaccines against *S. aureus* infection, including the bioconjugate vaccine described above.

However, the inventors have found that, in addition to hexamers, HIa also forms higher-level aggregates that affect protein stability and yield. Mutants displaying reduced hexamer formation, such as HIaH35L, are still affected by the problem of aggregate formation. There is thus a need for stable HIa proteins that show reduced aggregation and may be produced with higher yield than the currently known detoxified mutants.

SUMMARY OF THE INVENTION

The present invention provides a modified HIa (Staphylococcal haemolysin A, also known as alpha toxin) protein and conjugates of said modified HIa (including bioconjugates).

Accordingly, there is provided in one aspect of the present invention, a modified HIa protein comprising an amino acid sequence of SEQ ID NO. 1 or an amino acid sequence at least 80%, 85%, 90%, 92%, 95%, 96%, 97%, 98% or 99% identical to SEQ ID NO. 1, modified in that the amino acid sequence comprises amino acid substitutions at positions H48 and G122 of SEQ ID NO. 1 or at equivalent positions within an amino acid sequence at least 80%, 85%, 90%, 92%, 95%, 96%, 97%, 98% or 99% identical to SEQ ID NO. 1, wherein said substitutions are respectively H to C and G to C (e.g. SEQ ID NO: 2).

Said modified HIa protein may be further modified in that the amino acid sequence comprises an amino acid substitution at position H35 (e.g. H35L) of SEQ ID NO. 1 or at an equivalent position within an amino acid sequence at least 80%, 85%, 90%, 92%, 95%, 96%, 97%, 98% or 99% identical to SEQ ID NO. 1 (e.g. SEQ ID NO: 3).

Said modified HIa protein may be further modified to comprise one or more consensus sequence(s) selected from: D/E-X-N-Z-S/T (SEQ ID NO. 11) and K-D/E-X-N-Z-S/T-K (SEQ ID NO. 12), wherein X and Z are independently any amino acid apart from proline (e.g. SEQ ID NO: 7). In an embodiment, said modified HIa protein contains the following mutations: H35L, H48C and G122C. Accordingly, there is provided a modified HIa protein comprising an amino acid sequence of SEQ ID NO. 3 or an amino acid sequence at least 80%, 85%, 90%, 92%, 95%, 96%, 97%, 98% or 99% identical to SEQ ID NO. 3, modified in that the amino acid sequence comprises one or more consensus sequence(s) selected from: D/E-X-N-Z-S/T (SEQ ID NO. 11) and K-D/E-X-N-Z-S/T-K (SEQ ID NO. 12), wherein X and Z are independently any amino acid apart from proline. An exemplary sequence is that of SEQ ID NO: 7.

According to a further aspect of the invention, there is provided a conjugate (e.g. bioconjugate) comprising a oligosaccharide or polysaccharide antigen linked, e.g. covalently linked, to a modified HIa protein of the invention.

According to a further aspect of the invention, there is provided a polynucleotide encoding a modified HIa protein or bioconjugate of the invention.

According to a further aspect of the invention, there is provided a vector comprising a polynucleotide encoding a modified HIa protein or bioconjugate of the invention.

According to a further aspect of the invention, there is provided a host cell comprising:

i) one or more nucleic acids that encode glycosyltransferase(s);

ii) a nucleic acid that encodes an oligosaccharyl transferase;

iii) a nucleic acid that encodes a modified HIa protein of the invention; and optionally iv) a nucleic acid that encodes a polymerase (e.g. wzy).

According to a further aspect of the invention, there is provided a process for producing a bioconjugate that comprises (or consists of) a modified HIa protein linked to a saccharide, said method comprising: (i) culturing a host cell of the invention under conditions suitable for the production of proteins and (ii) isolating the bioconjugate produced by said host cell.

According to a further aspect of the invention, there is provided a bioconjugate produced by a process of the invention, wherein said bioconjugate comprises a saccharide linked to a modified HIa protein.

According to a further aspect of the invention, there is provided an immunogenic composition comprising the modified HIa protein of the invention, or a conjugate of the invention, or a bioconjugate of the invention and a pharmaceutically acceptable excipient or carrier.

According to a further aspect of the invention, there is provided a method of making a immunogenic composition of the invention comprising the step of mixing the modified HIa protein or the conjugate or the bioconjugate with a pharmaceutically acceptable excipient or carrier.

According to a further aspect of the invention, there is provided a method for the treatment or prevention of staphylococcal infection, in particular *Staphylococcus aureus* infection, in a subject in need thereof comprising administering to said subject a therapeutically effective amount of a modified HIa protein of the invention, or a conjugate of the invention, or a bioconjugate of the invention.

According to a further aspect of the invention, there is provided a method of immunising a human host against staphylococcal infection, in particular *Staphylococcus aureus* infection, comprising administering to the host an immunoprotective dose of a modified HIa protein of the invention, or a conjugate of the invention, or a bioconjugate of the invention.

According to a further aspect of the invention, there is provided a method of inducing an immune response to *staphylococcus*, in particular *Staphylococcus aureus*, in a subject, the method comprising administering a therapeutically or prophylactically effective amount of a modified HIa protein of the invention, or a conjugate of the invention, or a bioconjugate of the invention.

According to a further aspect of the invention, there is provided a modified HIa protein of the invention, or a conjugate of the invention, or a bioconjugate of the invention for use in the treatment or prevention of a disease caused by staphylococcal infection, in particular *Staphylococcus aureus* infection.

According to a further aspect of the invention, there is provided a modified HIa protein of the invention, or a conjugate of the invention, or a bioconjugate of the invention in the manufacture of a medicament for the treatment or prevention of a disease caused by staphylococcal infection, in particular *Staphylococcus aureus* infection.

DESCRIPTION OF FIGURES

FIG. 1 represents the 3D crystal structures of A) the toxic pore-forming HIa heptamer (PDB identifier 7AHL, Song et al., 1996), B) the non-toxic HIa monomer (PDB identifier 4IDJ, Foletti et al., 2013) and C) the superposition of one monomer in A) high-lighted in red/pale grey and the monomer in B) high-lighted in blue/dark grey. The broader region of the cysteine-cysteine cross-linking positions is indicated by an oval.

FIG. 3 shows the enhanced stability (reduced aggregate formation) and productivity of cross-linked HIa variants for CP5-HIa bioconjugate production. All HIa variants included the glycosite at position 131 (substituted for K131). Key: M=protein Marker; C=non-cross-linked variant; SS1=Y102C-G126C; SS2=G122C-H48C; SS3=N121C-H48C SS4=G122C-L52C; B=samples were boiled prior to loading; NB=samples were not boiled prior to loading.

Lane 1: PageRuler Pre-stained Protein Marker

Lane 2: Protein samples from StGVXN1717[pGVXN393 (cap5HIJK), pGVXN570 ($HIa_{H35L}$), pGVXN1221 ($pgIB_{cuo\ N311V\text{-}K482R\text{-}D483H\text{-}A669V}$)], sample was produced in the presence of PgIB and boiled.

Lane 3: Protein samples from StGVXN1717[pGVXN393 (cap5HIJK), pGVXN570 ($HIa_{H35L}$), pGVXN1221 ($pgIB_{cuo\ N311V\text{-}K482R\text{-}D483H\text{-}A669V}$)], sample was produced in the presence of PgIB and not boiled Lane 4: Protein samples from StGVXN1717[pGVXN393 (cap5HIJK), pGVXN570 ($HIa_{H35L}$), pGVXN72 (empty PgIB plasmid vector)], sample was produced in the absence of PgIB and boiled Lane 5: Protein samples from StGVXN1717[pGVXN393 (cap5HIJK), pGVXN570 ($HIa_{H35L}$), pGVXN72 (empty PgIB plasmid vector)], sample was produced in the absence of PgIB and not boiled Lane 6: empty Lane 7: Protein samples from StGVXN1717[pGVXN393 (cap5HIJK), pGVXN2178 ($HIa_{H35L\text{-}Y102C\text{-}G126C}$), pGVXN1221 ($pgIB_{cuo\ N311V\text{-}K482R\text{-}D483H\text{-}A669V}$)], sample was produced in the presence of PgIB and boiled Lane 8: Protein samples from StGVXN1717[pGVXN393 (cap5HIJK), pGVXN2178 ($HIa_{H35L\text{-}Y102C\text{-}G126C}$), pGVXN1221 ($pgIB_{cuo\ N311V\text{-}K482R\text{-}D483H\text{-}A669V}$)], sample was produced in the presence of PgIB and not boiled Lane 9: Protein samples from StGVXN1717[pGVXN393 (cap5HIJK), pGVXN2179 ($HIa_{H35L-H48C-G122C}$), pGVXN1221 ($pgIB_{cuo\ N311V-K482R-D483H-A669V}$)], sample was produced in the presence of PgIB and boiled Lane 10: Protein samples from StGVXN1717 [pGVXN393 (cap5HIJK), pGVXN2179 ($HIa_{H35L-G122C-H48C}$), pGVXN1221 ($pgIB_{cuo\ N311V-K482R-D483H-A669V}$)], sample was produced in the presence of PgIB and not boiled Lane 11: Protein samples from StGVXN1717 [pGVXN393 (cap5HIJK), pGVXN2180 ($HIa_{H35L-H48C-N121C}$), pGVXN1221 ($pgIB_{cuo\ N311V-K482R-D483H-A669V}$)], sample was produced in the presence of PgIB and boiled Lane 12: Protein samples from StGVXN1717 [pGVXN393 (cap5HIJK), pGVXN2180 ($HIa_{H35L-H48C-N121C}$), pGVXN1221 ($pgIB_{cuo\ N311V-K482R-D483H-A669V}$)], sample was produced in the presence of PgIB and not boiled Lane 13: Protein samples from StGVXN1717 [pGVXN393 (cap5HIJK), pGVXN2181 (HIa H35L-L52C-G122C), pGVXN1221 ($pgIB_{cuo\ N311V-K482R-D483H-A669V}$)], sample was produced in the presence of PgIB and boiled Lane 14: Protein samples from StGVXN1717 [pGVXN393 (cap5HIJK), pGVXN2181 (HIa H35L-L52C-G122C), pGVXN1221 ($pgIB_{cuo\ N311V-K482R-D483H-A669V}$)], sample was produced in the presence of PgIB and not boiled.

Figure 4A:
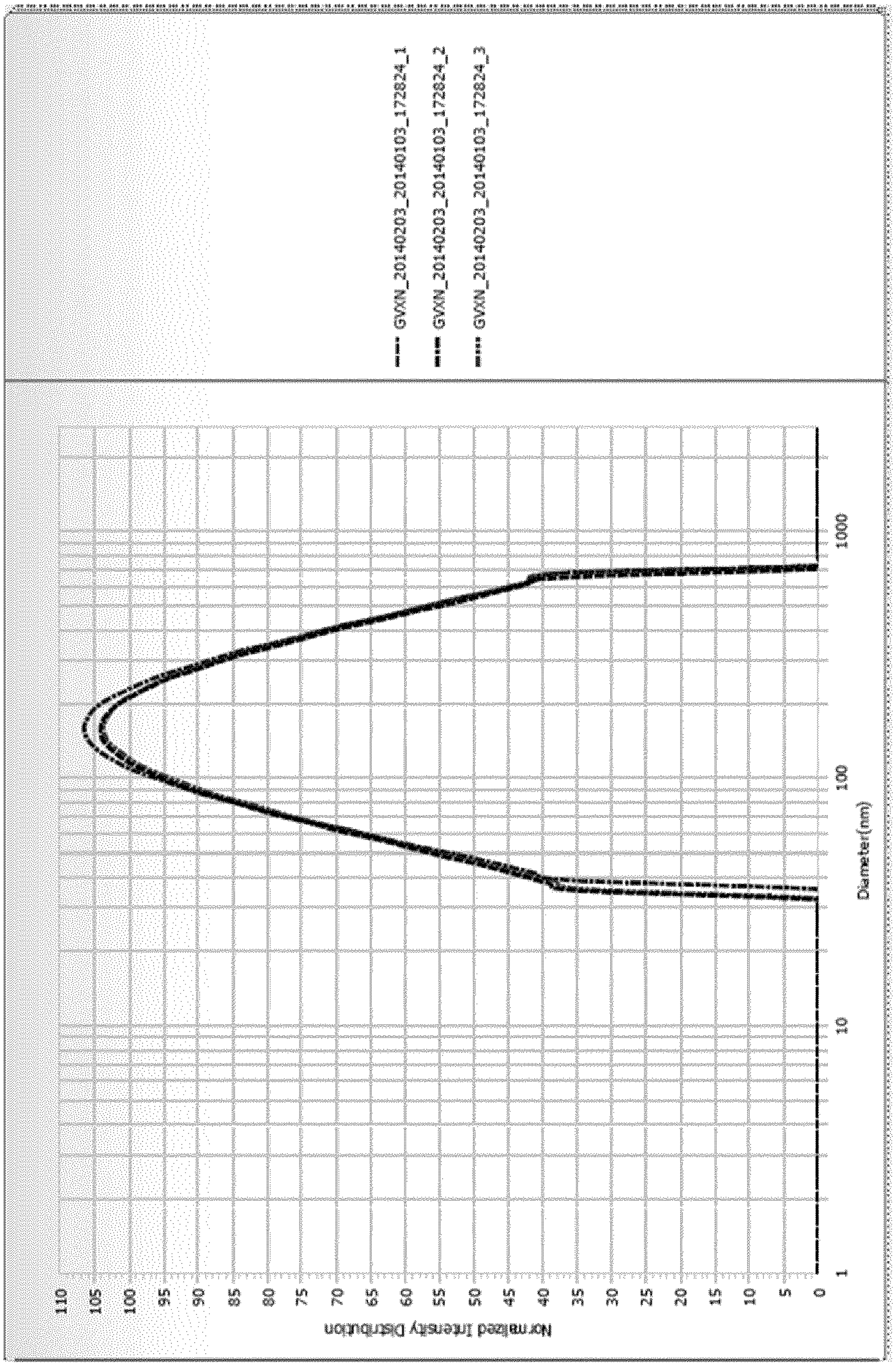
Figure 4B:
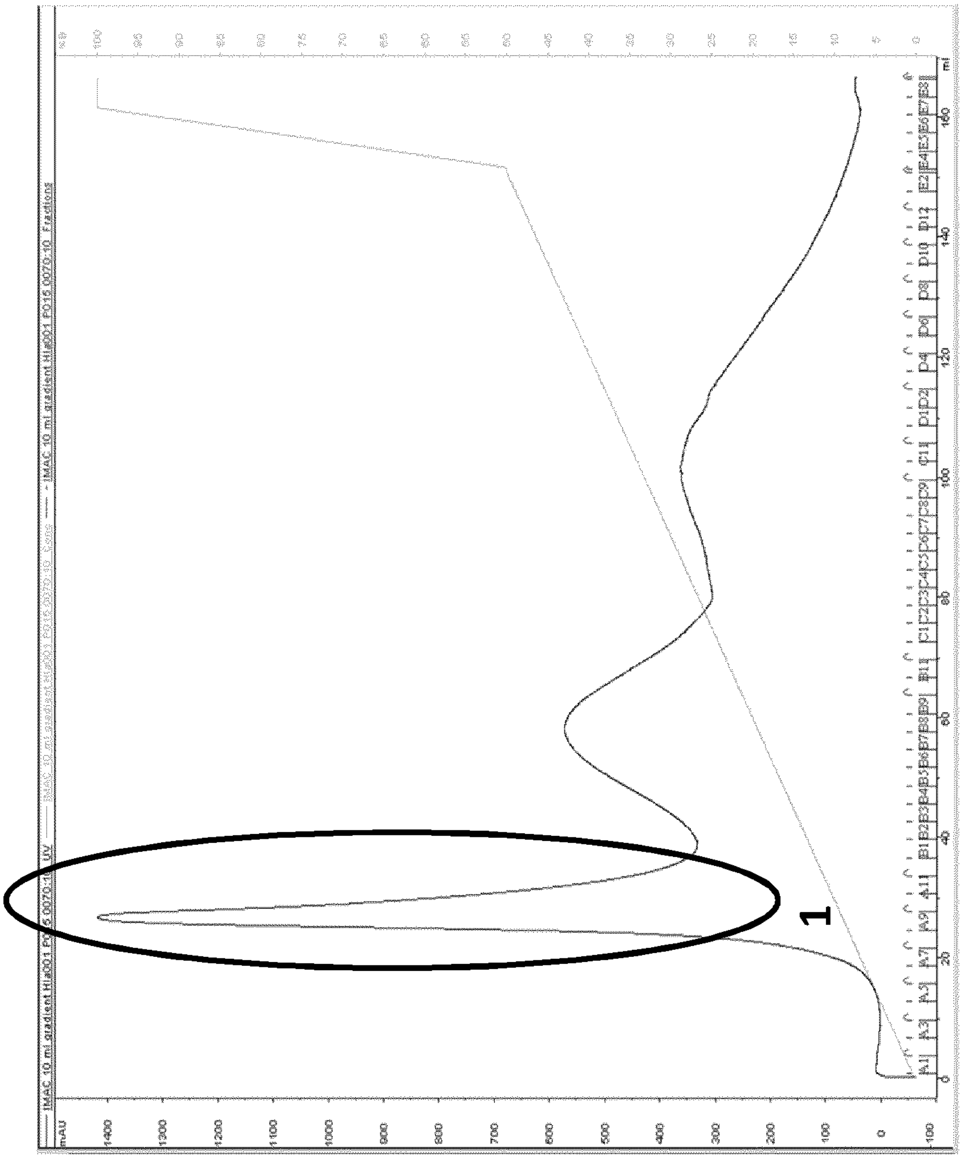

FIG. 4: Analysis of aggregated u-HIa species by Dynamic Light Scattering (DLS)

FIG. 4 shows the analysis of aggregated u-HIa (unconjugated HIa) species by Dynamic Light Scattering (DLS). A) shows the average size distribution profile of an aggregated HIa (3 samples). B) shows the aggregated u-HIa species used for the analysis, peak one from an IMAC eluting at approximately 90 mM imidazole (indicated by oval). C) shows measurements done in program Pymol to estimate the rough maximal dimensions of either the monomeric or heptameric molecule in nanometers. The longest dimension in the monomer is maximal 8 nanometer. The heptameric form has a maximal dimension of approximately 10 nanometer in all directions.

Figure 5A:
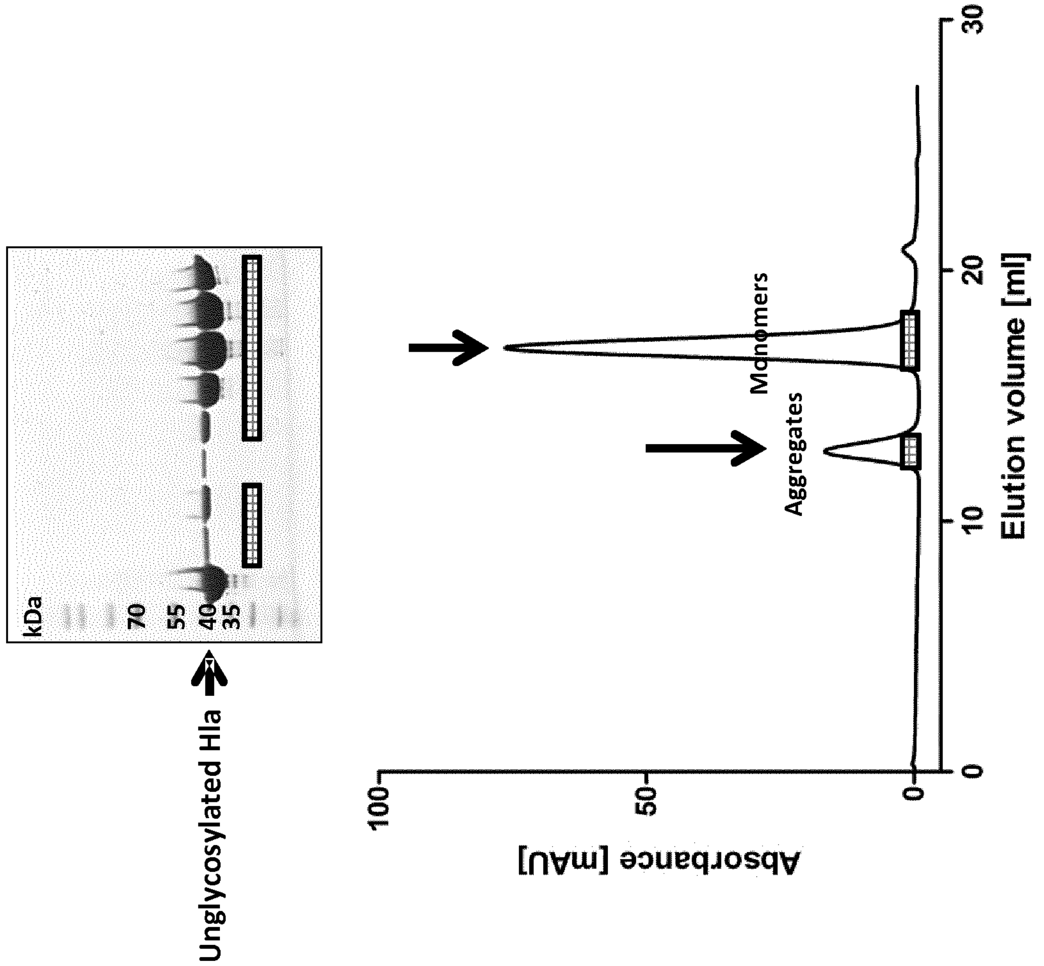
Figure 5B:
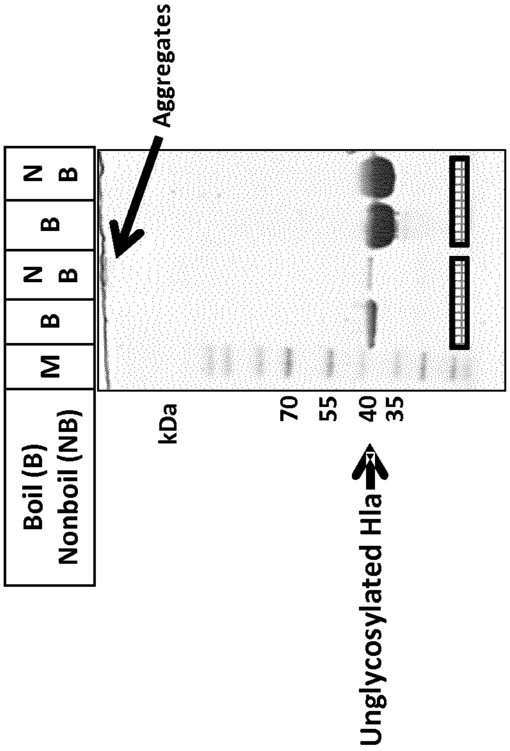

FIG. 5: Correlation of non-cross-linked, unglycosylated (u-HIa) aggregate migration behavior from non-boiled sample in SDS-PAGE with aggregate species detected by size exclusion chromatography FIG. 5 shows the correlation of aggregated unglycosylated, non-crosslinked HIa running as large species (A) in size exclusion chromatography (absorbance readout from chromatography column and SDS-PAGE of elution fractions) and (B) correspondingly as higher apparent molecular weight in SDS-PAGE when the sample is non-boiled (lane 4).

Figure 6:
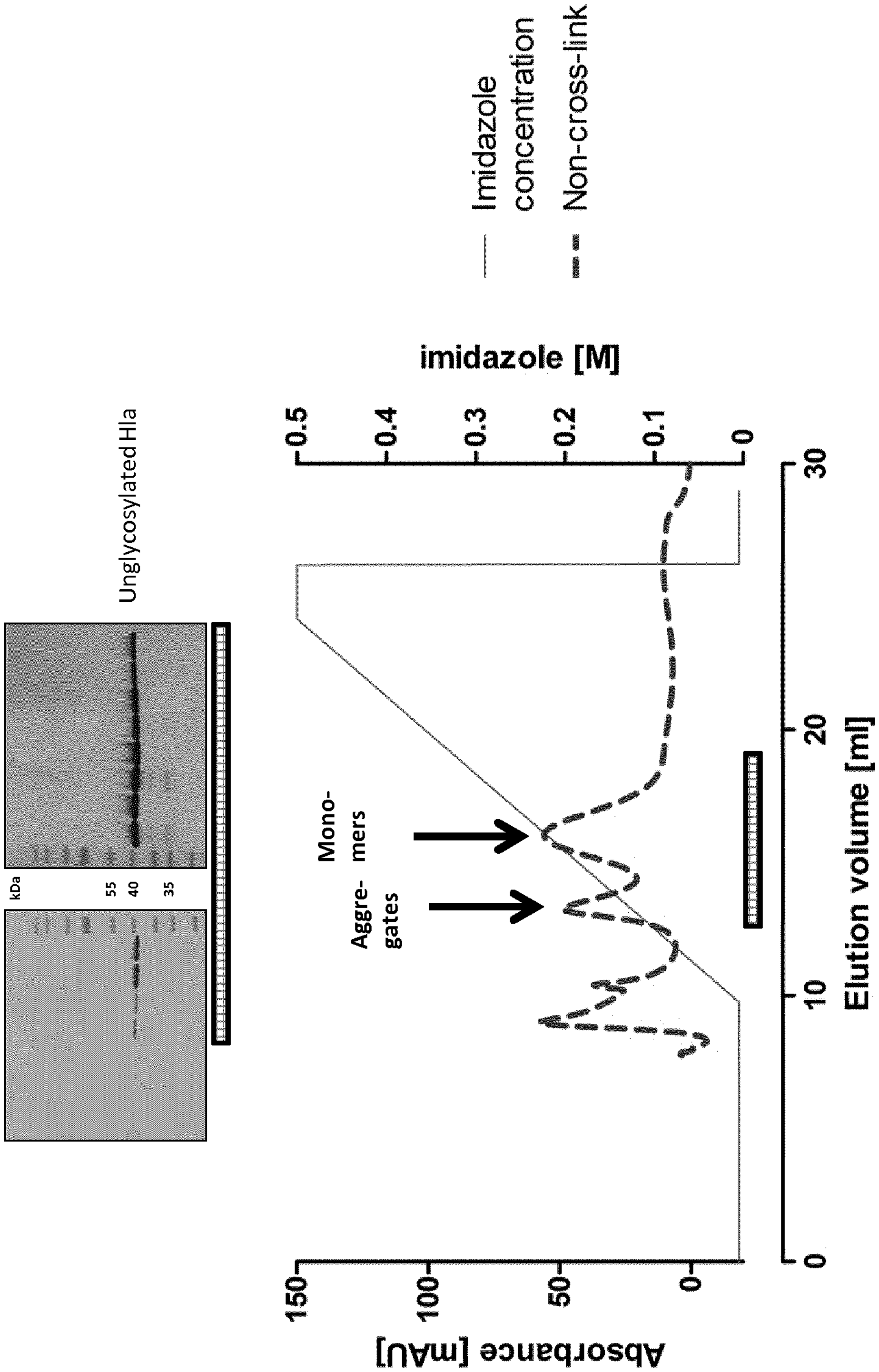

FIG. 6: Elution profiles of non-cross-linked unglycosylated HIa variants from Immobilized metal affinity chromatography (IMAC)

FIG. 6 shows an elution profile of an immobilized metal affinity chromatography (IMAC) of unglycosylated, non-cross-linked HIa with the immunoblot analysis of the respective elution fractions with an anti-His antibody.

Figure 7:
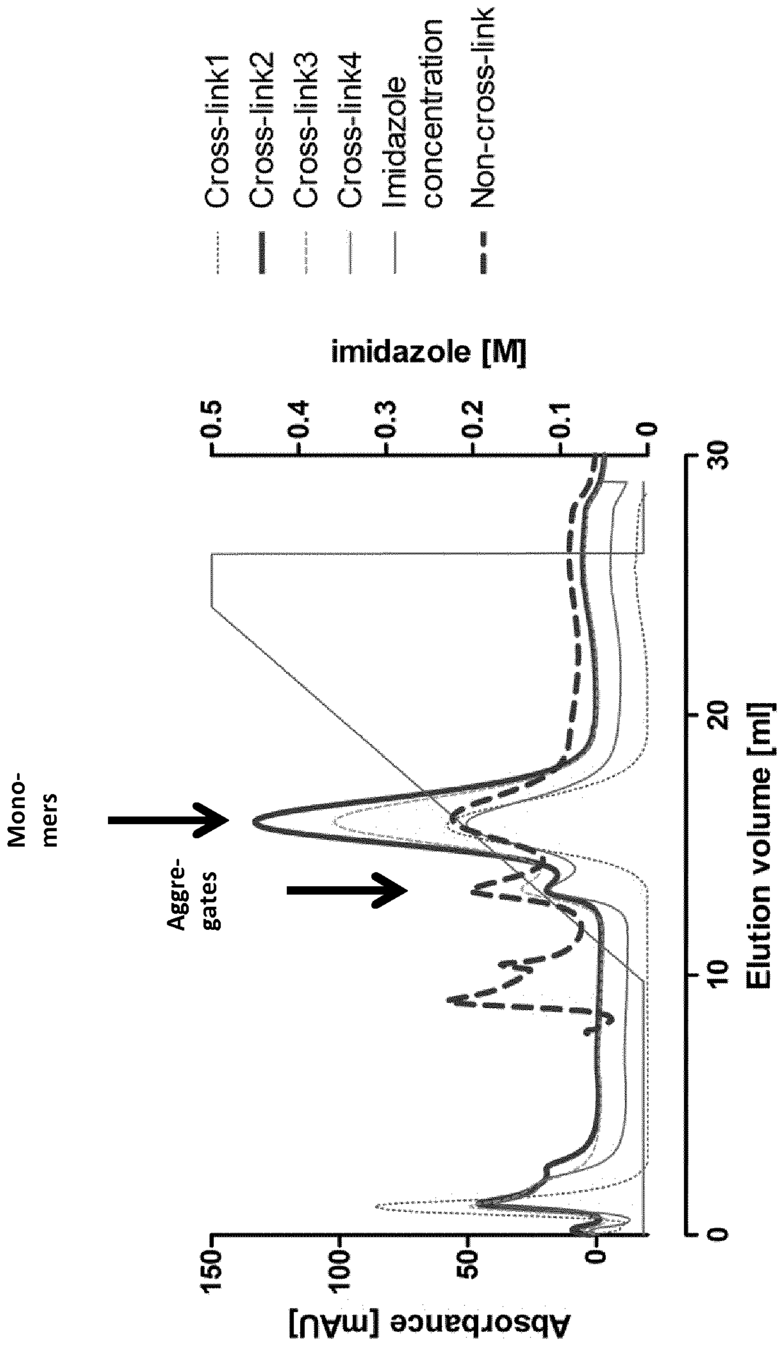

FIG. 7: Elution profiles of non-cross-linked versus cross-linked unglycosylated Hemolysin A variants from Immobilized metal affinity chromatography (IMAC)

FIG. 7 shows the overlay of an immobilized metal affinity chromatography (IMAC) elution profile from unglycosylated, non-cross-linked HIa from FIG. 6 and of the four unglycosylated, cross-linked HIa variants showing prevention (Y102C/G126C) or strongly reduced formation of aggregate relative to monomer, associated with increased protein yield (G122C/H48C). Y102-G126=Cross-Link1, G122-H48=Cross-Link 2, N121-H48=Cross-Link 3, G122-L52=Cross-Link 4.

Figure 8:
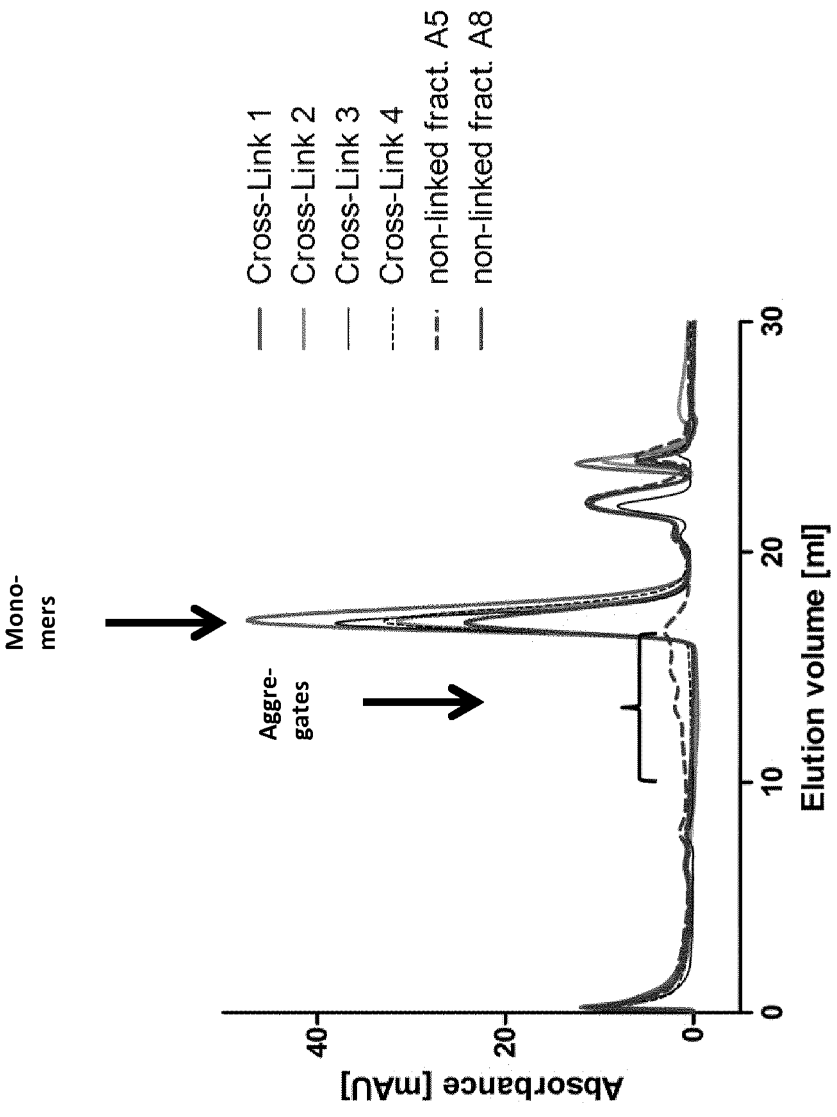

FIG. 8: Elution profiles of non-cross-linked versus cross-linked unglycosylated Hemolysin A variants from Size exclusion chromatography (SEC)

FIG. 8 shows a size exclusion chromatography analysis of the unglycosylated, non-cross-linked HIa variant eluted as aggregates or monomers obtained from the IMAC gradient elution shown in FIG. 6 and the IMAC eluates from the monomeric species of the four cross-linked HIa variants shown in FIG. 7.

Figure 9:
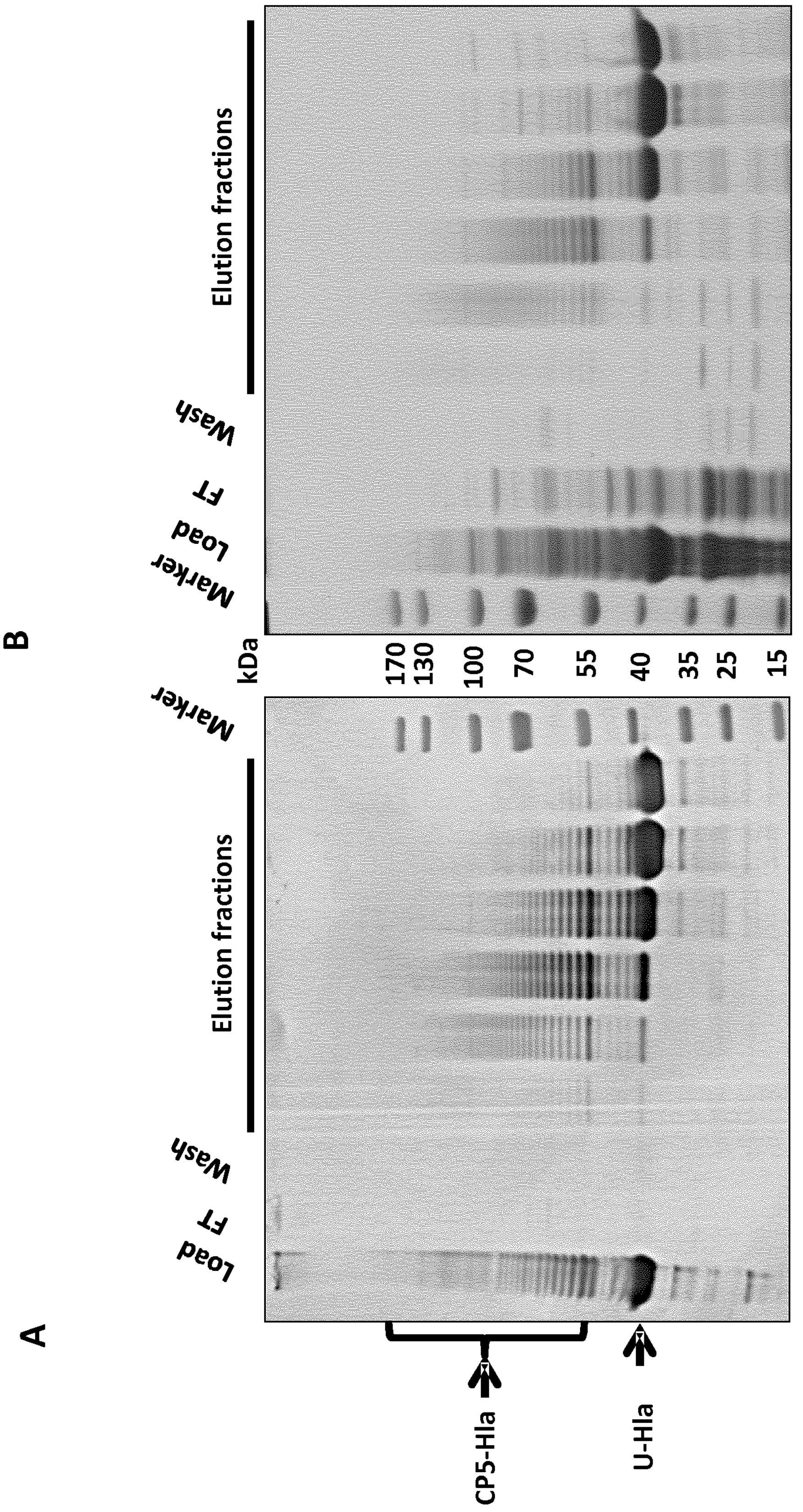

FIG. 9: Highly selective purification of CP5-HIa carrying a C-terminal tag using cationic exchange chromatography Proteins from the elution fractions described in Example 6 were separated by a 4-12% SDS-PAGE and blotted onto a nitrocellulose membrane and detected by an anti-HIa antibody or the gel was directly stained with SimplyBlue Safe Stain.

A: 40 microlitre loaded

Lane 1: Protein sample from the sample prior to loading onto the column

Lane 2: Protein samples from pooled flow-through fractions

Lane 3: Protein samples from pooled wash fractions

Lane 4-9: Protein samples from elution fractions

Lane 10: PageRuler Prestained Protein Marker

B: 20 microlitre loaded

Lane 1: PageRuler Prestained Protein Marker

Lane 2: Protein sample from the sample prior to loading onto the column

Lane 3: Protein samples from pooled flow-through fractions

Lane 4: Protein samples from pooled wash fractions

Lane 5-10: Protein samples from elution fractions

Figure 10:
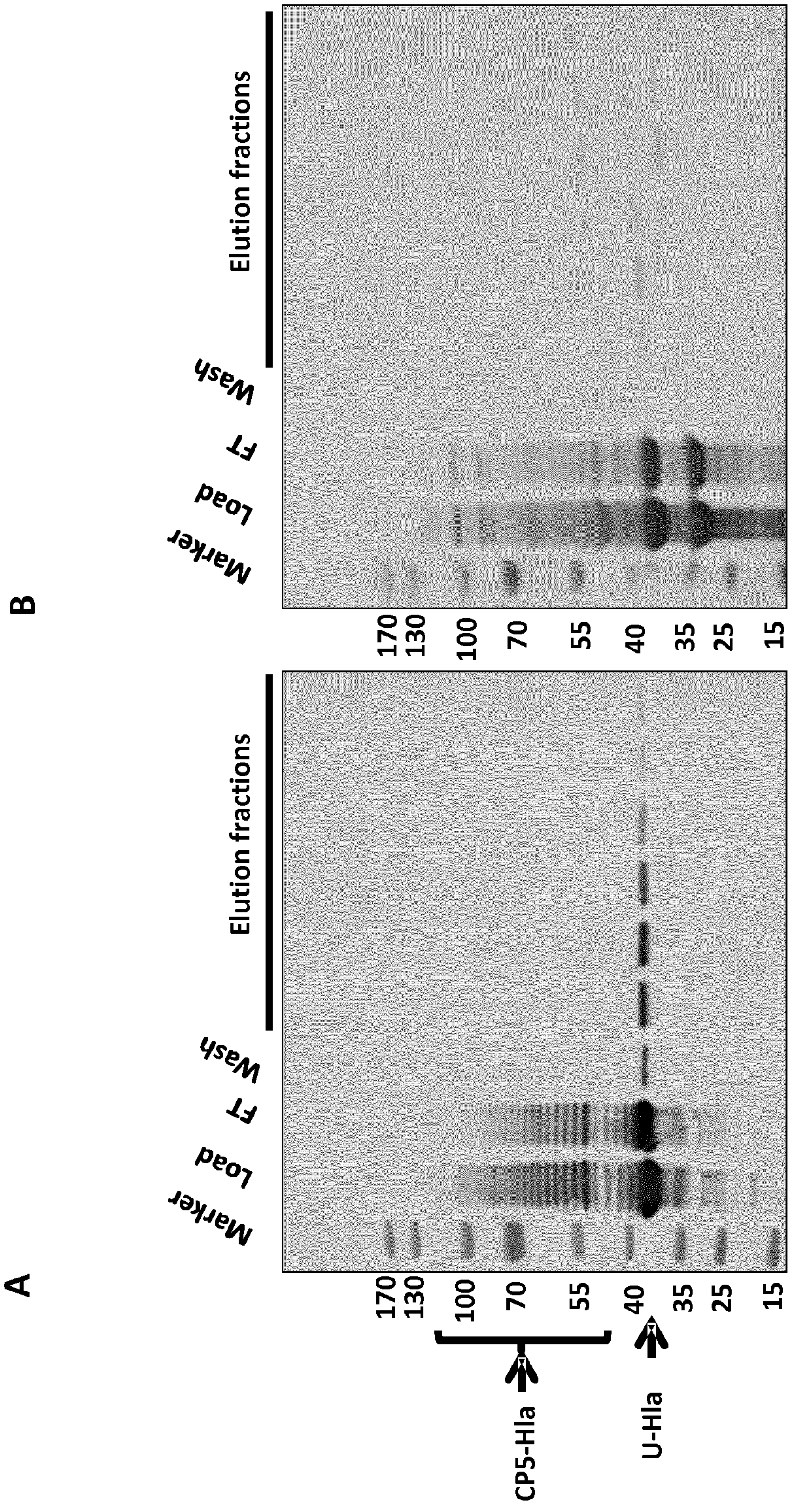

FIG. 10: Purification fractions of cation exchange chromatography of non-tagged CP5-HIa bioconjugate.

The same procedure as for FIG. 9 was carried out using non-tagged CP5-HIa.

Gel A: 20 microliter loaded

Lane 1: PageRuler Prestained Protein Marker

Lane 2: Protein sample from the sample prior to loading onto the column

Lane 3: Protein samples from pooled flow-through fractions

Lane 4: Protein samples from pooled wash fractions

Lane 5-10: Protein samples from elution fractions

Gel B: 40 microliter loaded

Lane 1: PageRuler Prestained Protein Marker

Lane 2: Protein sample from the sample prior to loading onto the column

Lane 3: Protein samples from pooled flow-through fractions

Lane 4: Protein samples from pooled wash fractions

Lane 5-10: Protein samples from elution fractions

DETAILED DESCRIPTION

Terminology

Carrier protein: a protein covalently attached to an antigen (e.g. saccharide antigen) to create a conjugate (e.g. bioconjugate). A carrier protein activates T-cell mediated immunity in relation to the antigen to which it is conjugated.

Any amino acid apart from proline (pro, P): refers to an amino acid selected from the group consisting of alanine (ala, A), arginine (arg, R), asparagine (asn, N), aspartic acid (asp, D), cysteine (cys, C), glutamine (gin, Q), glutamic acid (glu, E), glycine (gly, G), histidine (his, H), isoleucine (ile, I), leucine (leu, L), lysine (lys, K), methionine (met, M), phenylalanine (phe, F), serine (ser, S), threonine (thr, T), tryptophan (trp, W), tyrosine (tyr, Y), valine (val, V).

HIa: Haemolysin A, also known as alpha toxin, from a staphylococcal bacterium, in particular *S. aureus*.

CP: Capsular polysaccharide

LPS: lipopolysaccharide.

wzy: the polysaccharide polymerase gene encoding an enzyme which catalyzes polysaccharide polymerization. The encoded enzyme transfers oligosaccharide units to the non-reducing end forming a glycosidic bond.

waaL: the O antigen ligase gene encoding a membrane bound enzyme. The encoded enzyme transfers undecaprenyl-diphosphate (UPP)-bound O antigen to the lipid A core oligosaccharide, forming lipopolysaccharide.

Und-PP: undecaprenyl pyrophosphate.

Und-P: undecaprenyl phosphate

Reducing end: the reducing end of an oligosaccharide or polysaccharide is the monosaccharide with a free anomeric carbon that is not involved in a glycosidic bond and is thus capable of converting to the open-chain form.

As used herein, the term "bioconjugate" refers to conjugate between a protein (e.g. a carrier protein) and an antigen (e.g. a saccharide) prepared in a host cell background, wherein host cell machinery links the antigen to the protein (e.g. N-links).

As used herein, the term "effective amount," in the context of administering a therapy (e.g. an immunogenic composition or vaccine of the invention) to a subject refers to the amount of a therapy which has a prophylactic and/or therapeutic effect(s). In certain embodiments, an "effective amount" refers to the amount of a therapy which is sufficient to achieve one, two, three, four, or more of the following effects: (i) reduce or ameliorate the severity of a bacterial infection or symptom associated therewith; (ii) reduce the duration of a bacterial infection or symptom associated therewith; (iii) prevent the progression of a bacterial infection or symptom associated therewith; (iv) cause regression of a bacterial infection or symptom associated therewith; (v) prevent the development or onset of a bacterial infection, or symptom associated therewith; (vi) prevent the recurrence of a bacterial infection or symptom associated therewith; (vii) reduce organ failure associated with a bacterial infection; (viii) reduce hospitalization of a subject having a bacterial infection; (ix) reduce hospitalization length of a subject having a bacterial infection; (x) increase the survival of a subject with a bacterial infection; (xi) eliminate a bacterial infection in a subject; (xii) inhibit or reduce a bacterial replication in a subject; and/or (xiii) enhance or improve the prophylactic or therapeutic effect(s) of another therapy.

As used herein, the term "subject" refers to an animal, in particular a mammal such as a primate (e.g. human).

As used herein, the term "donor oligosaccharide or polysaccharide" refers to an oligosaccharide or polysaccharide from which a oligosaccharide or polysaccharide is derived. Donor oligosaccharides and polysaccharides, as used herein, comprise a hexose monosaccharide (e.g. glucose) at the reducing end of the first repeat unit. Use of the term donor oligosaccharide or polysaccharide is not meant to suggest that an oligosaccharide or polysaccharide is modified in situ. Rather, use of the term donor oligosaccharide or polysaccharide is meant to refer to an oligosaccharide or polysaccharide that, in its wild-type state, is a weak substrate for oligosaccharyl transferase (e.g. PgIB) activity or is not a substrate for oligosaccharyl transferase (e.g. PgIB) activity.

Exemplary donor oligosaccharides or polysaccharides include those from bacteria, including *S. aureus* CP5 and CP8. Those of skill in the art will readily be able determine whether an oligosaccharide or polysaccharide comprises a hexose monosaccharide (e.g. glucose) at the reducing end of the first repeat unit, and thus whether such an oligosaccharide or polysaccharide is a donor oligosaccharide or polysaccharide as encompassed herein.

As used herein, the term "hexose monosaccharide derivative" refers to a derivative of a hexose monosaccharide that can be a substrate for oligosaccharyl transferase activity. In general, hexose monosaccharide derivatives comprise a monosaccharide comprising an acetamido group at position 2. Exemplary hexose monosaccharide derivatives include GlcNAc, HexNAc, deoxy HexNAc, or 2,4-diacetamido-2,4,6-trideoxyhexose.

As used herein, the term "hybrid oligosaccharide or polysaccharide" refers to an engineered oligosaccharide or polysaccharide that does not comprise a hexose at the reducing end of the first repeat unit, but instead comprises a hexose monosaccharide derivative at the reducing end of the first repeat unit.

As used herein, reference to a percentage sequence identity between two amino or nucleic acid sequences means that, when aligned, that percentage of amino acids or bases are the same in comparing the two sequences. This alignment and the percent homology or sequence identity can be determined using software programs known in the art, for example those described in section 7.7.18 of *Current Protocols in Molecular Biology* (F. M. Ausubel et al., eds., 1987, Supplement 30). A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) *Adv. Appl. Math.* 2: 482-489. Percentage identity to any particular sequence (e.g. to a particular SEQ ID) is ideally calculated over the entire length of that sequence. The percentage sequence identity between two sequences of different lengths is preferably calculated over the length of the longer sequence.

As used herein, the term "immunogenic fragment" is a portion of an antigen smaller than the whole, that is capable of eliciting a humoral and/or cellular immune response in a host animal, e.g. human, specific for that fragment. Fragments of a protein can be produced using techniques known in the art, e.g. recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Typically, fragments comprise at least 10, 20, 30, 40 or 50 contiguous amino acids of the full length sequence. Fragments may be readily modified by adding or removing 1, 2, 3, 4, 5, 6, 7, 8, 9, 10, 20, 30, 40 or 50 amino acids from either or both of the N and C termini.

As used herein, the term "conservative amino acid substitution" involves substitution of a native amino acid residue with a non-native residue such that there is little or no effect on the size, polarity, charge, hydrophobicity, or hydrophilicity of the amino acid residue at that position, and without resulting in decreased immunogenicity. For example, these may be substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Conservative amino acid modifications to the sequence of a polypeptide (and the corresponding modifications to the encoding nucleotides) may produce polypeptides having functional and chemical characteristics similar to those of a parental polypeptide.

As used herein, the term "deletion" is the removal of one or more amino acid residues from the protein sequence. Typically, no more than about from 1 to 6 residues (e.g. 1 to 4 residues) are deleted at any one site within the protein molecule.

As used herein, the term "insertion" is the addition of one or more non-native amino acid residues in the protein sequence. Typically, no more than about from 1 to 6 residues (e.g. 1 to 4 residues) are inserted at any one site within the protein molecule.

As used herein, the term 'comprising' indicates that other components in addition to those named may be present, whereas the term 'consisting of' indicates that other components are not present, or not present in detectable amounts. The term 'comprising' naturally includes the term 'consisting of'.

Proteins

The present invention provides a modified HIa protein comprising (or consisting of) an amino acid sequence of SEQ ID NO. 1 or an amino acid sequence at least 80%, 85%, 90%, 91%, 92%, 93%, 94%, 95%, 96%, 97%, 98% or 99% identical to SEQ ID NO. 1, modified in that the amino acid sequence comprises amino acid substitutions at positions H48 and G122 of SEQ ID NO. 1 or at equivalent positions within an amino acid sequence at least 80%, 85%, 90%, 92%, 95%, 96%, 97%, 98% or 99% identical to SEQ ID NO. 1, wherein said substitutions are respectively H to C and G to C (e.g. H48C and G122C, for example SEQ ID NO 2 or SEQ ID NO 3). Said protein may be further modified in that the amino acid sequence comprises one or more consensus sequence(s) selected from: D/E-X-N-Z-S/T (SEQ ID NO. 11) and K-D/E-X-N-Z-S/T-K (SEQ ID NO. 12), wherein X and Z are independently any amino acid apart from proline (e.g. SEQ ID NO. 7). These sequences may be modified by addition of a signal sequence and optionally insertion of an N-terminal serine and/or alanine for cloning purposes, as described herein. The sequences may further be modified to contain detoxifying mutations, such as any one or all of the detoxifying mutations described herein. A preferred detoxifying mutation is H35L of SEQ ID No 1 or 2.

In an embodiment, the modified HIa protein of the invention may be derived from an amino acid sequence at least 80%, 85%, 90%, 92%, 95%, 96%, 97%, 98% or 99% identical to SEQ ID NO. 1 which is an immunogenic fragment and/or a variant of SEQ ID NO. 1. In an embodiment, the modified HIa protein of the invention may be derived from an immunogenic fragment of SEQ ID NO. 2 or 3 comprising at least about 15, at least about 20, at least about 40, or at least about 60 contiguous amino acid residues of the full length sequence, wherein said polypeptide is capable of eliciting an immune response specific for said amino acid sequence.

In an embodiment, the modified HIa protein of the invention may be derived from an amino acid sequence at least 80%, 85%, 90%, 92%, 95%, 96%, 97%, 98% or 99% identical to SEQ ID NO. 1 which is a variant of SEQ ID NO. 1 which has been modified by the deletion and/or addition and/or substitution of one or more amino acids (e.g. 1, 2, 3, 4, 5, 6, 7, 8, 9, 10, 11 or 12 amino acids). Amino acid substitution may be conservative or non-conservative. In one aspect, amino acid substitution is conservative. Substitutions, deletions, additions or any combination thereof may be combined in a single variant so long as the variant is an immunogenic polypeptide. In an embodiment, the modified HIa protein of the present invention may be derived from a variant in which 1 to 10, 5 to 10, 1 to 5, 1 to 3, 1 to 2 or 1 amino acids are substituted, deleted, or added in any combination. For example, the modified HIa protein of the invention may be derived from an amino acid sequence which is a variant of any one of SEQ ID NOs. 1-3 or 7 in that it has one or two additional amino acids at the N terminus, for example an initial N-terminal SA (e.g. SEQ ID NO. 6 or 10). The modified HIa protein may additionally or alternatively have one or more additional amino acids at the C terminus, for example 1, 2, 3, 4, 5, or 6 amino acids. Such additional amino acids may include a peptide tag to assist in purification, and include for example GSHRHR (e.g. SEQ ID NOs 5, 6, 9 and 10).

In an embodiment, the present invention includes fragments and/or variants which comprise a B-cell or T-cell epitope. Such epitopes may be predicted using a combination of 2D-structure prediction, e.g. using the PSIPRED program (from David Jones, Brunel Bioinformatics Group, Dept. Biological Sciences, Brunel University, Uxbridge UB8 3PH, UK) and antigenic index calculated on the basis of the method described by Jameson and Wolf (CABIOS 4:181-186 [1988]).

The term "modified HIa protein" refers to a HIa acid sequence (for example, having a HIa amino acid sequence of SEQ ID NO. 2 or an amino acid sequence at least 80%, 85%, 90%, 91%, 92%, 93%, 94%, 95%, 96%, 97%, 98% or 99% identical to SEQ ID NO. 2), which HIa amino acid sequence may be a wild-type mature HIa amino acid sequence (for example, a wild-type amino acid sequence of SEQ ID NO. 1), which has been modified by the addition, substitution or deletion of one or more amino acids (for example, substitution of H48 and G122 of SEQ ID NO. 1 with cysteine, substitution of H35 of SEQ ID NO. 1 with lysine, addition (insertion) of a consensus sequence(s) selected from D/E-X-N-Z-S/T (SEQ ID NO. 11) and K-D/E-X-N-Z-S/T-K (SEQ ID NO. 12; or by substitution of one or more amino acids by a consensus sequence(s) selected from D/E-X-N-Z-S/T (SEQ ID NO. 11) and K-D/E-X-N-Z-S/T-K (SEQ ID NO. 12)). The modified HIa protein may also comprise further modifications (additions, substitutions, deletions) as well as the addition or substitution of one or more consensus sequence(s). For example, a signal sequence and/or peptide tag may be added. Additional amino acids at the N and/or C-terminal may be included to aid in cloning (for example, after the signal sequence or before the peptide tag, where present). In an embodiment, the modified HIa protein of the invention may be a non-naturally occurring HIa protein.

In an embodiment of the invention, one or more amino acids (e.g. 1-7 amino acids, e.g. one amino acid) of the modified HIa amino acid sequence (for example, having an amino acid sequence of SEQ ID NO. 2 or a HIa amino acid sequence at least 80%, 85%, 90%, 91%, 92%, 93%, 94%, 95%, 96%, 97%, 98% or 99% identical to SEQ ID NO. 2, e.g. SEQ ID NO. 3) have been substituted by a D/E-X-N-Z-S/T (SEQ ID NO. 11) or K-D/E-X-N-Z-S/T-K (SEQ ID NO. 12) (e.g. K-D-Q-N-R-T-K (SEQ ID NO. 23)) consensus sequence. For example, a single amino acid in the HIa amino acid sequence (e.g. SEQ ID NO. 3) may be replaced with a D/E-X-N-Z-S/T (SEQ ID NO. 11) or K-D/E-X-N-Z-S/T-K (SEQ ID NO. 12) (e.g. K-D-Q-N-R-T-K (SEQ ID NO. 23)) consensus sequence (e.g. SEQ ID NO: 7). Alternatively, 2, 3, 4, 5, 6 or 7 amino acids in the HIa amino acid sequence (e.g. SEQ ID NO. 2 or a HIa amino acid sequence at least 80%, 85%, 90%, 92%, 95%, 96%, 97%, 98% or 99% identical to SEQ ID NO. 2) may be replaced with a D/E-

X-N-Z-S/T (SEQ ID NO. 11) or K-D/E-X-N-Z-S/T-K (SEQ ID NO. 12) (e.g. K-D-Q-N-R-T-K (SEQ ID NO. 23)) consensus sequence.

Introduction of a consensus sequence(s) selected from: D/E-X-N-Z-S/T (SEQ ID NO. 11) and K-D/E-X-N-Z-S/T-K (SEQ ID NO. 12) enables the modified HIa protein to be glycosylated. Thus, the present invention also provides a modified HIa protein of the invention wherein the modified HIa protein is glycosylated. In specific embodiments, the consensus sequences are introduced into specific regions of the HIa amino acid sequence, e.g. surface structures of the protein, at the N or C termini of the protein, and/or in loops that are stabilized by disulfide bridges. In an aspect of the invention, the position of the consensus sequence(s) provides improved glycosylation, for example increased yield. In an embodiment, the consensus sequence(s) selected from D/E-X-N-Z-S/T (SEQ ID NO. 11) and K-D/E-X-N-Z-S/T-K (SEQ ID NO. 12) (e.g. K-D-Q-N-R-T-K (SEQ ID NO. 23)) is added or substituted at a position corresponding to amino acid K131 of SEQ ID NO. 1 (e.g. SEQ ID NO: 7).

In an embodiment, a consensus sequence selected from D/E-X-N-Z-S/T (SEQ ID NO. 11) and K-D/E-X-N-Z-S/T-K (SEQ ID NO. 12) (e.g. K-D-Q-N-R-T-K (SEQ ID NO. 23)) has been added or substituted for one or more amino acid residues or in place of amino acid residue K131 of SEQ ID NO. 2 or in an equivalent position in an amino acid sequence at least 80%, 85%, 90%, 92%, 95%, 96%, 97%, 98% or 99% identical to SEQ ID NO. 2 (e.g. in an equivalent position in the amino acid sequence of SEQ ID NO. 3). In one aspect, a D/E-X-N-Z-S/T (SEQ ID NO. 11) or K-D/E-X-N-Z-S/T-K (SEQ ID NO. 12) (e.g. K-D-Q-N-R-T-K (SEQ ID NO. 23)) consensus sequence has been added or substituted for amino acid K131 of SEQ ID NO. 1 or in an equivalent position in an amino acid sequence at least 80%, 85%, 90%, 92%, 95%, 96%, 97%, 98% or 99% identical to SEQ ID NO. 1 (e.g. SEQ ID NO: 7).

A person skilled in the art will understand that when the HIa amino acid sequence is a variant and/or fragment of an amino acid sequence of SEQ ID NO. 2, such as an amino acid sequence at least 80%, 85%, 90%, 92%, 95%, 96%, 97%, 98% or 99% identical to SEQ ID NO. 2, the reference to "between amino acids . . . " refers to a the position that would be equivalent to the defined position, if this sequence was lined up with an amino acid sequence of SEQ ID NO. 1 in order to maximise the sequence identity between the two sequences (Sequence alignment tools are not limited to Clustal Omega (www(.)ebi(.)ac(.)ac(.)uk) MUSCLE (www(.)ebi(.)ac(.)uk), or T-coffee (www(.)tcoffee(.)org). In one aspect, the sequence alignment tool used is Clustal Omega (www(.)ebi(.)ac(.)ac(.)uk).

The addition or deletion of amino acids from the variant and/or fragment of SEQ ID NO. 1 could lead to a difference in the actual amino acid position of the consensus sequence in the mutated sequence, however, by lining the mutated sequence up with the reference sequence, the amino acid in in an equivalent position to the corresponding amino acid in the reference sequence can be identified and hence the appropriate position for addition or substitution of the consensus sequence can be established.

Introduction of such glycosylation sites can be accomplished by, e.g. adding new amino acids to the primary structure of the protein (i.e. the glycosylation sites are added, in full or in part), or by mutating existing amino acids in the protein in order to generate the glycosylation sites (i.e. amino acids are not added to the protein, but selected amino acids of the protein are mutated so as to form glycosylation sites). Those of skill in the art will recognize that the amino acid sequence of a protein can be readily modified using approaches known in the art, e.g. recombinant approaches that include modification of the nucleic acid sequence encoding the protein. Thus, in an embodiment, the present invention provides a modified HIa protein having an amino acid sequence wherein the amino acids corresponding to H48 and G122 of SEQ ID NO 1 or equivalent positions in an HIa amino acid sequence at least 80%, 85%, 90%, 92%, 95%, 96%, 97%, 98% or 99% identical to SEQ ID NO. 1 have been substituted by cysteine, and wherein a glycosylation site has been recombinantly introduced into the HIa amino acid sequence of SEQ ID NO. 1 or a HIa amino acid sequence at least 80%, 85%, 90%, 92%, 95%, 96%, 97%, 98% or 99% identical to SEQ ID NO. 1. Thus, in an embodiment, the present invention provides a modified HIa protein having an amino acid sequence comprising one or more consensus sequence(s) selected from: D/E-X-N-Z-S/T (SEQ ID NO. 11) and K-D/E-X-N-Z-S/T-K (SEQ ID NO. 12), wherein X and Z are independently any amino acid apart from proline, which have been recombinantly introduced into the HIa amino acid sequence of SEQ ID NO. 1 or a HIa amino acid sequence at least 80%, 85%, 90%, 92%, 95%, 96%, 97%, 98% or 99% identical to SEQ ID NO. 1 (e.g. SEQ ID NOs 2 or 3). The present invention also provides a method for preparing a modified HIa protein wherein one or more consensus sequence(s) selected from: D/E-X-N-Z-S/T (SEQ ID NO. 11) and K-D/E-X-N-Z-S/T-K (SEQ ID NO. 12), wherein X and Z are independently any amino acid apart from proline, are recombinantly introduced into the HIa amino acid sequence of SEQ ID NO. 1 or a HIa amino acid sequence at least 80%, 85%, 90%, 92%, 95%, 96%, 97%, 98% or 99% identical to SEQ ID NO. 1 (i.e. a recombinant modified HIa protein). In certain embodiments, the classical 5 amino acid glycosylation consensus sequence (D/E-X-N-Z-S/T (SEQ ID NO. 11)) may be extended by lysine residues for more efficient glycosylation (e.g. K-D/E-X-N-Z-S/T-K (SEQ ID NO. 12)), and thus the inserted consensus sequence may encode 5, 6, or 7 amino acids that should be inserted or that replace acceptor protein amino acids.

In one embodiment, the modified HIa protein of the invention comprises (or consists of) an amino acid sequence which is at least 80%, 85%, 90%, 92%, 95%, 96%, 97%, 98%, 99% or 100% identical to the sequence of SEQ ID NO. 2, said amino acid sequence comprising a D/E-X-N-Z-S/T (SEQ ID NO. 11) or K-D/E-X-N-Z-S/T-K (SEQ ID NO. 12) consensus sequence wherein X and Z are independently any amino acid apart from proline (e.g. K-D/E-X-N-Z-S/T-K (SEQ ID NO. 12) or K-D-Q-N-R-T-K (SEQ ID NO. 23)). In an embodiment, the modified HIa protein of the invention comprises (or consists of) the amino acid sequence of SEQ ID NO. 7. In an embodiment, the modified HIa protein of the invention comprises (or consists of) the amino acid sequence of any one of SEQ ID NOs. 1-3 or 7 with an N-terminal serine and/or alanine (i.e. S residue added at the N-terminus, e.g. SEQ ID NO: 6 or 10).

Because HIa is a toxin, it needs to be detoxified (i.e. rendered non-toxic to a mammal, e.g. human, when provided at a dosage suitable for protection) before it can be administered in vivo. A modified HIa protein of the invention may be genetically detoxified (i.e. by mutation). The genetically detoxified sequences may remove undesirable activities such as the ability to form a lipid-bilayer penetrating pore, membrane permeation, cell lysis, and cytolytic activity against human erythrocytes and other cells, in order to reduce toxicity, whilst retaining the ability to induce anti-HIa protective and/or neutralizing antibodies following administration to a human. For example, as described herein, a HIa protein may be altered so that it is biologically inactive whilst still maintaining its immunogenic epitopes.

The modified HIa proteins of the invention may be genetically detoxified by one or more point mutations. For example, residues involved in pore formation been implicated in the lytic activity of HIa. In one aspect, the modified HIa proteins of the invention may be detoxified by amino acid substitutions as described in Menzies and Kernodle (Menzies and Kernodle, 1994, Infect Immun 62, 1843-1847), for example substitution of H35, H48, H114 and/or H259 with another amino acid such as lysine. For example, the modified HIa proteins of the invention may comprise at least one amino acid substitution selected from H35L, H114L or H259L, with reference to the amino acid sequence of SEQ ID NO. 1 (or an equivalent position in an amino acid sequence at least 80%, 85%, 90%, 92%, 95%, 96%, 97%, 98% or 99% identical to SEQ ID NO. 1). Preferably, the modified HIa protein comprises the substitution H35L (e.g. SEQ ID NO: 3).

The amino acid numbers referred to herein correspond to the amino acids in SEQ ID NO. 1 and as described above, a person skilled in the art can determine equivalent amino acid positions in an amino acid sequence at least 80%, 85%, 90%, 92%, 95%, 96%, 97%, 98% or 99% identical to SEQ ID NO. 1 by alignment.

The modified HIa protein may demonstrate a reduced tendency to aggregate compared to HIa lacking disulphide bridges, e.g. wild-type or detoxified HIa (for example, HIa H35L, e.g. SEQ ID NO: 30), or other cross-linked mutants, e.g. HIa H35LY102C/G126C (SEQ ID NO: 27), HIa H35L/N121C/H48C (SEQ ID NO: 28), or HIa H35L/G122C/L52C (SEQ ID NO: 29). For example, a suitable modified HIa protein of the invention may be one that exhibits lower aggregation than wild-type HIa or HIaH35L (e.g. as detectable on Western blots or measured via chromatographic techniques, e.g IMAC or size exclusion chromatography), as described in the Examples. For instance, a suitable modified HIa protein may show aggregation levels (as determined using any of the methods described herein) of 0%, 0.0005%, 0.001%, 0.005%, 0.01%, 0.05%, 0.1%, 0.5%, 1%, or 5%; about 0%, 0.0005%, 0.001%, 0.005%, 0.01%, 0.05%, 0.1%, 0.5%, 1% or 5%; less than 0.0005%, 0.001%, 0.005%, 0.01%, 0.05%, 0.1%, 0.5%, 1% or 5%; <10%, <20%, <30%, <40%, <50%, <60%, <70%, <80% or <90% of that the wild-type, detoxified (e.g. HIaH35L) HIa or other cross-linked HIa. For example, when using size exclusion chromatography or IMAC the peak representing monomeric HIa may be higher than wild-type HIa or HIaH35L or other cross-linked HIa, and/or the peak representing aggregated HIa may be lower.

The modified HIa protein may be produced with a greater overall yield than HIa lacking disulphide bridges, e.g. wild-type or detoxified HIa (for example, HIa H35L, e.g. SEQ ID NO: 30), or other cross-linked mutants, e.g. HIa H35LY102C/G126C (SEQ ID NO: 27), HIa H35L/N121C/H48C (SEQ ID NO: 28), or HIa H35L/G122C/L52C (SEQ ID NO: 29). Where the overall yield is not greater, the modified HIa protein may be produced with a greater yield of HIa monomer than HIa lacking disulphide bridges, e.g. wild-type or detoxified HIa (for example, HIa H35L, e.g. SEQ ID NO: 30), or other cross-linked mutants, e.g. HIa H35L/Y102C/G126C (SEQ ID NO: 27), HIa H35L/N121C/H48C (SEQ ID NO: 28), or HIa H35L/G122C/L52C (SEQ ID NO: 29). For instance, yield of the modified HIa protein may be increased by 10%, 20%, 30%, 40%, 50%, 60%, 70%, 80% 90%, 110%, 120%, 150%, 200% or more, or about 10%, 20%, 30%, 40%, 50%, 60%, 70%, 80% 90%, 110%, 120%, 150%, 200% or more, compared to that of the wild-type, detoxified (e.g. HIaH35L) HIa or other cross-linked Ha. Protein yield may be determined as described below.

The haemolytic activity of the modified HIa protein of the invention may be assayed and characterised by methods described for example in Menzies and Kernodle, 1994, Infect Immun 62, 1843-1847. An in vitro haemolysis assay may be used to measure the haemolytic (e.g. cytolytic) activity of modified HIa protein relative to wild-type HIa. A haemolysis inhibition assay may be used to measure the ability of antisera raised against a modified HIa protein of the invention to inhibit haemolysis by Ha, and (typically) comparing anti-(modified Ha) antisera to anti-(wild-type Ha) antisera. For example, a suitable modified HIa protein of the invention may be one that exhibits lower haemolytic activity than wild-type HIa (e.g. via an in vitro haemolysis assay). For instance, a suitable modified HIa protein may have a specific activity (as determined using the in vitro haemolysis assay) of about (referring to each of the following values independently) 0%, 0.0005%, 0.001%, 0.005%, 0.01%, 0.05%, 0.1%, 0.5%, 1%, 5% or <10% the specific activity of the wild-type HIa. A suitable modified HIa protein of the invention may also be one that, following administration to a host, causes the host to produce antibodies that inhibit haemolysis by wild-type HIa (e.g. via a haemolysis inhibition assay), is immunogenic (e.g. induces the production of antibodies against wtHIa), and/or protective (e.g. induces an immune response that protects the host against infection by or limits an already-existing infection). Assays may be used as described in the Examples.

In an embodiment, the modified HIa protein of the invention further comprises a "peptide tag" or "tag", i.e. a sequence of amino acids that allows for the isolation and/or identification of the modified HIa protein. For example, adding a tag to a modified HIa protein of the invention can be useful in the purification of that protein and, hence, the purification of conjugate vaccines comprising the tagged modified HIa protein. Exemplary tags that can be used herein include, without limitation, histidine (HIS) tags. I one embodiment, the tag is a hexa-histidine tag. In another embodiment, the tag is a HR tag, for example an HRHR tag. In certain embodiments, the tags used herein are removable, e.g. removal by chemical agents or by enzymatic means, once they are no longer needed, e.g. after the protein has been purified. Optionally the peptide tag is located at the C-terminus of the amino acid sequence. Optionally the peptide tag comprises six histidine residues at the C-terminus of the amino acid sequence. Optionally the peptide tag comprises four HR residues (HRHR) at the C-terminus of the amino acid sequence. The peptide tag may be comprise or be preceded by one, two or more additional amino acid residues, for example alanine, serine and/or glycine residues, e.g. GS. In one aspect, the modified HIa protein of the invention comprises (or consists of) an amino acid sequence which is at least 80%, 85%, 90%, 92%, 95%, 97%, 98%, 99% or 100% identical to the sequence of SEQ ID NO. 2 or SEQ ID NO. 3, said amino acid sequence comprising a D/E-X-N-Z-S/T (SEQ ID NO. 11) consensus sequence wherein X and Z are independently any amino acid apart from proline (e.g. K-D/E-X-N-Z-S/T-K (SEQ ID NO. 12) or K-D-Q-N-R-T-K (SEQ ID NO. 23)) and at least one amino acid substitution selected from H35L, H48C and G122C and a GSHRHR peptide tag at the C-terminus of the amino acid sequence. Optionally, the modified HIa protein of the invention has an amino acid sequence at least 97%, 98%, 99% or 100% identical to SEQ ID NO. 5, 6, 9 or 10.

In an embodiment, the modified HIa protein of the invention comprises a signal sequence which is capable of directing the HIa protein to the periplasm of a host cell (e.g. bacterium). In a specific embodiment, the signal sequence is from *E. coli* flagellin (FlgI) [MIKFLSALILLLVTTAAQA (Seq ID NO. 13)]. In other embodiments, the signal sequence is from *E. coli* outer membrane porin A (OmpA) [MKKTAIAIAVALAGFATVAQA (Seq ID NO. 14)], *E. coli* maltose binding protein (MalE) [MKIKTGARILALSALTTMMFSASALA (Seq ID NO. 15)], *Erwinia carotovorans* pectate lyase (PelB) [MKYLLPTAAAGLLLLAAQPAMA (Seq ID NO. 16)], heat labile *E. coli* enterotoxin LTIlb [MSFKKIIKAFVIMAALVSVQAHA (Seq ID NO. 17)], *Bacillus subtilis* endoxylanase XynA [MFKFKKKFLVGLTAAFMSISMFSATASA (Seq ID NO. 18)], *E. coli* DsbA [MKKIWLALAGLVLAFSASA (Seq ID NO. 19)], TolB [MKQALRVAFGFLILWASVLHA (Seq ID NO. 20)] or SipA [MKMNKKVLLTSTMAASLLSVASVQAS (SEQ ID NO. 21)]. In an embodiment, the signal sequence has an amino acid sequence at least 80%, 85%, 90%, 92%, 95%, 96%, 97%, 98%, 99% or 100% identical to a SEQ ID NO. 13-21. In one aspect, the signal sequence has an amino acid sequence at least 80%, 85%, 90%, 95%, 96%, 97%, 98%, 99% or 100% identical to *E. coli* flagellin signal sequence (FlgI) [MIKFLSALILLLVTTAAQA (Seq ID NO. 13)]. Exemplary modified HIa sequences comprising a signal sequence are SEQ ID NOs: 4, 5, 8 and 9.

In an embodiment, a serine and/or alanine residue is added between the signal sequence and the start of the sequence of the mature protein, e.g. SA or S, preferably S. Such a reside or residues have the advantage of leading to more efficient cleavage of the leader sequence.

In one aspect, the modified HIa protein of the invention comprises (or consists of) an amino acid sequence which is at least 97%, 98%, 99% or 100% identical to the sequence of SEQ ID NO. 1, said amino acid sequence comprising the amino acid substitutions G122 to C and H48 to C, and optionally also H35 to L, a D/E-X-N-Z-S/T (SEQ ID NO. 11) consensus sequence wherein X and Z are independently any amino acid apart from proline (e.g. K-D/E-X-N-Z-S/T-K (SEQ ID NO. 12) or K-D-Q-N-R-T-K (SEQ ID NO. 23)), a HRHR tag (SEQ ID NO: 25) at the C-terminus of the amino acid sequence and optionally a signal sequence, preferably a FlgL signal sequence (SEQ ID NO: 13)) at the N-terminus of the signal sequence, optionally followed by a SA dipeptide. In an embodiment, a modified HIa protein of the invention has an amino acid sequence at least 97%, 98%, 99% or 100% identical to an amino acid sequence selected from SEQ ID NO. 9 or SEQ ID NO. 10. In another embodiment, the present invention provides a modified HIa protein having an amino acid sequence selected from SEQ ID NOs. 7-10.

A further aspect of the invention is a polynucleotide encoding a modified HIa protein of the invention. For example, a polynucleotide encoding a modified HIa protein, having a nucleotide sequence that encodes a polypeptide with an amino acid sequence that is at least 97%, 98%, 99% or 100% identical to any one of SEQ ID NO. 2-10. A vector comprising such a polynucleotide is a further aspect of the invention.

Conjugates

The present invention also provides a conjugate (e.g. bioconjugate) comprising (or consisting of) a modified HIa protein of the invention, wherein the modified HIa protein is linked, e.g. covalently linked to an antigen, preferably a polysaccharide or oligosaccharide antigen.

In an embodiment, the conjugate comprises a conjugate (e.g. bioconjugate) comprising (or consisting of) a modified HIa protein of the invention having an amino acid sequence which is at least 97%, 98%, 99% or 100% identical to the sequence of SEQ ID NO. 1-10 covalently linked to an antigen, preferably a polysaccharide or oligosaccharide antigen, wherein the antigen is linked (either directly or through a linker) to an amino acid residue of the modified HIa protein.

In an embodiment, the modified HIa protein is covalently linked to the antigen through a chemical linkage obtainable using a chemical conjugation method (i.e. the conjugate is produced by chemical conjugation).

In an embodiment, the chemical conjugation method is selected from the group consisting of carbodiimide chemistry, reductive animation, cyanylation chemistry (for example CDAP chemistry), maleimide chemistry, hydrazide chemistry, ester chemistry, and N-hydroysuccinimide chemistry. Conjugates can be prepared by direct reductive amination methods as described in, US200710184072 (Hausdorff) U.S. Pat. No. 4,365,170 (Jennings) and U.S. Pat. No. 4,673,574 (Anderson). Other methods are described in EP-0-161-188, EP-208375 and EP-0-477508. The conjugation method may alternatively rely on activation of the saccharide with 1-cyano-4-dimethylamino pyridinium tetrafluoroborate (CDAP) to form a cyanate ester. Such conjugates are described in PCT published application WO 93/15760 Uniformed Services University and WO 95/08348 and WO 96/29094. See also Chu C. et al Infect. Immunity, 1983 245 256.

In general the following types of chemical groups on a modified HIa protein can be used for coupling/conjugation:

A) Carboxyl (for instance via aspartic acid or glutamic acid). In one embodiment this group is linked to amino groups on saccharides directly or to an amino group on a linker with carbodiimide chemistry e.g. with EDAC.

B) Amino group (for instance via lysine). In one embodiment this group is linked to carboxyl groups on saccharides directly or to a carboxyl group on a linker with carbodiimide chemistry e.g. with EDAC. In another embodiment this group is linked to hydroxyl groups activated with CDAP or CNBr on saccharides directly or to such groups on a linker; to saccharides or linkers having an aldehyde group; to saccharides or linkers having a succinimide ester group.

C) Sulphydryl (for instance via cysteine). In one embodiment this group is linked to a bromo or chloro acetylated saccharide or linker with maleimide chemistry. In one embodiment this group is activated/modified with bis diazobenzidine.

D) Hydroxyl group (for instance via tyrosine). In one embodiment this group is activated/modified with bis diazobenzidine.

E) Imidazolyl group (for instance via histidine). In one embodiment this group is activated/modified with bis diazobenzidine.

F) Guanidyl group (for instance via arginine).

G) Indolyl group (for instance via tryptophan).

On a saccharide, in general the following groups can be used for a coupling: OH, COOH or $NH_2$. Aldehyde groups can be generated after different treatments such as: periodate, acid hydrolysis, hydrogen peroxide, etc.

Direct Coupling Approaches:

Saccharide-OH+CNBr or CDAP→cyanate ester+$NH_2$-Protein→conjugate

Saccharide-aldehyde+$NH_2$-Protein→Schiff base+NaCNBH3→conjugate

Saccharide-COOH+$NH_2$-Protein+EDAC→conjugate

Saccharide-$NH_2$+COOH-Protein+EDAC→conjugate

Indirect Coupling Via Spacer (Linker) Approaches:

Saccharide-OH+CNBr or CDAP→cyanate ester+$NH_2$-$NH_2$→saccharide-$NH_2$+COOH-Protein+EDAC→conjugate Saccharide-OH+CNBr or CDAP→cyanate ester+$NH_2$-SH→saccharide-SH+SH-Protein (native Protein with an exposed cysteine or obtained after modification of amino groups of the protein by SPDP for instance)→saccharide-S-S-Protein Saccharide-OH+CNBr or CDAP→cyanate ester+$NH_2$-SH→saccharide-SH+maleimide-Protein (modification of amino groups)→conjugate Saccharide-OH+CNBr or CDAP→cyanate ester+$NH_2$-SH→Saccharide-SH+haloacetylated-Protein→Conjugate Saccharide-COOH+EDAC+$NH_2$-$NH_2$→saccharide-$NH_2$+EDAC+COOH-Protein→conjugate Saccharide-COOH+EDAC+$NH_2$-SH→saccharide-SH+SH-Protein (native Protein with an exposed cysteine or obtained after modification of amino groups of the protein by SPDP for instance)→saccharide-S-S-Protein Saccharide-COOH+EDAC+$NH_2$-SH→saccharide-SH+maleimide-Protein (modification of amino groups)→conjugate Saccharide-COOH+EDAC+$NH_2$-SH→Saccharide-SH+haloacetylated-Protein→Conjugate Saccharide-Aldehyde+$NH_2$-$NH_2$→saccharide-$NH_2$+EDAC+COOH-Protein→conjugate Note: instead of EDAC above, any suitable carbodiimide may be used.

In an embodiment, the antigen is directly linked to the modified HIa protein.

In an embodiment, the antigen is attached to the modified HIa protein via a linker. Optionally, the linker is selected from the group consisting of linkers with 4-12 carbon atoms, bifunctional linkers, linkers containing 1 or 2 reactive amino groups at the end, B-proprionamido, nitrophenyl-ethylamine, haloacyl halides, 6-aminocaproic acid and ADH. The activated saccharide may thus be coupled directly or via a spacer (linker) group to an amino group on the modified HIa protein. For example, the spacer could be cystamine or cysteamine to give a thiolated polysaccharide which could be coupled to the modified HIa via a thioether linkage obtained after reaction with a maleimide-activated modified HIa protein (for example using GMBS (4-Maleimidobutyric acid N-hydroxysuccinimide ester)) or a haloacetylated modified HIa protein (for example using SIAB (succinimidyl (4-iodoacetyl)aminobenzoate), or SIA (succinimidyl iodoacetate), or SBAP (succinimidyl-3-(bromoacetamide) propionate)). In an embodiment, the cyanate ester (optionally made by CDAP chemistry) is coupled with hexane diamine or ADH (adipic acid dihydrazide) and the amino-derivatised saccharide is conjugated to the modified HIa protein using carbodiimide (e.g. 1-Ethyl-3-(3-dimethylaminopropyl)carbodiimide (EDAC or EDC)) chemistry via a carboxyl group on the protein modified HIa. Such conjugates are described in PCT published application WO 93/15760 Uniformed Services University and WO 95/08348 and WO 96/29094.

In an embodiment, the amino acid residue on the modified HIa protein to which the antigen is linked is not an asparagine residue and in this case, the conjugate is typically produced by chemical conjugation. In an embodiment, the amino acid residue on the modified HIa protein to which the antigen is linked is selected from the group consisting of: Ala, Arg, Asp, Cys, Gly, Glu, Gln, His, le, Leu, Lys, Met, Phe, Pro, Ser, Thr, Trp, Tyr, and Val. Optionally, the amino acid is: an amino acid containing a terminal amine group, a lysine, an arginine, a glutaminic acid, an aspartic acid, a cysteine, a tyrosine, a histidine or a tryptophan. Optionally, the antigen is covalently linked to amino acid on the modified HIa protein selected from: aspartic acid, glutamic acid, lysine, cysteine, tyrosine, histidine, arginine or tryptophan.

In an embodiment, the amino acid residue on the modified HIa protein to which the antigen is linked is not part of the D/E-X-N-Z-S/T (SEQ ID NO. 11) and K-D/E-X-N-Z-S/T-K (SEQ ID NO. 12) consensus sequence. In an embodiment, the amino acid residue on the modified HIa protein to which the antigen is linked is not the asparagine residue in the D/E-X-N-Z-S/T (SEQ ID NO. 11) and K-D/E-X-N-Z-S/T-K (SEQ ID NO. 12) consensus sequence.

Alternatively, in another embodiment, the antigen is linked to an amino acid on the modified HIa protein selected from asparagine, aspartic acid, glutamic acid, lysine, cysteine, tyrosine, histidine, arginine or tryptophan (e.g. asparagine). In another embodiment, the amino acid residue on the modified HIa protein to which the antigen is linked is an asparagine residue. In another embodiment, the amino acid residue on the modified HIa protein to which the antigen is linked is part of the D/E-X-N-Z-S/T (SEQ ID NO. 11) and K-D/E-X-N-Z-S/T-K (SEQ ID NO. 12) consensus sequence (e.g. the asparagine in the D/E-X-N-Z-S/T (SEQ ID NO. 11) and K-D/E-X-N-Z-S/T-K (SEQ ID NO. 12) consensus sequence).

Polysaccharide Antigens

In an embodiment, one of the antigens in a conjugate (e.g. bioconjugate) of the invention is a saccharide such as a bacterial capsular saccharide, a bacterial lipopolysaccharide or a bacterial oligosaccharide. In an embodiment the antigen is a bacterial capsular saccharide.

The saccharides may be selected from a group consisting of: *Staphylococcus aureus* type 5 capsular saccharide, *Staphylococcus aureus* type 8 capsular saccharide, *N. meningitidis* serogroup A capsular saccharide (MenA), *N. meningitidis* serogroup C capsular saccharide (MenC), *N. meningitidis* serogroup Y capsular saccharide (MenY), *N. meningitidis* serogroup W capsular saccharide (MenW), *H. influenzae* type b capsular saccharide (Hib), Group B *Streptococcus* group I capsular saccharide, Group B *Streptococcus* group II capsular saccharide, Group B *Streptococcus* group III capsular saccharide, Group B *Streptococcus* group IV capsular saccharide, Group B *Streptococcus* group V capsular saccharide, Vi saccharide from *Salmonella typhi, N. meningitidis* LPS (such as L3 and/or L2), *M. catarrhalis* LPS, *H. influenzae* LPS, *Shigella* O-antigens, *P. aeruginosa* O-antigens, *E. coli* O-antigens or *S. pneumoniae* capsular polysaccharide.

In an embodiment, the antigen is a bacterial capsular saccharide from *Staphylococcus aureus*. The bacterial capsular saccharide from *Staphylococcus aureus* may be selected from a *Staphylococcus aureus* serotype 5 or 8 capsular saccharide. For example, the antigen may be an *Staphylococcus aureus* capsular saccharide from serotype 5.

In an embodiment of the invention, the antigen is a repeat unit of a bacterial capsular saccharide from *Staphylococcus aureus*. In an embodiment of the invention, the antigen comprises a repeat unit of a bacterial capsular saccharide from *Staphylococcus aureus* serotype 5 or 8.

In an embodiment of the invention, the antigen comprises a repeat unit of a bacterial capsular saccharide from *Staphylococcus aureus* serotype 5. In an embodiment of the invention, the antigen comprises:

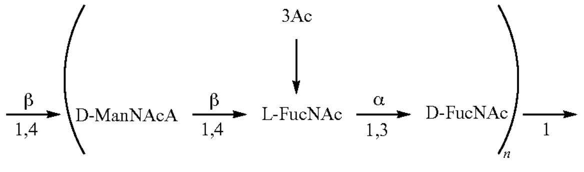

where 'n' is any whole number, eg 2, 3, 4, 5, 6, 7, 8, 9, 10 or more as described below.

In an embodiment of the invention, the antigen comprises a repeat unit of a bacterial capsular saccharide from *Staphylococcus aureus* serotype 8. In an embodiment of the invention, the antigen comprises:

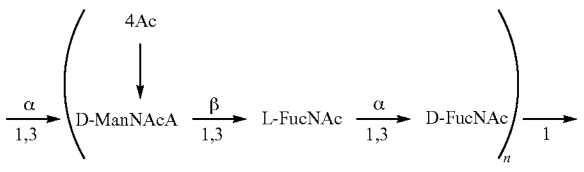

where 'n' is any whole number, eg 2, 3, 4, 5, 6, 7, 8, 9, 10 or more as described below.

In an embodiment, the antigen is a polysaccharide or oligosaccharide. In an embodiment, the antigen comprises two or more monosaccharides, for example 2, 3, 4, 5, 6, 7, 8, 9, 10 or more monosaccharides. In an embodiment, the antigen is an oligosaccharide containing no more than 20, 15, 12, 10, 9, or 8 monosaccharides. In an embodiment, the antigen is an oligosaccharide containing no more than no more than 500, 400, 300, 200, 100, 90, 80, 70, 60, 50, 40, 30, 20, 10 or 5 monosaccharides.

Host Cell

The present invention also provides a host cell comprising:

i) one or more nucleic acids that encode glycosyltransferase(s);

ii) a nucleic acid that encodes an oligosaccharyl transferase;

iii) a nucleic acid that encodes a modified HIa protein of the invention; and optionally iv) a nucleic acid that encodes a polymerase (e.g. wzy).

Host cells that can be used to produce the bioconjugates of the invention, include archea, prokaryotic host cells, and eukaryotic host cells. Exemplary prokaryotic host cells for use in production of the bioconjugates of the invention, without limitation, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species. In a specific embodiment, the host cell is *E. coli.*

In an embodiment, the host cells used to produce the bioconjugates of the invention are engineered to comprise heterologous nucleic acids, e.g. heterologous nucleic acids that encode one or more carrier proteins and/or heterologous nucleic acids that encode one or more proteins, e.g. genes encoding one or more proteins. In a specific embodiment, heterologous nucleic acids that encode proteins involved in glycosylation pathways (e.g. prokaryotic and/or eukaryotic glycosylation pathways) may be introduced into the host cells of the invention. Such nucleic acids may encode proteins including, without limitation, oligosaccharyl transferases, epimerases, flippases, polymerases, and/or glycosyltransferases. Heterologous nucleic acids (e.g. nucleic acids that encode carrier proteins and/or nucleic acids that encode other proteins, e.g. proteins involved in glycosylation) can be introduced into the host cells of the invention using methods such as electroporation, chemical transformation by heat shock, natural transformation, phage transduction, and conjugation. In specific embodiments, heterologous nucleic acids are introduced into the host cells of the invention using a plasmid, e.g. the heterologous nucleic acids are expressed in the host cells by a plasmid (e.g. an expression vector). In another specific embodiment, heterologous nucleic acids are introduced into the host cells of the invention using the method of insertion described in International Patent application No. PCT/EP2013/068737 (published as WO 14/037585).

Thus, the present invention also provides a host cell comprising:

i) one or more nucleic acids that encode glycosyltransferase(s);

ii) a nucleic acid that encodes an oligosaccharyl transferase;

iii) a nucleic acid that encodes a modified HIa protein of the invention;

iv) a nucleic acid that encodes a polymerase (e.g. wzy); and vi) a nucleic acid that encodes a flippase (e.g. wxy).

In an embodiment, additional modifications may be introduced (e.g. using recombinant techniques) into the host cells of the invention. For example, host cell nucleic acids (e.g. genes) that encode proteins that form part of a possibly competing or interfering glycosylation pathway (e.g. compete or interfere with one or more heterologous genes involved in glycosylation that are recombinantly introduced into the host cell) can be deleted or modified in the host cell background (genome) in a manner that makes them inactive/dysfunctional (i.e. the host cell nucleic acids that are deleted/modified do not encode a functional protein or do not encode a protein whatsoever). In an embodiment, when nucleic acids are deleted from the genome of the host cells of the invention, they are replaced by a desirable sequence, e.g. a sequence that is useful for glycoprotein production.

Exemplary genes that can be deleted in host cells (and, in some cases, replaced with other desired nucleic acid sequences) include genes of host cells involved in glycolipid biosynthesis, such as waaL (see, e.g. Feldman et al. 2005, PNAS USA 102:3016-3021), the lipid A core biosynthesis cluster (waa), galactose cluster (gal), arabinose cluster (ara), colonic acid cluster (wc), capsular polysaccharide cluster, undecaprenol-pyrophosphate biosynthesis genes (e.g. uppS (Undecaprenyl pyrophosphate synthase), uppP (Undecaprenyl diphosphatase)), Und-P recycling genes, metabolic enzymes involved in nucleotide activated sugar biosynthesis, enterobacterial common antigen cluster, and prophage O antigen modification clusters like the gtrABS cluster.

Such a modified prokaryotic host cell comprises nucleic acids encoding enzymes capable of producing a bioconjugate comprising an antigen, for example a saccharide antigen attached to a modified HIa protein of the invention. Such host cells may naturally express nucleic acids specific for production of a saccharide antigen, or the host cells may be made to express such nucleic acids, i.e. in certain embodiments said nucleic acids are heterologous to the host cells. In certain embodiments, one or more of said nucleic acids specific for production of a saccharide antigen are heterologous to the host cell and integrated into the genome of the host cell. In certain embodiments, the host cells of the invention comprise nucleic acids encoding additional enzymes active in the N-glycosylation of proteins, e.g. the host cells of the invention further comprise a nucleic acid encoding an oligosaccharyl transferase and/or one or more nucleic acids encoding other glycosyltransferases.

Nucleic acid sequences comprising capsular polysaccharide gene clusters can be inserted into the host cells of the invention. In a specific embodiment, the capsular polysaccharide gene cluster inserted into a host cell of the invention is a capsular polysaccharide gene cluster from an *E. coli* strain, a *Staphylococcus* strain (e.g. *S. aureus*), a *Streptococcus* strain (e.g. *S. pneumoniae, S. pyrogenes, S. agalacticae*), or a *Burkholderia* strain (e.g. *B mallei, B. pseudomallei, B. thailandensis*). Disclosures of methods for making such host cells which are capable of producing bioconjugates are found in WO 06/119987, WO 09/104074, WO 11/62615, WO 11/138361, WO 14/57109, WO14/72405 and WO16/20499.

In an embodiment, the host cell comprises a nucleic acid that encodes a modified HIa protein in a plasmid in the host cell.

Glycosylation Machinery

The host cells of the invention comprise, and/or can be modified to comprise, nucleic acids that encode genetic machinery (e.g. glycosyltransferases, flippases, polymerases, and/or oligosaccharyltransferases) capable of producing hybrid oligosaccharides and/or polysaccharides, as well as genetic machinery capable of linking antigens to the modified HIa protein of the invention.

*S. aureus* capsular polysaccharides are assembled on the bacterial membrane carrier lipid undecaprenyl pyrophosphate by a conserved pathway that shares homology to the polymerase-dependent pathway of O polysaccharide synthesis in Gram-negative bacteria. O antigen assembly is initiated by the transfer of a sugar phosphate from a DP-donor to undecaprenyl phosphate. The lipid linked O antigen is assembled at the cytoplasmic side of the inner membrane by sequential action of different glycosyltransferases. The glycolipid is then flipped to the periplasmic space and polymerised. By replacing the O antigen ligase WaaL with the oligosaccharyltransferase PglB, the polymerised O antigen can be transferred to a protein carrier rather than to the lipid A core.

Glycosyltransferases

The host cells of the invention comprise nucleic acids that encode glycosyltransferases that produce an oligosaccharide or polysaccharide repeat unit. In an embodiment, said repeat unit does not comprise a hexose at the reducing end, and said oligosaccharide or polysaccharide repeat unit is derived from a donor oligosaccharide or polysaccharide repeat unit that comprises a hexose at the reducing end.

In an embodiment, the host cells of the invention may comprise a nucleic acid that encodes a glycosyltransferase that assembles a hexose monosaccharide derivative onto undecaprenyl pyrophosphate (Und-PP). In one aspect, the glycosyltransferase that assembles a hexose monosaccharide derivative onto Und-PP is heterologous to the host cell and/or heterologous to one or more of the genes that encode glycosyltransferase(s). Said glycosyltransferase can be derived from, e.g. *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species. In a specific embodiment, the glycosyltransferase that assembles a hexose monosaccharide derivative onto Und-PP is wecA, optionally from *E. coli* (wecA can assemble GlcNAc onto UndP from UDP-GlcNAc). In an embodiment, the hexose monosaccharide is selected from the group consisting of glucose, galactose, rhamnose, arabinotol, fucose and mannose (e.g. galactose).

In an embodiment, the host cells of the invention may comprise nucleic acids that encode one or more glycosyltransferases capable of adding a monosaccharide to the hexose monosaccharide derivative assembled on Und-PP. In a specific embodiment, said one or more glycosyltransferases capable of adding a monosaccharide to the hexose monosaccharide derivative is the galactosyltransferase (wfeD) from *Shigella* boyedii. In another specific embodiment, said one or more glycosyltransferases capable of adding a monosaccharide to the hexose monosaccharide derivative is the galactofuranosyl transferase (wbeY) from *E. coli* O28. In another specific embodiment, said one or more glycosyltransferases capable of adding a monosaccharide to the hexose monosaccharide derivative is the galactofuranosyl transferase (wfdK) from *E. coli* O167. Galf-transferases, such as wfdK and wbeY, can transfer Galf (Galactofuranose) from UDP-Galf to -GlcNAc-P-P-Undecaprenyl. In another specific embodiment, said one or more glycosyltransferases capable of adding a monosaccharide to the hexose monosaccharide derivative are the galactofuranosyl transferase (wbeY) from *E. coli* O28 and the galactofuranosyl transferase (wfdK) from *E. coli* O167.

In an embodiment, the host cells of the invention comprise nucleic acids that encode glycosyltransferases that assemble the donor oligosaccharide or polysaccharide repeat unit onto the hexose monosaccharide derivative.

In an embodiment, the glycosyltransferases that assemble the donor oligosaccharide or polysaccharide repeat unit onto the hexose monosaccharide derivative comprise a glycosyltransferase that is capable of adding the hexose monosaccharide present at the reducing end of the first repeat unit of the donor oligosaccharide or polysaccharide to the hexose monosaccharide derivative. Exemplary glycosyltransferases include galactosyltransferases (wciP), e.g. wciP from *E. coli* O21.

In one embodiment, the glycosyltransferases that assemble the donor oligosaccharide or polysaccharide repeat unit onto the hexose monosaccharide derivative comprise a glycosyltransferase that is capable of adding the monosaccharide that is adjacent to the hexose monosaccharide present at the reducing end of the first repeat unit of the donor oligosaccharide or polysaccharide to the hexose monosaccharide present at the reducing end of the first repeat unit of the donor oligosaccharide or polysaccharide. Exemplary glycosyltransferases include glucosyltransferase (wciQ), e.g. wciQ from *E. coli* O21.

In an embodiment, a host cell of the invention comprises glycosyltransferases for synthesis of the repeat units of an oligosaccharide or polysaccharide selected from the *Staphylococcus aureus* CP5 or CP8 gene cluster. In a specific embodiment, the glycosyltransferases for synthesis of the repeat units of an oligosaccharide or polysaccharide are from the *Staphylococcus aureus* CP5 gene cluster. *S. aureus* CP5 and CP8 have a similar structure to *P. aeruginosa* O11 antigen synthetic genes, so these genes may be combined with *E. coli* monosaccharide synthesis genes to synthesise an undecaprenyl pyrophosphate-linked CP5 or CP8 polymer consisting of repeating trisaccharide units.

In an embodiment, a host cell of the invention comprises glycosyltransferases sufficient for synthesis of the repeat units of the CP5 or CP8 saccharide comprising capH, cap, capJ and/or capK from *S. aureus* CP5 or CP8. Optionally the host cell of the invention also comprises capD, capE, capF, capG, capL, capM, capN, capO, capP from *S. aureus* CP5 or CP8. Alternatively, the host cell of the invention also comprises wbjB, wbjC, wbjD, wbjE, wbjF, wbjL, wbpM, wzz and/or wzx from *P. aeruginosa* O11 and wecB, wecC from *E. coli* O16.

In an embodiment, a host cell of the invention comprises glycosyltransferases sufficient for synthesis of the repeat units of the CP5 saccharide comprising capH, capI, capJ and/or capK from *S. aureus* CP5. Optionally the host cell of the invention also comprises capD, capE, capF, capG, capL, capM, capN, capO, capP from *S. aureus* CP5. Alternatively, the host cell of the invention also comprises wbjB, wbjC, wbjD, wbjE, wbjF, wbjL, wbpM, wzz and/or wzx from *P. aeruginosa* O11 and wecB, wecC from *E. coli* O16.

In an embodiment, a host cell of the invention comprises glycosyltransferases that assemble the donor oligosaccharide or polysaccharide repeat unit onto the hexose monosaccharide derivative comprise a glycosyltransferase that is capable of adding the hexose monosaccharide present at the reducing end of the first repeat unit of the donor oligosaccharide or polysaccharide to the hexose monosaccharide derivative.

Oligosaccharyl Transferases

N-linked protein glycosylation—the addition of carbohydrate molecules to an asparagine residue in the polypeptide chain of the target protein—is the most common type of post-translational modification occurring in the endoplasmic reticulum of eukaryotic organisms.

The process is accomplished by the enzymatic oligosaccharyltransferase complex (OST) responsible for the transfer of a preassembled oligosaccharide from a lipid carrier (dolichol phosphate) to an asparagine residue of a nascent protein within the conserved sequence Asn-X-Ser/Thr (where X is any amino acid except proline) in the Endoplasmic reticulum.

It has been shown that a bacterium, the food-borne pathogen *Campylobacter jejuni*, can also N-glycosylate its proteins (Wacker et al. Science. 2002; 298(5599):1790-3) due to the fact that it possesses its own glycosylation machinery. The machinery responsible of this reaction is encoded by a cluster called “pgl” (for protein glycosylation).

The *C. jejuni* glycosylation machinery can be transferred to *E. coli* to allow for the glycosylation of recombinant proteins expressed by the *E. coli* cells. Previous studies have demonstrated how to generate *E. coli* strains that can perform N-glycosylation (see, e.g. Wacker et al. *Science.* 2002; 298 (5599):1790-3; Nita-Lazar et al. *Glycobiology.* 2005; 15(4):361-7; Feldman et al. *Proc Natl Acad Sci USA.* 2005; 102(8):3016-21; Kowarik et al. *EMBO J.* 2006; 25(9):1957-66; Wacker et al. *Proc Natl Acad Sci USA.* 2006; 103(18):7088-93; International Patent Application Publication Nos. WO2003/074687, WO2006/119987, WO 2009/104074, and WO/2011/06261, and WO2011/138361). PgIB mutants having optimised properties are described in WO2016/107818. A preferred mutant is $PgIB_{cuo\ N311V\text{-}K482R\text{-}D483H\text{-}A669V}$, as described in the Examples.

Oligosaccharyl transferases transfer lipid-linked oligosaccharides to asparagine residues of nascent polypeptide chains that comprise a N-glycosylation consensus motif, e.g. Asn-X-Ser(Thr), wherein X can be any amino acid except Pro; or Asp(Glu)-X-Asn-Z-Ser(Thr), wherein X and Z are independently selected from any natural amino acid except Pro (see WO 2006/119987). See, e.g. WO 2003/074687 and WO 2006/119987, the disclosures of which are herein incorporated by reference in their entirety.

In an embodiment, the host cells of the invention comprise a nucleic acid that encodes an oligosaccharyl transferase. The nucleic acid that encodes an oligosaccharyl transferase can be native to the host cell, or can be introduced into the host cell using genetic approaches, as described above. In a specific embodiment, the oligosaccharyl transferase is an oligosaccharyl transferase from *Campylobacter*. In another specific embodiment, the oligosaccharyl transferase is an oligosaccharyl transferase from *Campylobacter jejuni* (i.e. pglB; see, e.g. Wacker et al. 2002, Science 298:1790-1793; see also, e.g. NCBI Gene ID: 3231775, UniProt Accession No. 086154). In another specific embodiment, the oligosaccharyl transferase is an oligosaccharyl transferase from *Campylobacter lari* (see, e.g. NCBI Gene ID: 7410986).

In a specific embodiment, the host cells of the invention comprise a nucleic acid sequence encoding an oligosaccharyl transferase, wherein said nucleic acid sequence encoding an oligosaccharyl transferase (e.g. pglB from *Campylobacter jejuni*) is integrated into the genome of the host cell.

In a specific embodiment, the host cells of the invention comprise a nucleic acid sequence encoding an oligosaccharyl transferase, wherein said nucleic acid sequence encoding an oligosaccharyl transferase (e.g. pglB from *Campylobacter jejuni*) is plasmid-borne.

In another specific embodiment, provided herein is a modified prokaryotic host cell comprising (i) a glycosyltransferase derived from an capsular polysaccharide cluster from *S. aureus*, wherein said glycosyltransferase is integrated into the genome of said host cell; (ii) a nucleic acid encoding an oligosaccharyl transferase (e.g. pglB from *Campylobacter jejuni*), wherein said nucleic acid encoding an oligosaccharyl transferase is plasmid-borne and/or integrated into the genome of the host cell; and (iii) a modified HIa protein of the invention, wherein said modified HIa protein is either plasmid-borne or integrated into the genome of the host cell. There is also provided a method of making a modified prokaryotic host cell comprising (i) integrating a glycosyltransferase derived from an capsular polysaccharide cluster from *S. aureus* into the genome of said host cell; (ii) integrating into the host cell one or more nucleic acids encoding an oligosaccharyl transferase (e.g. pglB from *Campylobacter jejuni*) which is plasmid-borne and/or integrated into the genome of the host cell; and (iii) integrating into a host cell a modified HIa protein of the invention either plasmid-borne or integrated into the genome of the host cell.

In specific embodiment is a host cell of the invention, wherein at least one gene of the host cell has been functionally inactivated or deleted, optionally wherein the waaL gene of the host cell has been functionally inactivated or deleted, optionally wherein the waaL gene of the host cell has been replaced by a nucleic acid encoding an oligosaccharyltransferase, optionally wherein the waaL gene of the host cell has been replaced by *C. jejuni* pglB.

Polymerases

In an embodiment, a polymerase (e.g. wzy) is introduced into a host cell of the invention (i.e. the polymerase is heterologous to the host cell). In an embodiment, the polymerase is a bacterial polymerase. In an embodiment, the polymerase is a capsular polysaccharide polymerase (e.g.

wzy) or an O antigen polymerase (e.g. wzy). In an embodiment, the polymerase is a capsular polysaccharide polymerase (e.g. wzy).

In an embodiment, a polymerase of a capsular polysaccharide biosynthetic pathway is introduced into a host cell of the invention.

In another specific embodiment, a polymerase of a capsular polysaccharide biosynthetic pathway of *Staphylococcus aureus* is introduced into a host cell of the invention.

In an embodiment, the polymerase introduced into the host cells of the invention is the wzy gene from a capsular polysaccharide gene cluster of *S. aureus* CP5 or CP8 (cap5J/cap8/). In a specific embodiment, the polymerase introduced into the host cells of the invention is the wzy gene from a capsular polysaccharide gene cluster of CP5 (cap5J).

In another specific embodiment, said polymerase is incorporated (e.g. inserted into the genome of or plasmid expressed by) in said host cell as part of a *S. aureus* capsular polysaccharide cluster, wherein said *S. aureus* capsular polysaccharide cluster has been modified to comprise the wzy polymerase.

In a specific embodiment, a nucleic acid sequence encoding the *S. aureus* wzy polymerase is inserted into or expressed by the host cells of the invention. Thus, a host cell of the invention may further comprise an *S. aureus* wzy polymerase.

Flippases

In an embodiment, a flippase (wzx or homologue) is introduced into a host cell of the invention (i.e. the flippase is heterologous to the host cell). Thus, a host cell of the invention may further comprise a flippase. In an embodiment, the flippase is a bacterial flippase. Flippases translocate wild type repeating units and/or their corresponding engineered (hybrid) repeat units from the cytoplasm into the periplam of host cells (e.g. *E. coli*). Thus, a host cell of the invention may comprise a nucleic acid that encodes a flippase (wzx).

In a specific embodiment, a flippase of a capsular polysaccharide biosynthetic pathway is introduced into a host cell of the invention.

In another specific embodiment, a flippase of a capsular polysaccharide biosynthetic pathway of *S. aureus* is introduced into a host cell of the invention. In certain embodiments, the flippase introduced into the host cells of the invention is the capK gene from a capsular polysaccharide gene cluster of *S. aureus* CP5 or CP8. In a specific embodiment, the flippase introduced into the host cells of the invention is the capK gene from a capsular polysaccharide gene cluster of CP5.

Other flippases that can be introduced into the host cells of the invention are for example from *Campylobacter jejuni* (e.g. pglK).

Enzymes That Modify Monosaccharides

Accessory Enzymes

In an embodiment, nucleic acids encoding one or more accessory enzymes are introduced into the host cells of the invention. Thus, a host cell of the invention may further comprise one or more of these accessory enzymes. Such nucleic acids encoding one or more accessory enzymes can be either plasmid-borne or integrated into the genome of the host cells of the invention. Exemplary accessory enzymes include, without limitation, epimerases, branching, modifying (e.g. to add cholins, glycerolphosphates, pyruvates), amidating, chain length regulating, acetylating, formylating, polymerizing enzymes.

In certain embodiments, enzymes that are capable of modifying monosaccharides are introduced into a host cell of the invention (i.e. the enzymes that are capable of modifying monosaccharides are heterologous to the host cell). Such enzymes include, e.g. epimerases and racemases. Thus, a host cell of the invention may further comprise an epimerase and/or racemase.

In an embodiment, the epimerases and racemases are from bacteria. In certain embodiments, the epimerases and/or racemases introduced into the host cells of the invention are from *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species.

In certain embodiments, the epimerase inserted into a host cell of the invention is an epimerase described in International Patent Application Publication No. WO2011/062615, the disclosure of which is incorporated by reference herein in its entirety. In one embodiment, the epimerase is the epimerase encoded by the Z3206 gene of *E. coli* strain 0157. See, e.g. WO 2011/062615 and Rush et al. 2009, The Journal of Biological Chemistry 285:1671-1680, which is incorporated by reference herein in its entirety. In another embodiment, the epimerase is galE (UPD-Galactose epimerase) Z3206 and galE convert GlcNAc-P-P-undecaprenyl to GalNAc-P-P-undecaprenyl. In a specific embodiment, the host cells of the invention comprise a nucleic acid sequence encoding an epimerase, wherein said nucleic acid sequence encoding an epimerase is integrated into the genome of the host cell.

In an embodiment, a host cell of the invention further comprises a mutase, for example glf (UDP-galactopyranose mutase).

In an embodiment, a host cell of the invention further comprises RcsA (an activator of CP synthesis). RcsA is an unstable positive regulator required for the synthesis of colanic acid capsular polysaccharide in *Escherichia coli*.

Genetic Background

Exemplary host cells that can be used to generate the host cells of the invention include, without limitation, *Escherichia* species, *Shigella* species, *Klebsiella* species, *Xhantomonas* species, *Salmonella* species, *Yersinia* species, *Lactococcus* species, *Lactobacillus* species, *Pseudomonas* species, *Corynebacterium* species, *Streptomyces* species, *Streptococcus* species, *Staphylococcus* species, *Bacillus* species, and *Clostridium* species. In a specific embodiment, the host cell used herein is *E. coli*.

In an embodiment, the host cell genetic background is modified by, e.g. deletion of one or more genes. Exemplary genes that can be deleted in host cells (and, in some cases, replaced with other desired nucleic acid sequences) include genes of host cells involved in glycolipid biosynthesis, such as waaL (see, e.g. Feldman et al. 2005, PNAS USA 102:3016-3021), the 0 antigen cluster (rfb or wb), enterobacterial common antigen cluster (wec), the lipid A core biosynthesis cluster (waa), and prophage 0 antigen modification clusters like the gtrABS cluster. In a specific embodiment, one or more of the waaL gene, gtrA gene, gtrB gene, gtrS gene, or a gene or genes from the wec cluster or a gene or genes from the rfb gene cluster are deleted or functionally inactivated from the genome of a prokaryotic host cell of the invention. In one embodiment, a host cell used herein is *E. coli*, wherein the waaL gene, gtrA gene, gtrB gene, gtrS gene are deleted or functionally inactivated from the genome of the host cell. In another embodiment, a host cell used herein is *E. coli*, wherein the waaL gene and gtrS gene are deleted or functionally inactivated from the genome of the host cell. In another embodiment, a host cell used herein is *E. coli*, wherein the waaL gene and genes from the wec cluster are deleted or functionally inactivated from the genome of the host cell.

Bioconjugates

The host cells of the invention can be used to produce bioconjugates comprising a saccharide antigen, for example a *Staphylococcus aureus* saccharide antigen linked to a modified HIa protein of the invention. Methods of producing bioconjugates using host cells are described for example in WO 2003/074687, WO 2006/119987 and WO2011/138361. Bioconjugates, as described herein, have advantageous properties over chemical conjugates of antigen-carrier protein, in that they require less chemicals in manufacture and are more consistent in terms of the final product generated.

In an embodiment, provided herein is a bioconjugate comprising a modified HIa protein linked to a *Staphylococcus aureus* antigen. In a specific embodiment, said *Staphylococcus aureus* antigen is a capsular saccharide (e.g. capsular polysaccharide). In a specific embodiment, provided herein is a bioconjugate comprising a modified HIa protein of the invention and an antigen selected from a capsular saccharide (e.g. capsular polysaccharide) of *Staphylococcus aureus* serotype CP5 or CP8. In a specific embodiment, provided herein is a bioconjugate comprising a modified HIa protein of the invention and an antigen from a capsular saccharide (e.g. capsular polysaccharide) of *Staphylococcus aureus* serotype CP5.

The bioconjugates of the invention can be purified for example, by chromatography (e.g. ion exchange, cationic exchange, anionic exchange, affinity, and sizing column chromatography), centrifugation, differential solubility, or by any other standard technique for the purification of proteins. See, e.g. Saraswat et al. 2013, Biomed. Res. Int. ID #312709 (p. 1-18); see also the methods described in WO 2009/104074. Further, the bioconjugates may be fused to heterologous polypeptide sequences described herein or otherwise known in the art to facilitate purification. For example, the HIa protein may incorporate a peptide tag such as a hexahistidine tag or HRHR tag (e.g. SEQ ID NOs: 25 and 26) for purification by cationic exchange. The actual conditions used to purify a particular bioconjugate will depend, in part, on the synthesis strategy and on factors such as net charge, hydrophobicity, and/or hydrophilicity of the bioconjugate, and will be apparent to those having skill in the art.

A further aspect of the invention is a process for producing a bioconjugate that comprises (or consists of) a modified HIa protein linked to a saccharide, said method comprising (i) culturing the host cell of the invention under conditions suitable for the production of proteins (and optionally under conditions suitable for the production of saccharides) and (ii) isolating the bioconjugate produced by said host cell.

A further aspect of the invention is a bioconjugate produced by the process of the invention, wherein said bioconjugate comprises a saccharide linked to a modified HIa protein.

Analytical Methods

Various methods can be used to analyze the structural compositions and sugar chain lengths of the bioconjugates of the invention.

In one embodiment, hydrazinolysis can be used to analyze glycans. First, polysaccharides are released from their protein carriers by incubation with hydrazine according to the manufacturer's instructions (Ludger Liberate Hydrazinolysis Glycan Release Kit, Oxfordshire, UK). The nucleophile hydrazine attacks the glycosidic bond between the polysaccharide and the carrier protein and allows release of the attached glycans. N-acetyl groups are lost during this treatment and have to be reconstituted by re-N-acetylation. The free glycans are purified on carbon columns and subsequently labeled at the reducing end with the fluorophor 2-amino benzamide. See Bigge J C, Patel T P, Bruce J A, Goulding P N, Charles S M, Parekh R B: Nonselective and efficient fluorescent labeling of glycans using 2-amino benzamide and anthranilic acid. Anal Biochem 1995, 230(2): 229-238. The labeled polysaccharides are separated on a GlycoSep-N column (GL Sciences) according to the HPLC protocol of Royle et al. See Royle L, Mattu T S, Hart E, Langridge J I, Merry A H, Murphy N, Harvey D J, Dwek R A, Rudd P M: An analytical and structural database provides a strategy for sequencing O-glycans from microgram quantities of glycoproteins. Anal Biochem 2002, 304(1):70-90. The resulting fluorescence chromatogram indicates the polysaccharide length and number of repeating units. Structural information can be gathered by collecting individual peaks and subsequently performing MS/MS analysis. Thereby the monosaccharide composition and sequence of the repeating unit could be confirmed and additionally in homogeneity of the polysaccharide composition could be identified.

In another embodiment, SDS-PAGE or capillary gel electrophoresis can be used to assess glycans and bioconjugates. Polymer length for the O antigen glycans is defined by the number of repeat units that are linearly assembled. This means that the typical ladder like pattern is a consequence of different repeat unit numbers that compose the glycan. Thus, two bands next to each other in SDS PAGE or other techniques that separate by size differ by only a single repeat unit. These discrete differences are exploited when analyzing glycoproteins for glycan size: The unglycosylated carrier protein and the bioconjugate with different polymer chain lengths separate according to their electrophoretic mobilities. The first detectable repeating unit number (n) and the average repeating unit number ($n_{average}$) present on a bioconjugate are measured. These parameters can be used to demonstrate batch to batch consistency or polysaccharide stability.

In another embodiment, high mass MS and size exclusion HPLC could be applied to measure the size of the complete bioconjugates.

In another embodiment, an anthrone-sulfuric acid assay can be used to measure polysaccharide yields. See Leyva A, Quintana A, Sanchez M, Rodriguez E N, Cremata J, Sanchez J C: Rapid and sensitive anthrone-sulfuric acid assay in microplate format to quantify carbohydrate in biopharmaceutical products: method development and validation. Biologicals: journal of the International Association of Biological Standardization 2008, 36(2):134-141. In another embodiment, a Methylpentose assay can be used to measure polysaccharide yields. See, e.g. Dische et al. J Biol Chem. 1948 September; 175(2):595-603.

Change in Glycosylation Site Usage

To show that the site usage in a specific protein is changed in a multiple plasmid system as opposed to an inserted system, the glycosylation site usage must be quantified. Methods to do so are listed below.

Glycopeptide LC-MS/MS: bioconjugates are digested with protease(s), and the peptides are separated by a suitable chromatographic method (C18, Hydrophilic interaction HPLC HILIC, GlycoSepN columns, SE HPLC, AE HPLC), and the different peptides are identified using MS/MS. This method can be used with our without previous sugar chain shortening by chemical (smith degradation) or enzymatic methods. Quantification of glycopeptide peaks using UV detection at 215 to 280 nm allow relative determination of glycosylation site usage.

Size exclusion HPLC: Higher glycosylation site usage is reflected by an earlier elution time from a SE HPLC column.

Homogeneity

Bioconjugate homogeneity (i.e. the homogeneity of the attached sugar residues) can be assessed using methods that measure glycan length and hydrodynamic radius.

Analytical Methods

Yield. Protein yield is measured as protein amount derived from a litre of bacterial production culture grown in a bioreactor under controlled and optimized conditions. Protein amount may be determined by BC, Lowry or Bradford assays. Yield of bioconjugate is measured as carbohydrate amount derived from a litre of bacterial production culture grown in a bioreactor under controlled and optimized conditions. After purification of bioconjugate, the carbohydrate yields can be directly measured by either the anthrone assay or ELISA using carbohydrate specific antisera. Indirect measurements are possible by using the protein amount (measured by BCA, Lowry, or Bradford assays) and the glycan length and structure to calculate a theoretical carbohydrate amount per gram of protein. In addition, yield can also be measured by drying the glycoprotein preparation from a volatile buffer and using a balance to measure the weight.

Aggregate formation The formation of high MW aggregates can be assessed by Western blot and, more quantitatively, by chromatographic techniques such as immobilised metal ion affinity chromatography (IMAC) and size exclusion chromatography. Aggregates are visible on Western blot as a high MW smear near the top of the gel. Aggregates may be visible on a chromatographic elution profile as a separate peak distinct from the peak corresponding to monomeric HIa.

Monomer yield: Similarly, the yield of monomers (or monomers versus aggregates) may be assessed by Western blot or, more accurately, via chromatographic techniques such as IMAC and size exclusion chromatography. The intensity of the bands corresponding to monomeric HIa on the Western blot, or the size of the peak corresponding to monomeric HIa in the chromatographic elution profile, Homogeneity. Homogeneity means the variability of glycan length and possibly the number of glycosylation sites. Methods listed above can be used for this purpose. SE-HPLC allows the measurement of the hydrodynamic radius. Higher numbers of glycosylation sites in the carrier lead to higher variation in hydrodynamic radius compared to a carrier with less glycosylation sites. However, when single glycan chains are analyzed, they may be more homogenous due to the more controlled length. Glycan length is measured by hydrazinolysis, SDS PAGE, and CGE. In addition, homogeneity can also mean that certain glycosylation site usage patterns change to a broader/narrower range. These factors can be measured by Glycopeptide LC-MS/MS.

Strain stability and reproducibility. Strain stability during bacterial fermentation in absence of selective pressure is measured by direct and indirect methods that confirm presence or absence of the recombinant DNA in production culture cells. Culture volume influence can be simulated by elongated culturing times meaning increased generation times. The more generations in fermentation, the more it is likely that a recombinant element is lost. Loss of a recombinant element is considered instability. Indirect methods rely on the association of selection cassettes with recombinant DNA, e.g. the antibiotic resistance cassettes in a plasmid. Production culture cells are plated on selective media, e.g. LB plates supplemented with antibiotics or other chemicals related to a selection system, and resistant colonies are considered as positive for the recombinant DNA associated to the respective selection chemical. In the case of a multiple plasmid system, resistant colonies to multiple antibiotics are counted and the proportion of cells containing all three resistances is considered the stable population. Alternatively, quantitative PCR can be used to measure the amount of recombinant DNA of the three recombinant elements in the presence, absence of selection, and at different time points of fermentation. Thus, the relative and absolute amount of recombinant DNA is measured and compared. Reproducibility of the production process is measured by the complete analysis of consistency batches by the methods stated in this application.

Immunogenic Compositions

The modified HIa proteins and conjugates (e.g. bioconjugate), of the invention are particularly suited for inclusion in immunogenic compositions and vaccines. The present invention provides an immunogenic composition comprising the modified HIa protein of the invention, or the conjugate of the invention, or the bioconjugate of the invention.

Also provided is a method of making the immunogenic composition of the invention comprising the step of mixing the modified HIa protein or the conjugate (e.g. bioconjugate) of the invention with a pharmaceutically acceptable excipient or carrier.

Immunogenic compositions comprise an immunologically effective amount of the modified HIa protein or conjugate (e.g. bioconjugate) of the invention, as well as any other components. By "immunologically effective amount", it is meant that the administration of that amount to an individual, either as a single dose or as part of a series is effective for treatment or prevention. This amount varies depending on the health and physical condition of the individual to be treated, age, the degree of protection desired, the formulation of the vaccine and other relevant factors. It is expected that the amount will fall in a relatively broad range that can be determined through routine trials.

Immunogenic compositions if the invention may also contain diluents such as water, saline, glycerol etc. Additionally, auxiliary substances, such as wetting or emulsifying agents, pH buffering substances, polyols and the like may be present.

The immunogenic compositions comprising the modified HIa protein of the invention or conjugates (or bioconjugates) may comprise any additional components suitable for use in pharmaceutical administration. In specific embodiments, the immunogenic compositions of the invention are monovalent formulations. In other embodiments, the immunogenic compositions of the invention are multivalent formulations, e.g. bivalent, trivalent, and tetravalent formulations. For example, a multivalent formulation comprises more than one antigen for example more than one conjugate.

The immunogenic composition of the invention optionally further comprise additional antigens. Examples of such additional antigens are *S aureus* proteins or capsular polysaccharides.

Vaccines

The present invention also provides a vaccine comprising an immunogenic composition of the invention and a pharmaceutically acceptable excipient or carrier.

Pharmaceutically acceptable excipients and carriers can be selected by those of skill in the art. For example, the pharmaceutically acceptable excipient or carrier can include a buffer, such as Tris (trimethamine), phosphate (e.g. sodium phosphate), acetate, borate (e.g. sodium borate), citrate, glycine, histidine and succinate (e.g. sodium succinate), suitably sodium chloride, histidine, sodium phosphate or sodium succinate. The pharmaceutically acceptable excipient may include a salt, for example sodium chloride, potassium chloride or magnesium chloride. Optionally, the pharmaceutically acceptable excipient contains at least one component that stabilizes solubility and/or stability. Examples of solubilizing/stabilizing agents include detergents, for example, laurel sarcosine and/or polysorbate (e.g. TWEEN™ 80). Examples of stabilizing agents also include poloxamer (e.g. poloxamer 124, poloxamer 188, poloxamer 237, poloxamer 338 and poloxamer 407). The pharmaceutically acceptable excipient may include a non-ionic surfactant, for example polyoxyethylene sorbitan fatty acid esters, Polysorbate-80 (TWEEN™ 80), Polysorbate-60 (TWEEN™ 60), Polysorbate-40 (TWEEN™ 40) and Polysorbate-20 (TWEEN™ 20), or polyoxyethylene alkyl ethers (suitably polysorbate-80). Alternative solubilizing/stabilizing agents include arginine, and glass forming polyols (such as sucrose, trehalose and the like). The pharmaceutically excipient may be a preservative, for example phenol, 2-phenoxyethanol, or thiomersal. Other pharmaceutically acceptable excipients include sugars (e.g. lactose, sucrose), and proteins (e.g. gelatine and albumin). Pharmaceutically acceptable carriers include water, saline solutions, aqueous dextrose and glycerol solutions. Numerous pharmaceutically acceptable excipients and carriers are described, for example, in Remington's Pharmaceutical Sciences, by E. W. Martin, Mack Publishing Co. Easton, Pa., 5th Edition (975).

In an embodiment, the immunogenic composition or vaccine of the invention additionally comprises one or more buffers, e.g. phosphate buffer and/or sucrose phosphate glutamate buffer. In other embodiments, the immunogenic composition or vaccine of the invention does not comprise a buffer.

In an embodiment, the immunogenic composition or vaccine of the invention additionally comprises one or more salts, e.g. sodium chloride, calcium chloride, sodium phosphate, monosodium glutamate, and aluminum salts (e.g. aluminum hydroxide, aluminum phosphate, alum (potassium aluminum sulfate), or a mixture of such aluminum salts). In other embodiments, the immunogenic composition or vaccine of the invention does not comprise a salt.

The immunogenic composition or vaccine of the invention may additionally comprise a preservative, e.g. a mercury derivative thimerosal. In a specific embodiment, the immunogenic composition or vaccine of the invention comprises 0.001% to 0.01% thimerosal. In other embodiments, the immunogenic composition or vaccine of the invention do not comprise a preservative.

The vaccine or immunogenic composition of the invention may also comprise an antimicrobial, typically when package in multiple dose format. For example, the immunogenic composition or vaccine of the invention may comprise 2-phenoxyethanol.

The vaccine or immunogenic composition of the invention may also comprise a detergent e.g. polysorbate, such as TWEEN™ 80. Detergents are generally present at low levels e.g. <0.01%, but higher levels have been suggested for stabilising antigen formulations e.g. up to 10%.

The immunogenic compositions of the invention can be included in a container, pack, or dispenser together with instructions for administration.

The immunogenic compositions or vaccines of the invention can be stored before use, e.g. the compositions can be stored frozen (e.g. at about −20° C. or at about −70° C.); stored in refrigerated conditions (e.g. at about 4° C.); or stored at room temperature.

The immunogenic compositions or vaccines of the invention may be stored in solution or lyophilized. In an embodiment, the solution is lyophilized in the presence of a sugar such as sucrose, trehalose or lactose. In another embodiment, the vaccines of the invention are lyophilized and extemporaneously reconstituted prior to use.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

Adjuvants

In an embodiment, the immunogenic compositions or vaccines of the invention comprise, or are administered in combination with, an adjuvant. The adjuvant for administration in combination with an immunogenic composition or vaccine of the invention may be administered before, concomitantly with, or after administration of said immunogenic composition or vaccine. In some embodiments, the term "adjuvant" refers to a compound that when administered in conjunction with or as part of an immunogenic composition of vaccine of the invention augments, enhances and/or boosts the immune response to a bioconjugate, but when the compound is administered alone does not generate an immune response to the modified HIa protein/conjugate/bioconjugate. In some embodiments, the adjuvant generates an immune response to the modified HIa protein, conjugate or bioconjugate and does not produce an allergy or other adverse reaction.

In an embodiment, the immunogenic composition or vaccine of the invention is adjuvanted. Adjuvants can enhance an immune response by several mechanisms including, e.g. lymphocyte recruitment, stimulation of B and/or T cells, and stimulation of macrophages. Specific examples of adjuvants include, but are not limited to, aluminum salts (alum) (such as aluminum hydroxide, aluminum phosphate, and aluminum sulfate), 3 De-O-acylated monophosphoryl lipid A (MPL) (see United Kingdom Patent GB2220211), MF59 (Novartis), AS01 (GlaxoSmithKline), AS03 (GlaxoSmithKline), AS04 (GlaxoSmithKline), polysorbate 80 (TWEEN™ 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO2007/109813) and saponins, such as QS21 (see Kensil et al. in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). Other adjuvants are oil in water emulsions (such as squalene or peanut oil), optionally in combination with immune stimulants, such as monophosphoryl lipid A (see Stoute et al. N. Engl. J. Med. 336, 86-91 (1997)). Another adjuvant is CpG (Bioworld Today, Nov. 15, 1998).

In one aspect of the invention, the adjuvant is an aluminum salt such as aluminum hydroxide gel (alum) or aluminium phosphate.

In another aspect of the invention, the adjuvant is selected to be a preferential inducer of either a TH1 or a TH2 type of response. High levels of Th1-type cytokines tend to favor the induction of cell mediated immune responses to a given antigen, whilst high levels of Th2-type cytokines tend to favour the induction of humoral immune responses to the antigen. It is important to remember that the distinction of Th1 and Th2-type immune response is not absolute. In reality an individual will support an immune response which is described as being predominantly Th1 or predominantly Th2. However, it is often convenient to consider the families of cytokines in terms of that described in murine CD4 +ve T cell clones by Mosmann and Coffman (Mosmann, T. R. and Coffman, R. L. (1989) TH1 and TH2 cells: different patterns of lymphokine secretion lead to different functional properties. Annual Review of Immunology, 7, p 145-173). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of Il-4, IL-5, IL-6, IL-10. Suitable adjuvant systems which promote a predominantly Th1 response include: Monophosphoryl lipid A or a derivative thereof, particularly 3-de-O-acylated monophosphoryl lipid A (3D-MPL) (for its preparation see GB 2220211 A); MPL, e.g. 3D-MPL and the saponin QS21 in a liposome, for example a liposome comprising cholesterol and DPOC; and a combination of monophosphoryl lipid A, for example 3-de-O-acylated monophosphoryl lipid A, together with either an aluminium salt (for instance aluminium phosphate or aluminium hydroxide) or an oil-in-water emulsion. In such combinations, antigen and 3D-MPL are contained in the same particulate structures, allowing for more efficient delivery of antigenic and immunostimulatory signals. Studies have shown that 3D-MPL is able to further enhance the immunogenicity of an alum-adsorbed antigen [Thoelen et al. Vaccine (1998) 16:708-14; EP 689454-B1]. Unmethylated CpG containing oligonucleotides (WO 96/02555) are also preferential inducers of a TH1 response and are suitable for use in the present invention.

The vaccine or immunogenic composition of the invention may contain an oil in water emulsion, since these have been suggested to be useful as adjuvant compositions (EP 399843; WO 95/17210). Oil in water emulsions such as those described in WO95/17210 (which discloses oil in water emulsions comprising from 2 to 10% squalene, from 2 to 10% alpha tocopherol and from 0.3 to 3% tween 80 and their use alone or in combination with QS21 and/or 3D-MPL), WO99/12565 (which discloses oil in water emulsion compositions comprising a metabolisable oil, a saponin and a sterol and MPL) or WO99/11241 may be used. Further oil in water emulsions such as those disclosed in WO 09/127676 and WO 09/127677 are also suitable. In a specific embodiment, the immunogenic composition or vaccine additionally comprises a saponin, for example QS21. The immunogenic composition or vaccine may also comprise an oil in water emulsion and tocopherol (WO 95/17210).

Method of Administration

Immunogenic compositions or vaccines of the invention may be used to protect or treat a mammal susceptible to infection, by means of administering said immunogenic composition or vaccine via systemic or mucosal route. These administrations may include injection via the intramuscular (IM), intraperitoneal, intradermal (ID) or subcutaneous routes; or via mucosal administration to the oral/alimentary, respiratory, genitourinary tracts. For example, intranasal (IN) administration may be used for the treatment of pneumonia or otitis media (as nasopharyngeal carriage of pneumococci can be more effectively prevented, thus attenuating infection at its earliest stage). Although the immunogenic composition or vaccine of the invention may be administered as a single dose, components thereof may also be co-administered together at the same time or at different times (for instance pneumococcal polysaccharides could be administered separately, at the same time or 1-2 weeks after the administration of any bacterial protein component of the vaccine for optimal coordination of the immune responses with respect to each other). For co-administration, the optional Th1 adjuvant may be present in any or all of the different administrations, however in one particular aspect of the invention it is present in combination with the modified HIa protein component of the immunogenic composition or vaccine. In addition to a single route of administration, 2 different routes of administration may be used. For example, polysaccharides may be administered IM (or ID) and bacterial proteins may be administered IN (or ID). In addition, the vaccines of the invention may be administered IM for priming doses and IN for booster doses.

In one aspect, the immunogenic composition or vaccine of the invention is administered by the intramuscular delivery route. Intramuscular administration may be to the thigh or the upper arm. Injection is typically via a needle (e.g. a hypodermic needle), but needle-free injection may alternatively be used. A typical intramuscular dose is 0.5 ml.

In another aspect, the immunogenic composition or vaccine of the invention is administered by the intradermal administration. Human skin comprises an outer "horny" cuticle, called the stratum corneum, which overlays the epidermis. Underneath this epidermis is a layer called the dermis, which in turn overlays the subcutaneous tissue. The conventional technique of intradermal injection, the "mantoux procedure", comprises steps of cleaning the skin, and then stretching with one hand, and with the bevel of a narrow gauge needle (26 to 31 gauge) facing upwards the needle is inserted at an angle of between 10 to 15°. Once the bevel of the needle is inserted, the barrel of the needle is lowered and further advanced whilst providing a slight pressure to elevate it under the skin. The liquid is then injected very slowly thereby forming a bleb or bump on the skin surface, followed by slow withdrawal of the needle.

More recently, devices that are specifically designed to administer liquid agents into or across the skin have been described, for example the devices described in WO 99/34850 and EP 1092444, also the jet injection devices described for example in WO 01/13977; U.S. Pat. Nos. 5,480,381, 5,599,302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Alternative methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

In another aspect, the immunogenic composition or vaccine of the invention is administered by the intranasal administration. Typically, the immunogenic composition or vaccine is administered locally to the nasopharyngeal area, e.g. without being inhaled into the lungs. It is desirable to use an intranasal delivery device which delivers the immunogenic composition or vaccine formulation to the nasopharyngeal area, without or substantially without it entering the lungs. Suitable devices for intranasal administration of the vaccines according to the invention are spray devices. Suitable commercially available nasal spray devices include ACCUSPRAY™ (Becton Dickinson).

In an embodiment, spray devices for intranasal use are devices for which the performance of the device is not dependent upon the pressure applied by the user. These devices are known as pressure threshold devices. Liquid is released from the nozzle only when a threshold pressure is applied. These devices make it easier to achieve a spray with a regular droplet size. Pressure threshold devices suitable for use with the present invention are known in the art and are described for example in WO91/13281 and EP311 863 and EP516636, incorporated herein by reference. Such devices are commercially available from Pfeiffer GmbH and are also described in Bommer, R. Pharmaceutical Technology Europe, September 1999.

In another embodiment, intranasal devices produce droplets (measured using water as the liquid) in the range 1 to 200 μm, e.g. 10 to 120 μm. Below 10 μm there is a risk of inhalation, therefore it is desirable to have no more than about 5% of droplets below 10 μm. Droplets above 120 μm do not spread as well as smaller droplets, so it is desirable to have no more than about 5% of droplets exceeding 120 μm.

Following an initial vaccination, subjects may receive one or several booster immunizations adequately spaced.

The immunogenic composition or vaccine of the present invention may be used to protect or treat a mammal, e.g. human, susceptible to infection, by means of administering said immunogenic composition or vaccine via a systemic or mucosal route. These administrations may include injection via the intramuscular (IM), intraperitoneal (IP), intradermal (ID) or subcutaneous (SC) routes; or via mucosal administration to the oral/alimentary, respiratory, genitourinary tracts. Although the vaccine of the invention may be administered as a single dose, components thereof may also be co-administered together at the same time or at different times (for instance pneumococcal saccharide conjugates could be administered separately, at the same time or 1-2 weeks after the administration of the any modified HIa protein, conjugate or bioconjugate of the invention for optimal coordination of the immune responses with respect to each other). For co-administration, the optional adjuvant may be present in any or all of the different administrations. In addition to a single route of administration, 2 different routes of administration may be used. For example, polysaccharide conjugates may be administered IM (or ID) and the modified HIa protein, conjugate or bioconjugate of the invention may be administered IN (or ID). In addition, the immunogenic compositions or vaccines of the invention may be administered IM for priming doses and IN for booster doses.

Dosage

The amount of conjugate antigen in each immunogenic composition or vaccine dose is selected as an amount which induces an immunoprotective response without significant, adverse side effects in typical vaccines. Such amount will vary depending upon which specific immunogen is employed and how it is presented. The content of modified HIa protein will typically be in the range 1-100 μg, suitably 5-50 μg. The content of saccharide will typically be in the range 0.1-10 μg, suitably 1-5 μg.

A dose which is in a volume suitable for human use is generally between 0.25 and 1.5 ml, although, for administration to the skin a lower volume of between 0.05 ml and 0.2 ml may be used. In one embodiment, a human dose is 0.5 ml. In a further embodiment, a human dose is higher than 0.5 ml, for example 0.6, 0.7, 0.8, 0.9 or 1 ml. In a further embodiment, a human dose is between 1 ml and 1.5 ml. In another embodiment, in particular when the immunogenic composition is for the pediatric population, a human dose may be less than 0.5 ml such as between 0.25 and 0.5 ml.

Prophylactic and Therapeutic Uses

The present invention also provides methods of treating and/or preventing bacterial infections of a subject comprising administering to the subject a modified HIa protein, conjugate or bioconjugate of the invention. The modified HIa protein, conjugate or bioconjugate may be in the form of an immunogenic composition or vaccine. In a specific embodiment, the immunogenic composition or vaccine of the invention is used in the prevention of infection of a subject (e.g. human subjects) by a bacterium. Bacterial infections that can be treated and/or prevented using the modified HIa protein, conjugate or bioconjugate of the invention include those caused by *Staphylococcus* species, *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Bacillus* species, *Clostridium* species, *Listeria* species, or *Campylobacter* species. In a specific embodiment, the immunogenic composition or vaccine of the invention is used to treat or prevent an infection by *Staphylococcus* species (e.g. *Staphylococcus aureus*).

Also provided herein are methods of inducing an immune response in a subject against a bacterium, comprising administering to the subject a modified HIa protein, or conjugate or bioconjugate of the invention (or immunogenic composition or vaccine). In one embodiment, said subject has bacterial infection at the time of administration. In another embodiment, said subject does not have a bacterial infection at the time of administration. The modified HIa protein, conjugate or bioconjugate of the invention can be used to induce an immune response against *Staphylococcus* species, *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Bacillus* species, *Clostridium* species, *Listeria* species, or *Campylobacter* species. In a specific embodiment, modified HIa protein, or conjugate or bioconjugate of the invention is used to induce an immune response against *Staphylococcus* species (e.g. *Staphylococcus aureus*).

Also provided herein are methods of inducing the production of opsonophagocytic antibodies in a subject against a bacterium, comprising administering to the subject a modified HIa protein, or conjugate or bioconjugate of the invention (or immunogenic composition or vaccine). In one embodiment, said subject has bacterial infection at the time of administration. In another embodiment, said subject does not have a bacterial infection at the time of administration. The modified HIa protein, or conjugate or bioconjugate of the invention (or immunogenic composition or vaccine) provided herein can be used to induce the production of opsonophagocytic antibodies against *Staphylococcus* species, *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Bacillus* species, *Clostridium* species, *Listeria* species, or *Campylobacter* species. In a specific embodiment, a modified HIa protein, or conjugate or bioconjugate of the invention (or immunogenic composition or vaccine) is used to induce the production of opsonophagocytic antibodies against *Staphylococcus* species (e.g. *Staphylococcus aureus*).

For example, the immunogenic composition or vaccine of the invention may be used to prevent against *S. aureus* infection, including a nosocomial infection. More particularly, the subject may be protected against a skin infection, pneumonia, meningitis, osteomyelitis endocarditis, toxic shock syndrome, and/or septicaemia. The invention is also useful for protecting against *S. aureus* infection of a subject's bones and joints (and thus for preventing disorders including, but not limited to, osteomyelitis, septic arthritis, and prosthetic joint infection). In many cases these disorders may be associated with the formation of a *S. aureus* biofilm.

*S. aureus* infects various mammals (including cows, dogs, horses, and pigs), but the preferred mammal for use with the invention is a human. The human can be a child (e.g. a toddler or infant), a teenager, or an adult. In some embodiments the human may have a prosthetic bone or joint, or may be a patient awaiting elective surgery, in particular an intended recipient of a prosthetic bone or joint (e.g. a pre-operative orthopedic surgery patient). The vaccines are not suitable solely for these groups, however, and may be used more generally in a human population.

The vaccine preparations of the present invention may be used to protect or treat a human susceptible to *S. aureus* infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts.

In an embodiment, the present invention is an improved method to elicit an immune response in infants (defined as 0-2 years old in the context of the present invention) by administering a therapeutically effective amount of an immunogenic composition or vaccine of the invention (a paediatric vaccine). In an embodiment, the vaccine is a paediatric vaccine.

In an embodiment, the present invention is an improved method to elicit an immune response in the elderly population (in the context of the present invention a patient is considered elderly if they are 50 years or over in age, typically over 55 years and more generally over 60 years) by administering a therapeutically effective amount of the immunogenic composition or vaccine of the invention. In an embodiment, the vaccine is a vaccine for the elderly.

The present invention provides a method for the treatment or prevention of *Staphylococcus aureus* infection in a subject in need thereof comprising administering to said subject a therapeutically effective amount of the modified HIa protein of the invention, or the conjugate of the invention, or the bioconjugate of the invention, or the immunogenic composition or vaccine of the invention.

The present invention provides a method of immunising a human host against *Staphylococcus aureus* infection comprising administering to the host an immunoprotective dose of the modified HIa protein of the invention, or the conjugate of the invention, or the bioconjugate of the invention, or the immunogenic composition or vaccine of the invention.

The present invention provides a method of inducing an immune response to *Staphylococcus aureus* in a subject, the method comprising administering a therapeutically or prophylactically effective amount of the modified HIa protein of the invention, or the conjugate of the invention, or the bioconjugate of the invention, or the immunogenic composition or vaccine of the invention.

The present invention provides a modified HIa protein of the invention, or the conjugate of the invention, or the bioconjugate of the invention, or the immunogenic composition or vaccine of the invention for use in the treatment or prevention of a disease caused by *Staphylococcus aureus* infection.

The present invention provides use of the modified HIa protein of the invention, or the conjugate of the invention, or the bioconjugate of the invention in the manufacture of a medicament for the treatment or prevention of a disease caused by *Staphylococcus aureus* infection.

The disease caused by *S aureus* infection may be, for example, a skin infection, pneumonia, meningitis, *S. aureus* infection of a subject's bones and joints (e.g. septic arthritis, prosthetic joint infection or osteomyelitis) endocarditis, toxic shock syndrome, and/or septicaemia. The disease may be a nosocomial infection.

All references or patent applications cited within this patent specification are incorporated by reference herein.

Aspects of the invention are summarised in the following numbered paragraphs:

1. A modified HIa protein having an amino acid sequence of SEQ ID NO. 1 or an amino acid sequence at least 80%, 85%, 90%, 92%, 95%, 96%, 97%, 98% or 99% identical to SEQ ID NO. 1, modified in that the amino acid sequence comprises amino acid substitutions at positions H48 and G122 of SEQ ID NO. 1 or at equivalent positions within an amino acid sequence at least 80%, 85%, 90%, 92%, 95%, 96%, 97%, 98% or 99% identical to SEQ ID NO. 1, wherein said substitutions are respectively H to C and G to C.
2. A modified HIa protein according to paragraph 1, further modified in that the amino acid sequence comprises an amino acid substitution at position H35 of SEQ ID NO. 1 or at an equivalent position within an amino acid sequence at least 80%, 85%, 90%, 92%, 95%, 96%, 97%, 98% or 99% identical to SEQ ID NO. 1.
3. A modified HIa protein according to paragraph 2, wherein said amino acid substitution at position H35 is H to L.
4. A modified HIa protein according to any one of paragraphs 1 to 3, further modified in that the amino acid sequence comprises one or more consensus sequence(s) selected from: D/E-X-N-Z-S/T (SEQ ID NO. 11) and K-D/E-X-N-Z-S/T-K (SEQ ID NO. 12), wherein X and Z are independently any amino acid apart from proline.
5. A modified HIa protein of paragraph 4, wherein one or more amino acids (e.g. 1-7 amino acids, e.g. one amino acid) of the amino acid sequence of SEQ ID NO. 1 or an amino acid sequence at least 80%, 85%, 90%, 92%, 95%, 96%, 97%, 98% or 99% identical to SEQ ID NO. 1 have been substituted by a D/E-X-N-Z-S/T (SEQ ID NO. 11) or K-D/E-X-N-Z-S/T-K (SEQ ID NO. 12) consensus sequence.
6. The modified HIa protein of any one of paragraphs 1-5, wherein a consensus sequence selected from D/E-X-N-Z-S/T (SEQ ID NO. 11) and K-D/E-X-N-Z-S/T-K (SEQ ID NO. 12) has been added at, or substituted for, one or more amino acids selected from K131, S203, S239 and K273 of SEQ ID NO. 1 or at an equivalent position within an amino acid sequence at least 80%, 85%, 90%, 92%, 95%, 96%, 97%, 98% or 99% identical to SEQ ID NO. 1.
7. The modified HIa protein of paragraph 6, wherein a consensus sequence selected from D/E-X-N-Z-S/T (SEQ ID NO. 11) and K-D/E-X-N-Z-S/T-K (SEQ ID NO. 12) has been added at, or substituted for, amino acid K131 of SEQ ID NO. 1 or at an equivalent position within an amino acid sequence at least 80%, 85%, 90%, 92%, 95%, 96%, 97%, 98% or 99% identical to SEQ ID NO. 1.

8. The modified HIa protein of paragraph 7, wherein a consensus sequence selected from D/E-X-N-Z-S/T (SEQ ID NO. 11) and K-D/E-X-N-Z-S/T-K (SEQ ID NO. 12) has been substituted for amino acid K131 of SEQ ID NO. 1 or at an equivalent position within an amino acid sequence at least 80%, 85%, 90%, 92%, 95%, 96%, 97%, 98% or 99% identical to SEQ ID NO. 1.

9. The modified HIa protein of any one of paragraphs 4 to 8, wherein said wherein X is Q (glutamine) and Z is R (arginine) (e.g. K-D-Q-N-R-T-K (SEQ ID NO: 23)).

10. The modified HIa protein of any one of paragraphs 1 to 9, which has the amino acid sequence of SEQ ID NO: 3 or an amino acid sequence which is at least 80%, 85%, 90%, 92%, 95%, 96%, 97%, 98%, 99% or 100% identical to the sequence of SEQ ID NO. 3.

11. The modified HIa protein of any one of paragraphs 1-10, wherein the amino acid sequence further comprises a peptide tag which is useful for the purification of the HIa protein, wherein said peptide tag optionally comprises six histidine residues or a HR repeat (e.g. HRHR (SEQ ID NO: 25) and optionally said peptide tag is located at the C-terminus of the amino acid sequence.

12. The modified HIa protein of paragraph 11, wherein the peptide tag additionally comprises one or two initial amino acids at the N-terminus, e.g. GS (SEQ ID NO: 26).

13. The modified HIa protein or paragraph 12, which has the amino acid sequence of any one of SEQ ID NO: 5, 6, 9 or 10 or a sequence at least 97%, 98%, 99% or 100% identical to any one of SEQ ID NO: 5, 6, 9 or 10.

14. The modified HIa protein of any one of paragraphs 1-13, wherein the amino acid sequence further comprises a signal sequence which is capable of directing the HIa protein to the periplasm of a host cell (e.g. bacterium), optionally said signal sequence being selected from SEQ ID NO. 13-21, optionally said sequence being at the N-terminus of the protein.

15. The modified HIa protein of paragraph 11, wherein the protein comprises an additional one or two amino acids (e.g. S) between the signal sequence and the amino acid sequence of SEQ ID NO 1 or amino acid sequence at least 80%, 85%, 90%, 92%, 95%, 96%, 97%, 98% or 99% identical to SEQ ID NO. 1, wherein optionally said HIa protein has the amino acid sequence of SEQ ID NO: 5 or SEQ ID NO: 9 or an amino acid sequence at least 97%, 98%, 99% or 100% identical to SEQ ID NO. 5 or SEQ ID NO. 9.

16. The modified HIa protein of any one of paragraphs 1-13, wherein the protein comprises an additional one or two amino acids (e.g. S) at the N-terminus.

17. The modified HIa protein of paragraph 16, wherein said HIa protein has the amino acid sequence of SEQ ID NO: 6 or SEQ ID NO: 10 or an amino acid sequence at least 97%, 98%, 99% or 100% identical to SEQ ID NO. 6 or SEQ ID NO. 10.

18. The modified HIa protein of any one of paragraphs 1-17, wherein the modified HIa protein is glycosylated.

19. A conjugate comprising a modified HIa protein of any one of paragraphs 1-18, wherein the modified HIa protein is linked to an antigen, e.g. a polysaccharide or oligosaccharide antigen.

20. The conjugate according to paragraph 19, wherein the modified HIa protein is covalently linked to said antigen through a chemical linkage obtainable using a chemical conjugation method, optionally selected from the group consisting of carbodiimide chemistry, reductive animation, cyanylation chemistry (for example CDAP chemistry), maleimide chemistry, hydrazide chemistry, ester chemistry, and N-hydroysuccinimide chemistry either directly or via a linker.

21. A conjugate according to paragraph 19, which is a bioconjugate.

22. The conjugate (e.g. bioconjugate) of any one of paragraphs 19 to 21, wherein the antigen is linked to an amino acid on the modified HIa protein selected from asparagine, aspartic acid, glutamic acid, lysine, cysteine, tyrosine, histidine, arginine or tryptophan (e.g. asparagine).

23. The conjugate (e.g. bioconjugate) of any one of paragraphs 15-17, wherein the antigen is a saccharide, optionally a bacterial capsular saccharide (e.g. from *Staphylococcus aureus*) optionally selected from a *S. aureus* serotype 5 or 8 capsular saccharide.

24. The conjugate (e.g. bioconjugate) of paragraph 23, wherein the antigen is a *Staphylococcus aureus* serotype 5 capsular saccharide.

25. A polynucleotide encoding the modified HIa protein of any one of paragraphs 1-17.

26. A vector comprising the polynucleotide of paragraph 25.

27. A host cell comprising:
   i) one or more nucleic acids that encode glycosyltransferase(s);
   ii) a nucleic acid that encodes an oligosaccharyl transferase;
   iii) a nucleic acid that encodes a modified HIa protein according to any one of paragraphs 1-17; and optionally
   iv) a nucleic acid that encodes a polymerase (e.g. wzy).

28. The host cell of paragraph 27, wherein said host cell comprises (a) a glycosyltransferase that assembles a hexose monosaccharide derivative onto undecaprenyl pyrophosphate (Und-PP) and (b) one or more glycosyltransferases capable of adding a monosaccharide to the hexose monosaccharide derivative assembled on Und-PP.

29. The host cell of paragraph 28, wherein said glycosyltransferase that assembles a hexose monosaccharide derivative onto Und-PP is heterologous to the host cell and/or heterologous to one or more of the genes that encode glycosyltransferase(s) optionally wherein said glycosyltransferase that assembles a hexose monosaccharide derivative onto Und-PP is from *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species, optionally wecA (e.g. wecA from *E. coli*).

30. The host cell of any one of paragraphs 27-29, wherein said hexose monosaccharide derivative is any monosaccharide in which C-2 position is modified with an acetamido group such as N-acetylglucosamine (GlcNAc), N-acetylgalactoseamine (GalNAc), 2,4-Diacetamido-2,4, 6-trideoxyhexose (DATDH). N-acetylfucoseamine (FucNAc), or N-acetylquinovosamine (QuiNAc).

31. The host cell of any one of paragraphs 27-30, wherein said one or more glycosyltransferases capable of adding a monosaccharide to the hexose monosaccharide derivative assembled on Und-PP is the galactofuranosyl transferase (wbeY) from *E. coli* O28 or the galactofuranosyl transferase (wfdK) from *E. coli* O167 or are the galactofuranosyl transferase (wbeY) from *E. coli* O28 and the galactofuranosyl transferase (wfdK) from *E. coli* O167.

32. The host cell of any one of paragraphs 27-31 wherein the host cell comprises glycosyltransferases sufficient for synthesis of repeat units of the *S. aureus* CP5 saccharide comprising capH, capI, capJ and/or capK from *S. aureus* CP5 and optionally capD, capE, capF, capG, capL, capM, capN, capO an/or capP from *S. aureus* CP5.

33. The host cell of any one of paragraphs 27-31 wherein the host cell comprises glycosyltransferases sufficient for synthesis repeat units of the *S. aureus* CP5 saccharide comprising capH, capI, capJ and/or capK from *S. aureus* CP5 and optionally wbjB, wbjC, wbjD, wbjE, wbjF, wbjL, wbpM, wzz and/or wzx from *P. aeruginosa* O11 and wecB and/or wecC from *E. coli* O16.

34. The host cell of any one of paragraphs 27-33 wherein the oligosaccharyl transferase is derived from *Campylobacter jejuni*, optionally wherein said oligosaccharyl transferase is pglB of *C. jejuni*, optionally wherein the pglB gene of *C. jejuni* is integrated into the host cell genome and optionally wherein at least one gene of the host cell has been functionally inactivated or deleted, optionally wherein the waaL gene of the host cell has been functionally inactivated or deleted, optionally wherein the waaL gene of the host cell has been replaced by a nucleic acid encoding an oligosaccharyltransferase, optionally wherein the waaL gene of the host cell has been replaced by *C. jejuni* pglB.

35. The host cell of any one of paragraphs 27-34, wherein said host cell comprises a nucleic acid that encodes a capsular polysaccharide polymerase (e.g. wzy) or an O antigen polymerase (e.g. wzy), optionally said capsular polysaccharide polymerase is from *Staphylococcus aureus*, optionally from *S. aureus* CP5 or CP8.

36. The host cell of any one of paragraphs 27-35, wherein said host cell comprises a nucleic acid that encodes a flippase (wzx), optionally wherein said flippase is from *Staphylococcus aureus*, optionally from *S. aureus* CP5 or CP8.

37. The host cell of any one of paragraphs 27-36, wherein said host cell further comprises an enzyme capable of modifying a monosaccharide, optionally an epimerase, optionally wherein said epimerase is from *Escherichia* species, *Shigella* species, *Klebsiella* species, *Xhantomonas* species, *Salmonella* species, *Yersinia* species, *Aeromonas* species, *Francisella* species, *Helicobacter* species, *Proteus* species, *Lactococcus* species, *Lactobacillus* species, *Pseudomonas* species, *Corynebacterium* species, *Streptomyces* species, *Streptococcus* species, *Enterococcus* species, *Staphylococcus* species, *Bacillus* species, *Clostridium* species, *Listeria* species, or *Campylobacter* species, optionally wherein said epimerase is from *E. coli*, optionally Z3206 from *E. coli* O157 or galE.

38. The host cell of any one of paragraphs 27-37, wherein the nucleic acid that encodes the modified HIa protein is in a plasmid in the host cell.

39. The host cell of any one of paragraphs 27-38, wherein the host cell is *E. coli.*

40. A method of producing a bioconjugate that comprises a modified HIa protein linked to a saccharide, said method comprising (i) culturing the host cell of any one of paragraphs 27-39 under conditions suitable for the production of proteins and (ii) isolating the bioconjugate.

41. A bioconjugate produced by the process of paragraph 40, wherein said bioconjugate comprises a saccharide linked to a modified HIa protein.

42. An immunogenic composition comprising the modified HIa protein of any one of paragraphs 1-18, or the conjugate of any one of paragraphs 19-24, or the bioconjugate of paragraph 41.

43. A method of making the immunogenic composition of paragraph 42 comprising the step of mixing the modified HIa protein or the conjugate or the bioconjugate with a pharmaceutically acceptable excipient or carrier.

44. A vaccine comprising the immunogenic composition of paragraph 42 and a pharmaceutically acceptable excipient or carrier.

45. A method for the treatment or prevention of *Staphylococcus aureus* infection in a subject in need thereof comprising administering to said subject a therapeutically effective amount of the modified HIa protein of any one of paragraphs 1-18, or the conjugate of any one of paragraphs 19-24, or the bioconjugate of paragraph 41.

46. A method of immunising a human host against *Staphylococcus aureus* infection comprising administering to the host an immunoprotective dose of the modified HIa protein of any one of paragraphs 1-18, or the conjugate of any one of paragraphs 19-24, or the bioconjugate of paragraph 41.

47. A method of inducing an immune response to *Staphylococcus aureus* in a subject, the method comprising administering a therapeutically or prophylactically effective amount of the modified HIa protein of any one of paragraphs 1-18, or the conjugate of any one of paragraphs 19-24, or the bioconjugate of paragraph 41.

48. A modified HIa protein of any one of paragraphs 1-18, or the conjugate of any one of paragraphs 19-24, or the bioconjugate of paragraph 41, for use in the treatment or prevention of a disease caused by *Staphylococcus aureus* infection.

49. Use of the modified HIa protein of any one of paragraphs 1-18, or the conjugate of any one of paragraphs 19-24, or the bioconjugate of paragraph 41, in the manufacture of a medicament for the treatment or prevention of a disease caused by *Staphylococcus aureus* infection.

In order that this invention may be better understood, the following examples are set forth. These examples are for purposes of illustration only, and are not to be construed as limiting the scope of the invention in any manner.

```
Description of the sequence listing
Amino acid sequence of mature wild-type Hla
                                                     SEQ ID NO: 1
ADSDINIKTGTTDIGSNTTVKTGDLVTYDKENGMHKKVFYSFIDDKNHNKKLLVIRTKGTIAGQYR

VYSEEGANKSGLAWPSAFKVQLQLPDNEVAQISDYYPRNSIDTKEYMSTLTYGFNGNVTGDDTGKI

GGLIGANVSIGHTLKYVQPDFKTILESPTDKKVGWKVIFNNMVNQNWGPYDRDSWNPVYGNQLFMK
```

-continued

TRNGSMKAADNFLDPNKASSLLSSGFSPDFATVITMDRKASKQQTNIDVIYERVRDDYQLHWTSTN

WKGTNTKDKWIDRSSERYKIDWEKEEMTN

Amino acid sequence of mature Hla H48C/G122C

SEQ ID NO: 2

ADSDINIKTGTTDIGSNTTVKTGDLVTYDKENGMHKKVFYSFIDDKNCNKKLLVIRTKGTIAGQYR

VYSEEGANKSGLAWPSAFKVQLQLPDNEVAQISDYYPRNSIDTKEYMSTLTYGFNCNVTGDDTGKI

GGLIGANVSIGHTLKYVQPDFKTILESPTDKKVGWKVIFNNMVNQNWGPYDRDSWNPVYGNQLFMK

TRNGSMKAADNFLDPNKASSLLSSGFSPDFATVITMDRKASKQQTNIDVIYERVRDDYQLHWTSTN

WKGTNTKDKWIDRSSERYKIDWEKEEMTN

Amino acid sequence of mature Hla H35L/H48C/G122C

SEQ ID NO: 3

ADSDINIKTGTTDIGSNTTVKTGDLVTYDKENGMLKKVFYSFIDDKNCNKKLLVIRTKGTIAGQYR

VYSEEGANKSGLAWPSAFKVQLQLPDNEVAQISDYYPRNSIDTKEYMSTLTYGFNCNVTGDDTGKI

GGLIGANVSIGHTLKYVQPDFKTILESPTDKKVGWKVIFNNMVNQNWGPYDRDSWNPVYGNQLFMK

TRNGSMKAADNFLDPNKASSLLSSGFSPDFATVITMDRKASKQQTNIDVIYERVRDDYQLHWTSTN

WKGTNTKDKWIDRSSERYKIDWEKEEMTN

Amino acid sequence of Hla H35L/H48C/G122C with N-terminal S and Flgl signal sequence

SEQ ID NO: 4

MIKFLSALILLLVTTAAQASADSDINIKTGTTDIGSNTTVKTGDLVTYDKENGMLKKVFYSFIDDK

NCNKKLLVIRTKGTIAGQYRVYSEEGANKSGLAWPSAFKVQLQLPDNEVAQISDYYPRNSIDTKEY

MSTLTYGFNCNVTGDDTGKIGGLIGANVSIGHTLKYVQPDFKTILESPTDKKVGWKVIFNNMVNQN

WGPYDRDSWNPVYGNQLFMKTRNGSMKAADNFLDPNKASSLLSSGFSPDFATVITMDRKASKQQTN

IDVIYERVRDDYQLHWTSTNWKGTNTKDKWIDRSSERYKIDWEKEEMTN

Amino acid sequence of Hla H35L/H48C/G122C with N-terminal S and Flgl signal sequence and C-terminal GSHRHR

SEQ ID NO: 5

MIKFLSALILLLVTTAAQASADSDINIKTGTTDIGSNTTVKTGDLVTYDKENGMLKKVFYSFIDDK

NCNKKLLVIRTKGTIAGQYRVYSEEGANKSGLAWPSAFKVQLQLPDNEVAQISDYYPRNSIDTKEY

MSTLTYGFNCNVTGDDTGKIGGLIGANVSIGHTLKYVQPDFKTILESPTDKKVGWKVIFNNMVNQN

WGPYDRDSWNPVYGNQLFMKTRNGSMKAADNFLDPNKASSLLSSGFSPDFATVITMDRKASKQQTN

IDVIYERVRDDYQLHWTSTNWKGTNTKDKWIDRSSERYKIDWEKEEMTNGSHRHR

Amino acid sequence of Hla H35L7H48C/G122C with N-terminal S and C-terminal GSHRHR

SEQ ID NO: 6

SADSDINIKTGTTDIGSNTTVKTGDLVTYDKENGMLKKVFYSFIDDKNCNKKLLVIRTKGTIAGQY

RVYSEEGANKSGLAWPSAFKVQLQLPDNEVAQISDYYPRNSIDTKEYMSTLTYGFNCNVTGDDTGK

IGGLIGANVSIGHTLKYVQPDFKTILESPTDKKVGWKVIFNNMVNQNWGPYDRDSWNPVYGNQLFM

KTRNGSMKAADNFLDPNKASSLLSSGFSPDFATVITMDRKASKQQTNIDVIYERVRDDYQLHWTST

NWKGTNTKDKWIDRSSERYKIDWEKEEMTNGSHRHR

Amino acid sequence of mature Hla H35L/H48C/G122C with KDQNRTK substitution for residue K131

SEQ ID NO: 7

ADSDINIKTGTTDIGSNTTVKTGDLVTYDKENGMLKKVFYSFIDDKNCNKKLLVIRTKGTIAGQYR

VYSEEGANKSGLAWPSAFKVQLQLPDNEVAQISDYYPRNSIDTKEYMSTLTYGFNCNVTGDDTGKD

QNRTKIGGLIGANVSIGHTLKYVQPDFKTILESPTDKKVGWKVIFNNMVNQNWGPYDRDSWNPVYG

NQLFMKTRNGSMKAADNFLDPNKASSLLSSGFSPDFATVITMDRKASKQQTNIDVIYERVRDDYQL

HWTSTNWKGTNTKDKWIDRSSERYKIDWEKEEMTN

-continued

Amino acid sequence of Hla H35L/H48C/G122C with N-terminal S, Flgl signal sequence, and KDQNRTK substitution for residue K131

SEQ ID NO: 8

MIKFLSALILLLVTTAAQASADSDINIKTGTTDIGSNTTVKTGDLVTYDKENGMLKKVFYSFIDDK

NCNKKLLVIRTKGTIAGQYRVYSEEGANKSGLAWPSAFKVQLQLPDNEVAQISDYYPRNSIDTKEY

MSTLTYGFNCNVTGDDTGKDQNRTKIGGLIGANVSIGHTLKYVQPDFKTILESPTDKKVGWKVIFN

NMVNQNWGPYDRDSWNPVYGNQLFMKTRNGSMKAADNFLDPNKASSLLSSGFSPDFATVITMDRKA

SKQQTNIDVIYERVRDDYQLHWTSTNWKGTNTKDKWIDRSSERYKIDWEKEEMTN

Amino acid sequence of Hla H35L/H48C/G122C with N-terminal S, Flgl signal sequence, C-terminal GSHRHR, and KDQNRTK substitution for residue K131

SEQ ID NO: 9

MIKFLSALILLLVTTAAQASADSDINIKTGTTDIGSNTTVKTGDLVTYDKENGMLKKVFYSFIDDK

NCNKKLLVIRTKGTIAGQYRVYSEEGANKSGLAWPSAFKVQLQLPDNEVAQISDYYPRNSIDTKEY

MSTLTYGFNCNVTGDDTGKDQNRTKIGGLIGANVSIGHTLKYVQPDFKTILESPTDKKVGWKVIFN

NMVNQNWGPYDRDSWNPVYGNQLFMKTRNGSMKAADNFLDPNKASSLLSSGFSPDFATVITMDRKA

SKQQTNIDVIYERVRDDYQLHWTSTNWKGTNTKDKWIDRSSERYKIDWEKEEMTNGSHRHR

Amino acid sequence of Hla H35L/H48C/G122C with N-terminal S, C-terminal GSHRHR, and KDQNRTK substitution for residue K131

SEQ ID NO: 10

SADSDINIKTGTTDIGSNTTVKTGDLVTYDKENGMLKKVFYSFIDDKNCNKKLLVIRTKGTIAGQY

RVYSEEGANKSGLAWPSAFKVQLQLPDNEVAQISDYYPRNSIDTKEYMSTLTYGFNCNVTGDDTGK

DQNRTKIGGLIGANVSIGHTLKYVQPDFKTILESPTDKKVGWKVIFNNMVNQNWGPYDRDSWNPVY

GNQLFMKTRNGSMKAADNFLDPNKASSLLSSGFSPDFATVITMDRKASKQQTNIDVIYERVRDDYQ

LHWTSTNWKGTNTKDKWIDRSSERYKIDWEKEEMTNGSHRHR

Minimal PglB glycosite consensus sequence

SEQ ID NO: 11

D/E-X-N-Z-S/T

Full PglB glycosite consensus sequence

SEQ ID NO: 12

K-D/E-X-N-Z-S/T-K

Flgl signal sequence

SEQ ID NO: 13

MIKFLSALILLLVTTAAQA

OmpA signal sequence

SEQ ID NO: 14

MKKTAIAIAVALAGFATVAQA

MalE signal sequence

SEQ ID NO: 15

MKIKTGARILALSALTTMMFSASALA

PelB signal sequence

SEQ ID NO: 16

MKYLLPTAAAGLLLLAAQPAMA

LTIIb signal sequence

SEQ ID NO: 17

MSFKKIIKAFVIMAALVSVQAHA

XynA signal sequence

SEQ ID NO: 18

MFKFKKKFLVGLTAAFMSISMFSATASA

DsbA signal sequence

SEQ ID NO: 19

MKKIWLALAGLVLAFSASA

TolB signal sequence

-continued

SEQ ID NO: 20
MKQALRVAFGFLILWASVLHA

SipA signal sequence

SEQ ID NO: 21
MKMNKKVLLTSTMAASLLSVASVQAS

Amino acid sequence of mature Hla H35L/H48C/G122C with C-terminal GSHRHR and KDQNRTK substitution for residue K131

SEQ ID NO: 22
ADSDINIKTGTTDIGSNTTVKTGDLVTYDKENGMLKKVFYSFIDDKNCNKKLLVIRTKGTIAGQYR

VYSEEGANKSGLAWPSAFKVQLQLPDNEVAQISDYYPRNSIDTKEYMSTLTYGFNCNVTGDDTGKD

QNRTKIGGLIGANVSIGHTLKYVQPDFKTILESPTDKKVGWKVIFNNMVNQNWGPYDRDSWNPVYG

NQLFMKTRNGSMKAADNFLDPNKASSLLSSGFSPDFATVITMDRKASKQQTNIDVIYERVRDDYQL

HWTSTNWKGTNTKDKWIDRSSERYKIDWEKEEMTNGSHRHR

KDQNRTK glycosite

SEQ ID NO: 23
KDQNRTK

KDQNATK glycosite

SEQ ID NO: 24
KDQNRTK

HRHR C-terminal tag

SEQ ID NO: 25
HRHR

GSHRHR C-terminal tag

SEQ ID NO: 26
GSHRHR

Mature Hla H35L/Y102C/G126C

SEQ ID NO: 27
ADSDINIKTGTTDIGSNTTVKTGDLVTYDKENGMLKKVFYSFIDDKNHNKKLLVIRTKGTIAGQYR

VYSEEGANKSGLAWPSAFKVQLQLPDNEVAQISDYCPRNSIDTKEYMSTLTYGFNGNVTCDDTGKI

GGLIGANVSIGHTLKYVQPDFKTILESPTDKKVGWKVIFNNMVNQNWGPYDRDSWNPVYGNQLFMK

TRNGSMKAADNFLDPNKASSLLSSGFSPDFATVITMDRKASKQQTNIDVIYERVRDDYQLHWTSTN

WKGTNTKDKWIDRSSERYKIDWEKEEMTN

Mature HlaH35L/G122C/H48C

SEQ ID NO: 28
ADSDINIKTGTTDIGSNTTVKTGDLVTYDKENGMLKKVFYSFIDDKNCNKKLLVIRTKGTIAGQYR

VYSEEGANKSGLAWPSAFKVQLQLPDNEVAQISDYYPRNSIDTKEYMSTLTYGFNCNVTGDDTGKI

GGLIGANVSIGHTLKYVQPDFKTILESPTDKKVGWKVIFNNMVNQNWGPYDRDSWNPVYGNQLFMK

TRNGSMKAADNFLDPNKASSLLSSGFSPDFATVITMDRKASKQQTNIDVIYERVRDDYQLHWTSTN

WKGTNTKDKWIDRSSERYKIDWEKEEMTN

Mature Hla H35L/G122C/L52C

SEQ ID NO: 29
ADSDINIKTGTTDIGSNTTVKTGDLVTYDKENGMLKKVFYSFIDDKNHNKKCLVIRTKGTIAGQYR

VYSEEGANKSGLAWPSAFKVQLQLPDNEVAQISDYYPRNSIDTKEYMSTLTYGFNCNVTGDDTGKI

GGLIGANVSIGHTLKYVQPDFKTILESPTDKKVGWKVIFNNMVNQNWGPYDRDSWNPVYGNQLFMK

TRNGSMKAADNFLDPNKASSLLSSGFSPDFATVITMDRKASKQQTNIDVIYERVRDDYQLHWTSTN

WKGTNTKDKWIDRSSERYKIDWEKEEMTN

Mature HlaH35L

SEQ ID NO: 30
ADSDINIKTGTTDIGSNTTVKTGDLVTYDKENGMLKKVFYSFIDDKNHNKKLLVIRTKGTIAGQYR

VYSEEGANKSGLAWPSAFKVQLQLPDNEVAQISDYYPRNSIDTKEYMSTLTYGFNGNVTGDDTGKI

GGLIGANVSIGHTLKYVQPDFKTILESPTDKKVGWKVIFNNMVNQNWGPYDRDSWNPVYGNQLFMK

-continued

TRNGSMKAADNFLDPNKASSLLSSGFSPDFATVITMDRKASKQQTNIDVIYERVRDDYQLHWTSTN

WKGTNTKDKWIDRSSERYKIDWEKEEMTN

EXAMPLES

Example 1: Design of Cysteine-Cysteine Cross-Linking Introduced into the Carrier Protein HIa (Hemolysin A)

Figure 1:
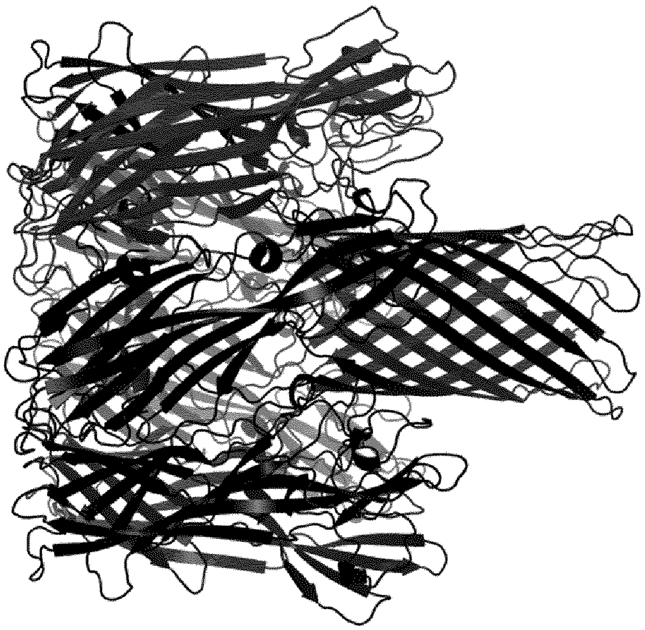
FIG. 1: Structural basis and rationale for the design of cysteine-cysteine cross-linking introduced into the carrier protein HIa (Hemolysin A)
Figure 1:
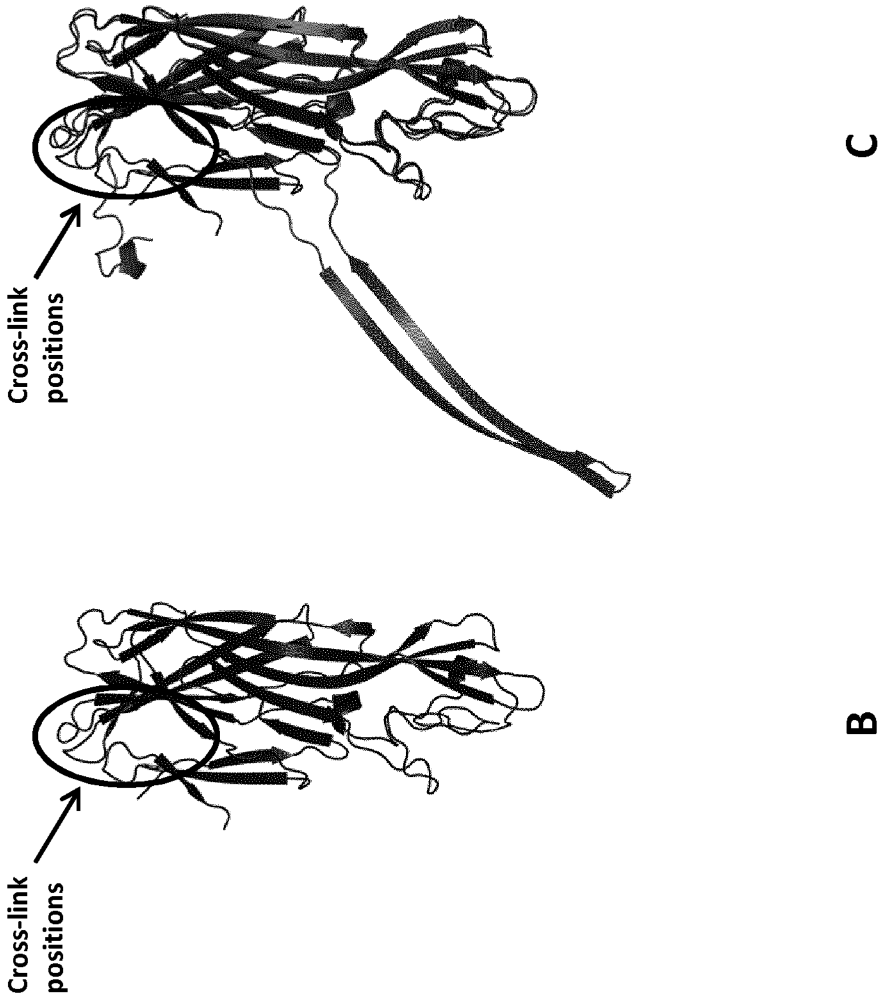

FIG. 1 shows the structural basis and rationale for the engineering of the *S. aureus* carrier protein Hemolysin A (HIa) for the introduction of cysteine amino acid residue pairs by replacing two other native amino acid residues. The figure represents the 3D crystal structures published on http://www.rcsb.org/showing a model of A) the toxic pore-forming HIa heptamer (PDB identifier 7AHL, Song et al., 1996), B) the non-toxic HIa monomer (PDB identifier 4IDJ, Foletti et al., 2013) and C) the superposition of one monomer in A) high-lighted in red and the monomer in B) high-lighted in blue. The broader region of the cysteine-cysteine cross-linking positions is indicated by a green oval. The goal of the engineering was to stabilize the protein to prevent aggregation, thereby enhancing the yield and to further detoxify the protein. The locus of the cross-linking position within the protein was selected to prevent the conformational change from the non-toxic monomer (blue) to form the toxic monomer (red) through inhibition of the beta strand extension needed for building the heptamer.

Figure 2:
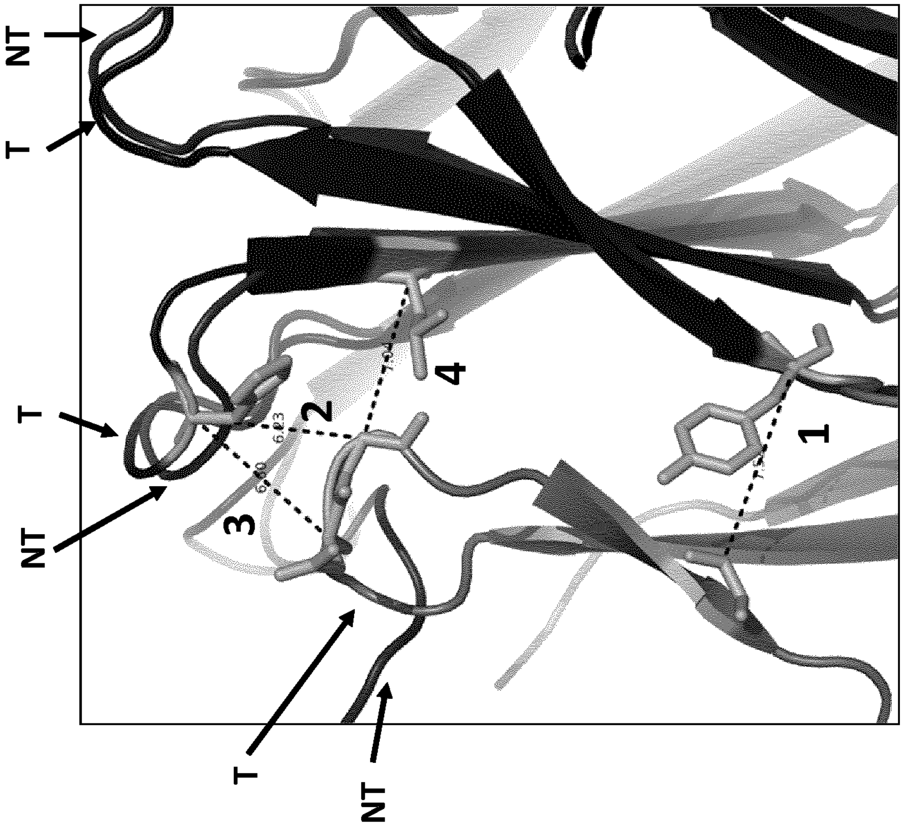
FIG. 2: Engineered region of superimposed HIa models from crystal structures 7AHL and 4IDJ Close up representation of the four pairs of amino acids that were mutated individually to cysteine residues creating four differently cross-linked HIa variants. Cross-linked amino acid residue pairs are: 1) Y102-G126; 2) G122-H48; 3) N121-H48; 4) G122-L52. The model of the toxic form is indicated as 'T', the non-toxic form is superimposed and indicated as 'NT'. The wild type residues are high-lighted in stick representations and the positions of the corresponding alpha carbon atoms (Cα) are linked by a dashed line for each pair of residues. Distances of Cα-Cα positions of each amino acid pair are indicated in Angströms (Å): Y102C/G126C: 7.52 Å; G122C/H48C: 6.23 Å; N121C/H48C: 6.60 Å; G122C/L52C: 7.04 Å.

FIG. 2 shows a close up of the amino acid pairs that were mutated to cysteine residues individually, pair by pair. The model of the toxic form is colored in red, the non-toxic form is superimposed and shown in blue. The wild type residues are high-lighted in green stick representations and the positions of the corresponding alpha Carbon atoms (Cα) are linked by a black dashed line for each pair of residues. Distances of Cα-Cα positions of each amino acid pair are indicated in Angströms (A): Y102C/G126C: 7.52 Å; G122C/H48C: 6.23 Å; N121C/H48C: 6.60 Å; G122C/L52C: 7.04 Å. N121C/H48C has been published (Kawate and Gouaux, 2003).

Example 2: Enhanced CP5-HIa Bioconjugate Productivity and Stability of Cross-Linked HIa Variants The stability (in terms of aggregate formation) and productivity of cross-linked HIa variants for CP5-HIa bioconjugate production was compared with that of non-cross-linked HIa. StGVXN1717 (W3110 ΔwaaL; ΔwecA-wzzE; rmlB-wecG::Clm) was co-transformed by electroporation with the plasmids encoding the *S. aureus* capsular polysaccharide CP5 (CPS 5) pGVXN393, *C. jejuni* oligosaccharyltransferase $PgIB_{cuo\ N311V\text{-}K482R\text{-}D483H\text{-}A669V}$ pGVXN1221 and individually with the *S. aureus* carrier proteins $HIa_{H35L}$ pGVXN570 or cross-link variants $HIa_{H35L\text{-}Y102C\text{-}G126C}$ pGVXN2178, $HIa_{H35L\text{-}H48C\text{-}G122C}$ pGVXN2179, $HIa_{H35L\text{-}H48C\text{-}N121C}$ pGVXN2180 or $HIa_{H35L\text{-}L52C\text{-}G122C}$ pGVXN2181 all carrying a glycosylation site at position 131 and a C-terminal hexahistidine (His6) affinity tag. A control transformation devoid of the gene encoding PgIB included *S. aureus* capsular polysaccharide CP5 (CPS 5) pGVXN393, the *S. aureus* carrier proteins $HIa_{H35L}$ (Hemolysin A) pGVXN570 combined with the empty backbone vector pGVXN72 (pEXT21, Dykxhoorn et al, Gene 177(1996) 133 136) of PgIB.

Cells were grown in TB medium, recombinant polysaccharide was expressed constitutively, PgIB and HIa were induced between a range of optical density $OD_{600nm}$ of 0.5 and 1.0.

After overnight induction, cells were harvested and the CP5-HIa bioconjugates were extracted by a periplasmic preparation using a lysis buffer (30 mM Tris-HCl pH 8.5, 1 mM EDTA, 20% Sucrose) supplemented with 1 mg/ml lysozyme. Periplasmic proteins were collected from the supernatant after centrifugation, loaded on a 4-12% SDS-PAGE and blotted onto a nitrocellulose membrane and detected by an anti-His tag antibody. Each sample for the SDS-PAGE was split and either boiled for 10 minutes at 98° C. or not boiled prior to loading. Proteins loaded were normalized for the optical density of the cells.

Figure 3:
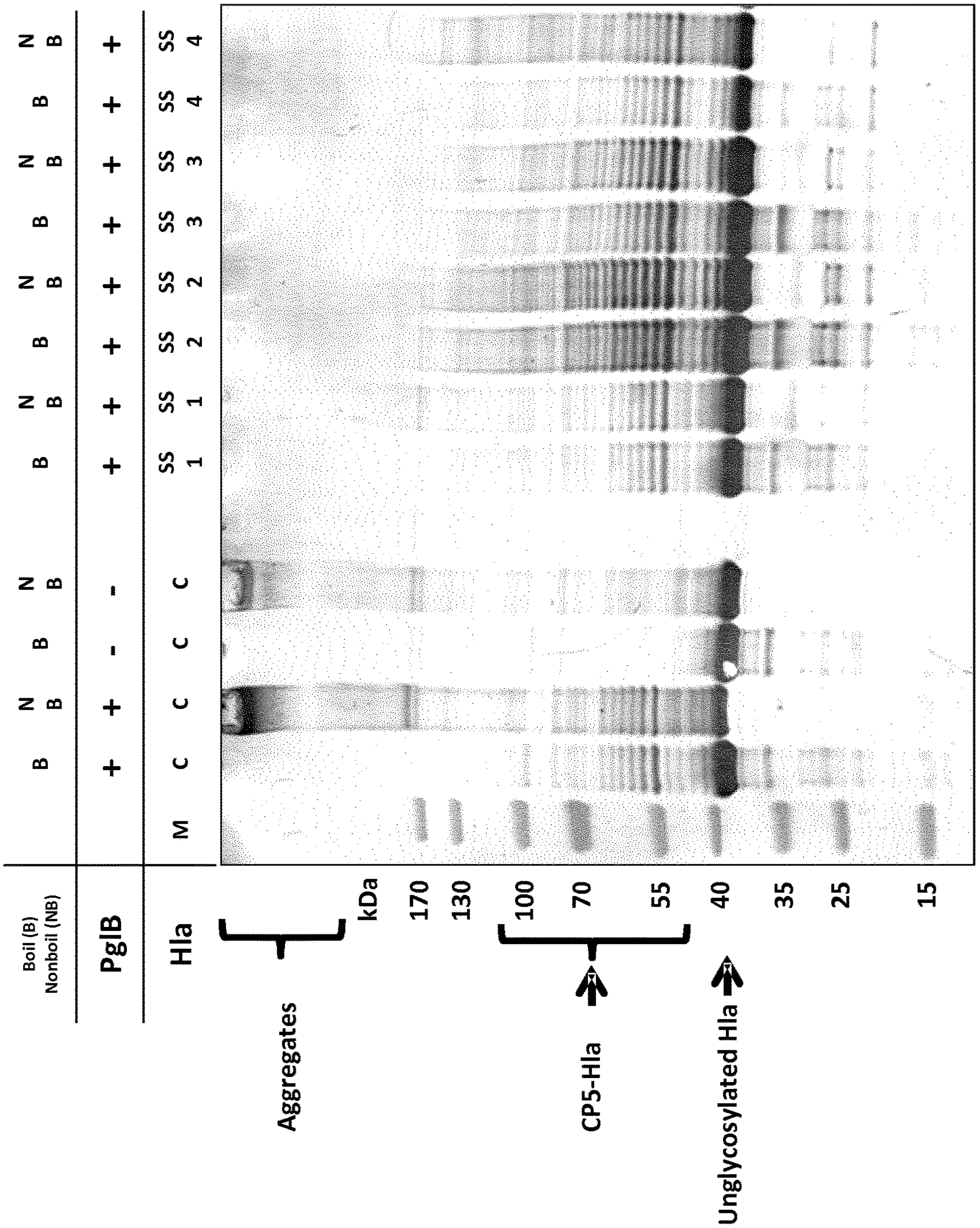
FIG. 3: Enhanced CP5-HIa bioconjugate productivity and stability of cross-linked HIa variants

The results are shown in FIG. 3. All of the cross-linked variants showed equivalent or higher levels of glycosylation compared to the non-cross-linked Ha, with G122C/H48C variant showing the highest level, followed by N121C/H48C. In addition, the non-cross-linked HIa showed substantial aggregate formation on the Western blot, seen as higher apparent molecular mass signals in the non-boiled samples, whereas aggregates were not visible on the blot for any of the cross-linked variants.

Methods

*E. coli* StGVXN1717 (W3110 ΔwaaL; ΔwecA-wzzE; rmlB-wecG::Clm) was co-transformed by electroporation with the plasmids encoding the *Staphylococcus aureus* capsular polysaccharide CP5 (CPS 5) pGVXN393, *Campylobacter jejuni* oligosaccharyltransferase $PgIB_{N311V\text{-}K482R\text{-}D483H\text{-}A669V}$ PGVXN1221 and individually with the *S. aureus* carrier proteins $HIa_{H35L}$ (Hemolysin A) pGVXN570 or cross-link variants $HIa_{H35L\text{-}Y102C\text{-}G126C}$ pGVXN2178, $HIa_{H35L\text{-}H48C\text{-}G122C}$ pGVXN2179, $HIa_{H35L\text{-}H48C\text{-}N121}$ pGVXN2180 or HIa H35L-L52C-G122C pGVXN2181 all carrying a glycosylation site at position 131 and a C-terminal hexahistidine (His6) affinity tag. A control transformation devoid of the gene encoding PgIB included *S. aureus* capsular polysaccharide CP5 (CPS 5) pGVXN393, the *S. aureus* carrier proteins $HIa_{H35L}$ (Hemolysin A) pGVXN570 combined with the empty backbone vector pGVXN72 of PgIB.

Transformed bacteria were grown overnight on selective agar plates supplemented with the three antibiotics tetracycline [20 μg/ml], ampicilline [100 μg/ml] and spectinomycin [80 μg/ml]. Cells were inoculated in 50 ml Lysogeny broth (LB) containing tetracycline [20 μg/ml], ampicilline [100 μg/ml] and spectinomycin [80 μg/ml] and shaken in an Erlenmeyer flask overnight at 37° C., 180 rpm. The following day, a main culture of 50 ml Terrific broth (TB) medium supplemented with 0.4-0.45% glycerol (Sigma, 49781), 10 mM MgCl2, tetracycline [20 μg/ml], ampicilline [100 μg/ml] and spectinomycin [80 μg/ml] was inoculated to a dilution of 0.1 optical density at $600_{nm}$ ($OD600_{nm}$), incubated in an Erlenmeyer flask at 180 rpm, 37° C., until an average $OD600_{nm}$ of 0.9-1.0 and induced. The cultures were shaken overnight at 37° C., 180 rpm, and 50 $OD600_n$m were harvested from each culture the following day. Cells were spun down by centrifugation at 4000 rpm for 15 minutes at 4° C., in an Eppendorf centrifuge and washed with 5 ml 0.9% sodium chloride (NaCl) followed by another centrifugation at 4000 rpm for 15 minutes at 4° C. The pellet was resuspended in 1 ml lysis buffer (30 mM Tris-HCl pH 8.5, 1 mM EDTA, 20% (w/v) sucrose) supplemented with 1 mg/ml lysozyme. The samples were incubated for 20 minutes at 4° C. on a rotation wheel, spun down by centrifugation at 14000 rpm for 20 minutes at 4° C. 45 microlitre of the supernatant was collected and boiled in 15 microlitre 4 times concentrated Laemmli buffer to reach to a final concentration of 62.5 mM Tris-HCl pH 6.8, 2% (w/v) sodium dodecyl sulfate, 5% (w/v) beta-mercaptoethanol, 10% (v/v) glycerol, 0.005% (w/v) bromphenol blue, for 15 minutes at 98° C. An identical set of samples were prepared without boiling prior to loading onto the SDS-PAGE. Proteins from an equivalent of 1 OD600$_n$m were separated by SDS-PAGE (Nu-PAGE, 4-12% Bis-Tris Gel, life technologies) with MOPS running buffer (50 mM MOPS, 50 mM Tris Base, 0.1% SDS, 1 mM EDTA, pH 7.7) at 200 Volt for 45 minutes. Proteins were then transferred onto a nitrocellulose membrane using the iBLOT gel transfer stacks (Novex, by Life Technologies). The nitrocellulose was blocked with 10% (w/v) milk powder dissolved in PBST (10 mM phosphate buffer pH 7.5, 137 mM sodium chloride, 2.7 mM potassium chloride purchased from Ambresco E703-500 ml, 0.1%/v/v) tween) for 20 minutes at room temperature followed by an immunoblot detection using a primary mouse anti-penta histidine antibody (Qiagen, 34660) at 0.1 μg/ml in PBST supplemented with 1% (w/v) milk powder, incubating the membrane for 1 hour at room temperature. In the following, the membrane was washed twice with PBST for 5 minutes and incubated with a secondary anti-mouse polyvalent horse radish peroxidase (HRP) coupled antibody (Sigma, A0412) in PBST supplemented with 1% (w/v) milk powder for 1 hour at room temperature. The membrane was washed 3 times with PBST for 5 minutes and protein bands were visualized by addition of TBM (TMB one component HRP membrane substrate, BioFX, TMBM-1000-01) and the reaction was stopped with deionized water.

Example 3: Correlation of Non-Cross-Linked Unglycosylated HIa (u-HIa) Aggregate Migration Behavior from Non-Boiled Sample in SDS-PAGE with Aggregate Species Detected by Size Exclusion Chromatography This example shows the correlation of aggregated unglycosylated, non-crosslinked HIa running as larger species in size exclusion chromatography and correspondingly as higher apparent molecular weight in SDS-PAGE when the sample is non-boiled. The results are shown in FIG. 5.

StGVXN2457 (W3110 ΔwaaL; ΔrlmB-wecG; ΔaraBAD) was transformed with the plasmid encoding the *S. aureus* carrier protein HIa$_{H35L}$ pGVXN570 carrying a glycosylation site at position 131 and a C-terminal hexahistidine affinity tag, by electroporation.

Cells were grown in TB medium HIa was induced with 0.2% arabinose at an optical density $OD_{600\ nm}$ of 0.66.

After overnight induction, cells were harvested and the HIa bioconjugate was extracted by a periplasmic preparation using a lysis buffer (30 mM Tris-HCl pH 8.5, 1 mM EDTA, 20% Sucrose) supplemented with 1 mg/ml lysozyme. Periplasmic protein was collected from the supernatant after centrifugation, loaded on a 10 ml IMAC resin (Hypercel, Pall) and eluted by a gradient elution. Fractions containing mostly the monomeric, non-aggregated species were pooled and further purified by an Anion exchange chromatography (ANX Sepharose) where the target protein was collected from the unbound fraction while the impurities were removed through binding to the column. The flow-through fraction was concentrated and injected into a size exclusion column (Superdex 200 10/300) to separate remaining aggregated species from monodisperse HIa. All purifications were carried out on a FPLC system (Aekta, Amersham Pharmacia). Purification fractions were analysed by 4-12% SDS-PAGE stained with SimplyBlue Safe Stain.

Methods.

*E. coli* StGVXN2457 (W3110 ΔwaaL; ΔrlmB-wecG; ΔaraBAD) was transformed with the plasmid encoding the *Staphylococcus aureus* carrier protein HIa$_{H35L}$ (Hemolysin A) pGVXN570 carrying a glycosylation site at position 131 and a C-terminal hexahistidine affinity tag, by electroporation.

Transformed bacteria were grown overnight on selective LB (Lysogeny broth) agar plate supplemented with the antibiotic ampicilline [100 μg/ml]. Cells were inoculated in 100 ml LB containing ampicilline [100 μg/ml] and shaken in an Erlenmeyer flask overnight at 37° C., 180 rpm. The following day, a main culture of 2000 ml Terrific broth (TB) medium supplemented with 0.4-0.45% glycerol (Sigma, 49781), 10 mM MgCl2 and ampicilline [100 μg/ml] was inoculated to a dilution of 0.1 optical density at $600_{nm}$ ($OD600_{nm}$), incubated in an Erlenmeyer flask at 180 rpm, 37° C. HIa was induced with 0.2% arabinose from a pBAD promoter at an optical density $OD_{600}$ nm of 0.66 and shaken overnight at 180 rpm and 37° C. Cells were harvested, spun down at 4° C., 5000 rpm for 20 minutes and washed with 200 ml 0.9% sodium chloride and spun down again at 4° C., 5000 rpm for 20 minutes. An equivalent of 8360 OD600 nm were resuspended in 167 ml lysis buffer (30 mM Tris-HCl pH 8.5, 1 mM EDTA, 20% (w/v) sucrose) supplemented with 1 mg/ml lysozyme. The sample was incubated for 15 minutes at 4° C. on a rotation wheel, spun down by centrifugation at 8000 rpm for 30 minutes at 4° C. and the supernatant was recovered. 10 ml IMAC purification resin (Hypercel, Pall) was equilibrated with 30 ml 30 mM Tris-HCl pH 8.0, 500 mM NaCl, 5 mM Imidazole, and incubated with the supernatant supplemented with 43 ml 150 mM Tris-HCl pH 8.0, 2500 mM NaCl, 25 mM Imidazole, 4 mM magnesium chloride for 40 minutes at room temperature. The Resin was packed into a XK16 column (GE Healthcare) and washed with 50 ml 30 mM Tris-HCl pH 8.0, 500 mM NaCl, 5 mM imidazole using a peristaltic pump (Ismatec). In the following, the column was attached to a FPLC system (Aekta, Amersham Pharmacia) and the protein was eluted in the same buffer condition with an Imidazole gradient up to 500 mM. 45 microlitre of the chromatography fractions were supplemented with 15 microlitre 4 times concentrated Laemmli buffer to obtain a final concentration of 62.5 mM Tris-HCl pH 6.8, 2% (w/v) sodium dodecyl sulfate, 5% (w/v) beta-mercaptoethanol, 10% (v/v) glycerol, 0.005% (w/v) bromphenol blue. Samples were boiled at 95° C. for 15 minutes, 40 microlitres were separated by 4-12% SDS-PAGE (Nu-PAGE, 4-12% Bis-Tris Gel, life technologies) with MOPS running buffer (50 mM MOPS, 50 mM Tris Base, 0.1% SDS, 1 mM EDTA, pH 7.7) at 200 Volt for 45 minutes. Proteins were visualized with SimplyBlue Safe Stain. Three elution peaks were observed, at approximately 90, 190 and 340 mM imidazole. Five fractions eluting at approximately 190 mM imidazole (second peak, 15 ml) were pooled and centrifuged at 10000 rpm, 30 minutes at 4° C. and the supernatant was diluted with 35 ml of Buffer A (10 mM Tris-HCl pH 7.5) to reach a conductivity of 2.69 mS/cm. The protein was loaded on a 25 ml anion exchange chromatography column (ANX Sepharose), washed with 50 ml buffer A and proteins were eluted by a differential gradient with buffer B (10 mM Tris-HCl pH 7.5, 1M NaCl): 3 column volumes (cv) to 13% buffer B, 5 cv to 16% buffer B and 7 cv to 100% buffer B. All fractions were analyzed by SDS-PAGE and visualized with SimplyBlue Safe Stain as described above. The target protein was mostly detected in the unbound fractions, pooled and concentrated with 30 kilodalton molecular weight cutoff filter (Amicon Ultra-15 Centrifugal Filter Unit) to 500 microlitre and injected into a size exclusion chromatography column (Superdex 200 10/300, GE healthcare) to separate aggregates from monomeric carrier proteins (see FIG. 5A, absorbance readout). Fractions were again analyzed by SDS-PAGE and visualized with SimplyBlue Safe Stain as described above (FIG. 5A, SDS-PAGE gel). Additionally, the proteins from aggregated species and monomeric species were analyzed on a SDS-PAGE without boiling the samples which confirmed the clear correlation of high molecular weight migration behavior on SDS-PAGE with aggregated species (FIG. 5B; non-boiled sample in Lane 3 shows very high MW band near the top of the gel. Consequently, this allows a fast read-out for analysis of the homogeneity of the carrier protein HIa, either nonglycosylated or glycosylated, for further experiments without necessity to purify the protein to high purity.

Example 4: Analysis of Aggregated u-HIa Species by Dynamic Light Scattering (DLS)

Aggregated non-cross-linked u-HIa species were analysed by Dynamic Light Scattering (DLS). The Results are shown in FIG. 4. 4A) shows the average size distribution profile of an aggregated HIa. 4B) shows the aggregated u-HIa species used for the analysis, peak one from an IMAC eluting at approximately 90 mM imidazole. The raw data of the triplicate measurement yielding 122.4 nm average particle size are shown in Table 1.

TABLE 1

| Sample no | Repet No | Av Diameter (nm) | PD | Mean (nm) | D(10%) (nm) | D(50%) (nm) | D(90%) (nm) |
|---|---|---|---|---|---|---|---|
| 1 | 1 | 118.7 | 0.326 | 201.0 | 52.8 | 148.8 | 411.7 |
| 2 | 2 | 126.7 | 0.303 | 208.3 | 56.9 | 154.7 | 423.1 |
| 3 | 3 | 121.8 | 0.340 | 206.7 | 54.0 | 152.5 | 424.3 |
| Average | | 122.4 | 0.323 | 205.3 | 54.6 | 152.0 | 419.7 |

Figure 4C:
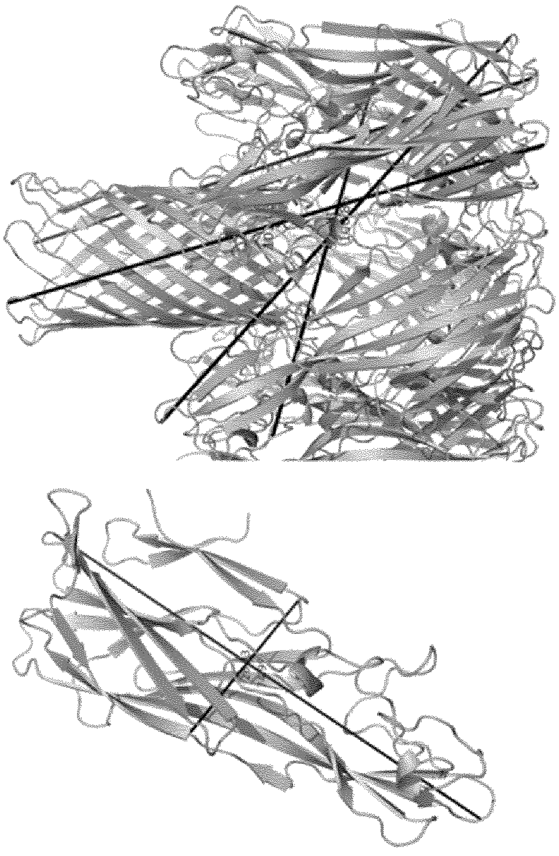

FIG. 4C shows measurements done in program Pymol to estimate the rough maximal dimensions of either the monomeric or heptameric molecule in nanometers. The longest dimension in the monomer is maximal 8 nanometer, the heptameric form has a maximal dimension of approximately 10 nanometer in all directions.

StGVXN2457 (W3110 ΔwaaL; ΔrlmB-wecG; ΔaraBAD) was transformed with the plasmid encoding the *S. aureus* carrier protein $HIa_{H35L}$ pGVXN570 carrying a glycosylation site at position 131 and a C-terminal hexahistidine affinity tag, by electroporation.

Cells were grown in TB medium and HIa was induced with 0.2% arabinose at an optical density $OD_{600\ nm}$ of 0.66.

After overnight induction, cells were harvested and the HIa bioconjugate was extracted by a periplasmic preparation using a lysis buffer (30 mM Tris-HCl pH 8.5, 1 mM EDTA, 20% Sucrose) supplemented with 1 mg/ml lysozyme. Periplasmic protein was collected from the supernatant after centrifugation, loaded on a 10 ml IMAC resin (Hypercel, Pall) and eluted by a gradient elution.

Methods

*E. coli* StGVXN2457 (W3110 ΔwaaL; ΔrlmB-wecG; ΔaraBAD) was transformed with the plasmid encoding the *Staphylococcus aureus* carrier protein $HIa_{H35L}$ (Hemolysin A) pGVXN570 carrying a glycosylation site at position 131 and a C-terminal hexahistidine affinity tag, by electroporation.

Transformed bacteria were grown overnight on selective LB (Lysogeny broth) agar plate supplemented with the antibiotic ampicilline [100 μg/ml]. Cells were inoculated in 100 ml LB containing ampicilline [100 μg/ml] and shaken in an Erlenmeyer flask overnight at 37° C., 180 rpm. The following day, a main culture of 2000 ml Terrific broth (TB) medium supplemented with 0.4-0.45% glycerol (Sigma, 49781), 10 mM MgCl2 and ampicilline [100 μg/ml] was inoculated to a dilution of 0.1 optical density at $600_{nm}$ ($OD600_{nm}$), incubated in an Erlenmeyer flask at 180 rpm, 37° C. HIa was induced with 0.2% arabinose from a pBAD promoter at an optical density $OD_{600}$ nm of 0.66 and shaken overnight at 180 rpm and 37° C. Cells were harvested, spun down at 4° C., 5000 rpm for 20 minutes and washed with 200 ml 0.9% sodium chloride and spun down again at 4° C., 5000 rpm for 20 minutes. An equivalent of 8360 OD600 nm were resuspended in 167 ml lysis buffer (30 mM Tris-HCl pH 8.5, 1 mM EDTA, 20% (w/v) sucrose) supplemented with 1 mg/ml lysozyme. The sample was incubated for 15 minutes at 4° C. on a rotation wheel, spun down by centrifugation at 8000 rpm for 30 minutes at 4° C. and the supernatant was recovered. 10 ml IMAC purification resin (Hypercel, Pall) was equilibrated with 30 ml 30 mM Tris-HCl pH 8.0, 500 mM NaCl, 5 mM Imidazole, and incubated with the supernatant supplemented with 43 ml 150 mM Tris-HCl pH 8.0, 2500 mM NaCl, 25 mM Imidazole, 4 mM magnesium chloride for 40 minutes at room temperature. The Resin was packed into a XK16 column (GE Healthcare) and washed with 50 ml 30 mM Tris-HCl pH 8.0, 500 mM NaCl, 5 mM imidazole using a peristaltic pump (Ismatec). In the following, the column was attached to a FPLC system (Aekta, Amersham Pharmacia) and the protein was eluted in the same buffer condition with an Imidazole gradient up to 500 mM. Three peaks at different imidazole concentrations were observed. As judged from a size exclusion chromatography (see Example 3, FIG. 5), this HIa species eluting in the first peak at approximately 90 mM imidazole is an aggregated form and the fractions thereof were collected and analysed by Dynamic Light Scattering (DLS) to obtain the average size distribution. A triplicate measurement of the sample was carried at 0.9 mg/ml, using an accumulation time of 70. Measurements were done at 25° C. on a Delsa Nano C (Beckman Coulter) which yielded an average size of 122.4 nanometer (nm). The formation of a potentially heptameric and toxic form can therefore be excluded since the average particle measured is ten times larger and is more likely to an aggregated form of HIa. It was attempted to also measure the monomeric form of HIa which did not lead to any signal because the protein is too small for this method (dimension of approximately 3×8 nm).

Example 5: Analysis of Elution Profiles of Non-Cross-Linked Versus Cross-Linked Unglycosylated Hemolysin a Variants from Immobilized Metal Affinity Chromatography (IMAC) and Size Exclusion Chromatography (SEC)

The immobilized metal affinity chromatography (IMAC) elution profile of unglycosylated, non-cross-linked HIa was compared with the immunoblot analysis of the respective elution fractions with an anti-His antibody, revealing a heterogenous elution behavior of the target protein. Results are shown in FIG. 6.

The immobilized metal affinity chromatography (IMAC) elution profile from unglycosylated, non-cross-linked HIa and of the four unglycosylated, cross-linked HIa variants were then compared, as shown in FIG. 7. This showed prevention (Y102C/G126C) or strongly reduced formation of aggregate relative to monomer, associated with increased protein yield (G122C/H48C).

The unglycosylated, non-cross-linked HIa variant eluted as aggregates or monomers obtained from the IMAC gradient elution shown in FIG. 7 and the IMAC eluates from the monomeric species of the four cross-linked HIa variants shown in FIG. 7 were then subjected to size exclusion chromatography analysis. The results are shown in FIG. 8. StGVXN1717 (W3110 ΔwaaL; ΔwecA-wzzE; rmlB-wecG::Clm) was co-transformed by electroporation with the plasmids encoding the *S. aureus* capsular polysaccharide CP5 (CPS 5) pGVXN393, with the empty plasmid vector pGVXN72 devoid of the gene encoding for *Campylobacter jejuni* oligosaccharyltransferase $PgIB_{cuo\ N311V\text{-}K482R\text{-}D483H\text{-}A669V}$ and with one of the *S. aureus* carrier proteins $HIa_{H35L}$ pGVXN570, cross-link variants $HIa_{H35L\text{-}Y102C\text{-}G126C}$ pGVXN2178, $HIa_{H35L\text{-}H48C\text{-}G122C}$ pGVXN2179, $HIa_{H35L\text{-}H48C\text{-}N121C}$ pGVXN2180 or $HIa_{H35L\text{-}L52C\text{-}G122C}$ pGVXN2181 all carrying a glycosylation site at position 131 and a C-terminal hexahistidine (His6) affinity tag.

Cells were grown in TB medium, recombinant polysaccharide was expressed constitutively. HIa was induced between a range of optical density $OD_{600\ nm}$ of 0.5 and 1.0. After overnight induction, cells were harvested and the unglycosylated HIa proteins were extracted by an osmotic shock procedure. Cells were resuspended in 1 ml 8.3 mM Tris-HCl pH 7.4, 43.3 mM NaCl, 0.9 mM KCl and 0.5 ml resuspension buffer (75% (w/v) sucrose, 30 mM EDTA, 600 mM Tris-HCl pH 8.5) and rotated for 20 minutes at 4° C. Cells were pelleted and resuspended in osmotic shock buffer (10 mM Tris-HCl pH 8.0) followed by another incubation of 30 minutes at 4° C. Cells were spun down again and supernatants were loaded on a 1 ml HisTrap FF column, and the proteins were eluted with a gradient elution. Elution fractions from sample deriving from the non-cross-linked HIa variant pGVXN570 were loaded on a 4-12% SDS-PAGE and blotted onto a nitrocellulose membrane and detected by an anti-His tag antibody.

Methods

*E. coli* StGVXN1717 (W3110 ΔwaaL; ΔwecA-wzzE; rmlB-wecG::Clm) was co-transformed by electroporation with the plasmids encoding the *Staphylococcus aureus* capsular polysaccharide CP5 (CPS 5) pGVXN393, with the empty plasmid vector pGVXN72 devoid of the gene encoding for *Campylobacter jejuni* oligosaccharyltransferase $PgIB_{cuo\ N311V\text{-}K482R\text{-}D483H\text{-}A669V}$ and with one of the *S. aureus* carrier proteins $HIa_{H35L}$ (Hemolysin A) pGVXN570, cross-link variants $HIa_{H35L\text{-}Y102C\text{-}G126C}$ pGVXN2178, $HIa_{H35L\text{-}H48C\text{-}G122C}$ pGVXN2179, $HIa_{H35L\text{-}H48C\text{-}N121C}$ pGVXN2180 or $HIa_{H35L\text{-}L52C\text{-}G122C}$ pGVXN2181 all carrying a glycosylation site at position 131 and a C-terminal hexahistidine (His6) affinity tag. Transformed bacteria were grown overnight on selective Lysogeny broth (LB) agar plates supplemented with the three antibiotics tetracycline [20 μg/ml], ampicilline [100 μg/ml] and spectinomycin [80 μg/ml]. Cells were inoculated in 50 ml Lysogeny broth (LB) containing tetracycline [20 μg/ml], ampicilline [100 μg/ml] and spectinomyin [80 μg/ml] and shaken in an Erlenmeyer flask overnight at 180 rpm and 37° C. The following day, main cultures of 50 ml Terrific broth (TB) medium supplemented with 0.4-0.45% glycerol (Sigma, 49781), 10 mM MgCl2, tetracycline [20 μg/ml], ampicilline [100 μg/ml] and spectinomycin [80 μg/ml] were inoculated to a dilution of 0.1 optical density at $600_{nm}$ ($OD600_{nm}$), incubated in an Erlenmeyer flask at 180 rpm, 37° C., until an average $OD600_{nm}$ of 0.9-1.0 and induced with isopropyl-β-D-thiogalactopyranoside (IPTG, Thermoscientific R0393) and arabinose and shaken overnight at 180 rpm and 37° C. 200 $OD600_n$m were harvested from each sample, spun down at 4° C., 4000 rpm for 15 minutes and the cell pellets were washed with 20 ml 0.9% NaCl, spun down again at 4° C., 4000 rpm for 15 minutes. Proteins were purified by an osmotic shock procedure by resuspension in 1 ml 8.3 mM Tris-HCl pH 7.4, 43.3 mM NaCl, 0.9 mM KCl and 0.5 ml resuspension buffer (75% Sucrose, 30 mM EDTA, 600 mM Tris-HCl pH 8.5). The cell suspension was incubated at 4° C. for 20 minutes on a rotating wheel, pelleted by centrifugation at 9000 rpm for 30 minutes at 4° C. and resuspended in 1.5 ml osmotic shock buffer (10 mM Tris-HCl pH 8.0). The suspension was incubated at 4° C. for 30 minutes by rotation and spun down at 14000 rpm for 30 minutes at 4° C. The supernatants were recovered and supplemented with magnesium chloride (MgCl2) and 5× binding buffer (150 mM Tris-HCl pH 8.0, 2.5 M NaCl, 25 mM imidazole) to reach final concentration of 50 mM MgCl2 and IMAC (Immobilized metal affinity chromatography) binding condition of 30 mM Tris-HCl pH 8.0, 500 mM NaCl, 5 mM imidazole). 1 millilitre HisTrap FF columns (GE healthcare) were equilibrated with 10 ml binding buffer (30 mM Tris-HCl pH 8.0, 500 mM NaCl, 5 mM imidazole) and samples were loaded onto the columns and washed with 10 ml binding buffer (30 mM Tris-HCl pH 8.0, 500 mM NaCl, 5 mM imidazole) using a peristaltic pump (Ismatec). In the following, columns were attached to a FPLC system (Aekta, Amersham Pharmacia), washed with 10 ml 30 mM Tris-HCl, pH 8.0, 50 mM NaCl, 5 mM imidazole and eluted by a gradient from 5-500 mM imidazole in 15 ml. 45 microlitre of each elution fraction from the sample produced with non-cross-linked HIa pGVXN570 were supplemented with 15 microlitre 4× Laemmli buffer to reach to a concentration of 62.5 mM Tris-HCl pH 6.8, 2% (w/v) sodium dodecyl sulfate, 5% (w/v) beta-mercaptoethanol, 10% (v/v) glycerol, 0.005% (w/v) bromphenol blue and boiled for 15 minutes at 98° C. 30 microlitre of each sample were analyzed by SDS-PAGE (Nu-PAGE, 4-12% Bis-Tris Gel, life technologies) with MOPS running buffer (50 mM MOPS, 50 mM Tris Base, 0.1% SDS, 1 mM EDTA, pH 7.7) at 200 Volt for 45 minutes. Proteins were then transferred onto a nitrocellulose membrane using the iBLOT gel transfer stacks (Novex, by Life Technologies). The nitrocellulose was blocked with 10% (w/v) milk powder dissolved in PBST (10 mM phosphate buffer pH 7.5, 137 mM sodium chloride, 2.7 mM potassium chloride purchased from Ambresco E703-500 ml, 0.1%/v/v) tween) for 20 minutes at room temperature followed by an immunoblot detection using a primary mouse anti-penta histidine antibody (Qiagen, 34660) at 0.1 μg/ml in PBST supplemented with 1% (w/v) milk powder, incubating the membrane for 1 hour at room temperature. In the following, the membrane was washed twice with PBST for 5 minutes and incubated with a secondary anti-mouse polyvalent horse radish peroxidase (HRP) coupled antibody (Sigma, A0412) in PBST supplemented with 1% (w/v) milk powder for 1 hour at room temperature. The membrane was washed 3 times with PBST for 5 minutes and protein bands were visualized by addition of TBM (TMB one component HRP membrane substrate, BioFX, TMBM-1000-01) and the reaction was stopped with deionized water.

IMAC eluates shown in FIG. 7 were further analyzed by size exclusion chromatography (SEC). A size exclusion chromatography (SEC) Superdex 200 10/300 column (GE healthcare) was equilibrated with 1×TBS (Tris buffered saline, Fisher Scientific), pH 7.4, at 0.5 ml/min on a FPLC system (Aekta, Amersham Pharmacia). 500 microlitre of IMAC elution peaks from aggregated and monomeric species of unglycosylated, non-crosslinked HIa and monomeric species collected from unglycosylated cross-linked HIa variants were injected into a size exclusion chromatography Superdex 200 10/300 column. Elution profiles were recorded at a absorption wavelength of 280 nm and overlayed as shown in FIG. 8.

Example 6: Highly Selective Purification of CP5-HIa Carrying a C-Terminal HRHR Tag Using Cationic Exchange Chromatography A highly selective purification step for the CP5-HIa bioconjugate carrying a HRHR purification tag using a cationic exchange resin was performed, as shown in FIG. 9. Results obtained using CP5-HIa lacking a purification tag are shown in FIG. 10. StGVXN1717 (W3110 ΔwaaL; ΔwecA-wzzE; rmlB-wecG::Clm) was co-transformed with the plasmids encoding the *S. aureus* capsular polysaccharide CP5 (CPS 5) pGVXN393, the *S. aureus* carrier protein $HIa_{H35L\text{-}H48C\text{-}G122C}$ pGVXN2533 carrying a glycosylation site at position 131, with or without a C-terminal histidine-arginine-histidine-arginine tag and *Campylobacter jejuni* oligosaccharyltransferase $PglB_{cuo\ N311V\text{-}K482R\text{-}D483H\text{-}A669V}$ pGVXN1221, by electroporation.

Cells were grown in TB medium, recombinant polysaccharide was expressed constitutively, HIa and PglB were induced at an optical density $OD_{600\ nm}$ of 0.74.

After overnight induction, cells were harvested and the CP5-HIa bioconjugate was released from the periplasm by an osmotic shock procedure. Cells were resuspended in 8.3 mM Tris-HCl pH 7.4, 43.3 mM NaCl, 0.9 mM KCl and resuspension buffer (75% (w/v) sucrose, 30 mM EDTA, 600 mM Tris-HCl pH 8.5) and rotated for 20 minutes at 4° C. Cells were pelleted and resuspended in osmotic shock buffer (10 mM Tris-HCl pH 8.0) followed by another incubation of 20 minutes at 4° C. Cells were spun down again and the supernatant was loaded onto a 1 ml cation exchange column and the bioconjugate was recovered by a gradient elution. Proteins from the elution fractions were separated by a 4-12% SDS-PAGE and blotted onto a nitrocellulose membrane and detected by an anti-HIa antibody or the gel was directly stained with SimplyBlue Safe Stain. The results are shown in FIGS. 9 (with tag) and 10 (without tag).

Methods

For the tagged protein, *E. coli* StGVXN1717 (W3110 ΔwaaL; ΔwecA-wzzE; rmlB-wecG::Clm) was co-transformed with the plasmids encoding the *Staphylococcus aureus* capsular polysaccharide CP5 (CPS 5) pGVXN393, the *S. aureus* carrier protein $HIa_{H35L\text{-}H48C\text{-}G122C}$ pGVXN2533 (Hemolysin A) carrying a glycosylation site at position 131 and a C-terminal histidine-arginine-histidine-arginine tag and *Campylobacter jejuni* oligosaccharyltransferase $PglB_{cuo\ N311\text{-}K482R\text{-}D483H\text{-}A669}$ pGVXN1221 by electroporation.

Transformed bacteria were grown overnight on selective TB agar plates supplemented with 0.4-0.45% glycerol (Sigma, 49781), 2 mM magnesium chloride and the three antibiotics tetracycline [20 μg/ml], kanamycine [50 μg/ml] and spectinomycin [80 μg/ml]. Cells were inoculated in 50 ml Lysogeny broth (LB) containing 10 mM magnesium chloride, tetracycline [20 μg/ml], kanamycine [50 μg/ml] and spectinomycin [80 μg/ml] and shaken in an Erlenmeyer flask overnight at 37° C., 180 rpm. The following day, a main culture of 1000 ml Terrific broth (TB) medium supplemented with 0.4-0.45% glycerol (Sigma, 49781), 10 mM MgCl2, tetracycline [20 μg/ml], kanamycine [50 μg/ml] and spectinomycin [80 μg/ml] was inoculated to a dilution of 0.1 optical density at $600_{nm}$($OD600_{nm}$), incubated in an Erlenmeyer flask at 180 rpm, 37° C. Recombinant polysaccharide was expressed constitutively, hemolysin A was induced with arabinose from a pBAD promoter and PglB with isopropyl-β-D-thiogalactopyranoside (IPTG) at an optical density $OD_{600\ nm}$ of 0.74 and shaken overnight at 180 rpm and 37° C. Cells were harvested, spun down at 4° C., 9000 rpm for 15 minutes and washed with 110 ml 0.9% sodium chloride and an equivalent of 1560 OD600 nm were extracted by an osmotic shock procedure. Cells were resuspended in 5 ml ⅓×TBS (Tris buffered saline, Fisher Scientific) and 2.5 ml resuspension buffer (75% (w/v) sucrose, 30 mM EDTA, 600 mM Tris-HCl pH 8.5) and rotated for 20 minutes at 4° C. Cells were pelleted and resuspended in 7.5 ml osmotic shock buffer (10 mM Tris-HCl pH 8.0) followed by another incubation of 30 minutes at 4° C. Cells were spun down again by centrifugation, supernatants were recovered and filtered with a 0.2 micrometer filter. 2 ml of the filtrate were supplemented with a 5M sodium chloride solution to a final concentration of 50 mM and the pH was adjusted to 5.5 with 1M citric acid. The sample was spun down by centrifugation at 14000 rpm, at 4° C. for 5 minutes. A purification column was prepared (Proteus FliQ FPLC column; 1 ml; generon) with 1 ml of a cation exchange resin (Nuvia HR-S, Biorad) and equilibrated with 20 mM Citrate, 50 mM NaCl, pH 5.5 on an FPLC system (Aekta, Amersham Pharmacia). The sample was applied with a 2 ml superloop, the column was washed with 5 ml 20 mM Citrate, 50 mM NaCl, pH 5.5 and the bioconjugate was eluted applying a gradient to 20 mM Citrate, 500 mM NaCl, pH 5.5 in 10 column volumes. Flow-through and wash fractions collected were 500 microlitre, elution fractions had a volume of 350 microlitre. 45 microlitre of the chromatography fractions were supplemented with 15 microlitre 4 times concentrated Laemmli buffer to obtain a final concentration of 62.5 mM Tris-HCl pH 6.8, 2% (w/v) sodium dodecyl sulfate, 5% (w/v) beta-mercaptoethanol, 10% (v/v) glycerol, 0.005% (w/v) bromphenol blue. Samples were boiled at 95° C. for 15 minutes, 40 microlitres were separated by 4-12% SDS-PAGE (NuPAGE, 4-12% Bis-Tris Gel, life technologies) with MOPS running buffer (50 mM MOPS, 50 mM Tris Base, 0.1% SDS, 1 mM EDTA, pH 7.7) at 200 Volt for 45 minutes. Proteins were then transferred onto a nitrocellulose membrane using the iBLOT gel transfer stacks (Novex, by Life Technologies). The nitrocellulose was blocked with 10% (w/v) milk powder dissolved in PBST (10 mM phosphate buffer pH 7.5, 137 mM sodium chloride, 2.7 mM potassium chloride purchased from Ambresco E703-500 ml, 0.1%/v/v) tween) for 20 minutes at room temperature followed by an immunoblot detection using a primary rabbit anti-HIa antibody (polyclonal purified IgG, Glycovaxyn Nr 160) at 2.5 μg/ml in PBST for 1 hour at room temperature. The membrane was washed twice with PBST and incubated with a secondary goat anti-rabbit horse radish peroxidase (HRP) coupled antibody (Biorad, 170-6515) in PBST for 1 hour at room temperature. The membrane was washed 3 times with PBST for 5 minutes and protein bands were visualized by addition of TBM (TMB one component HRP membrane substrate) and the reaction was stopped with deionized water.

From the boiled samples, 20 microlitres were loaded on a second 4-12% SDS-PAGE gel (Nu-PAGE, 4-12% Bis-Tris Gel, life technologies) and proteins were separated in MOPS running buffer (50 mM MOPS, 50 mM Tris Base, 0.1% SDS, 1 mM EDTA, pH 7.7) at 200 Volt for 45 minutes. The gel was stained two consecutive times with 10 ml SimplyBlue SafeStain (Life Technologies) followed by a destaining step using deionized water. The results are shown in FIG. 9.

For the non-tagged protein, *E. coli* StGVXN1717 (W3110 ΔwaaL; ΔwecA-wzzE; rmlB-wecG::Clm) was co-transformed with the plasmids encoding the *Staphylococcus aureus* capsular polysaccharide CP5 (CPS 5) pGVXN393, the *S. aureus* carrier protein $HIa_{H35L-H48C-G122C}$ pGVXN2438 carrying a glycosylation site at position 131 and no C-terminal tag and *Campylobacter jejuni* oligosaccharyltransferase $PglB_{cuo\ N311V-K482R-D483H-A669V}$ pGVXN1221 by electroporation.

Transformed bacteria were grown overnight on selective TB agar plates supplemented with 0.4-0.45% glycerol (Sigma, 49781), 2 mM magnesium chloride and the three antibiotics tetracycline [20 μg/ml], spectinomycine [80 μg/ml] and ampicilline [100 μg/ml]. Cells were inoculated in 50 ml Lysogeny broth (LB) containing 10 mM magnesium chloride, tetracycline [20 μg/ml], spectinomycin [80 μg/ml] and ampicilline [100 μg/ml] and shaken in an Erlenmeyer flask overnight at 37° C., 180 rpm. The following day, a main culture of 1000 ml Terrific broth (TB) medium supplemented with 0.4-0.45% glycerol (Sigma, 49781), 10 mM MgCl2, tetracycline [20 μg/ml], spectinomycin [80 μg/ml] and ampicilline [100 μg/ml] was inoculated to a dilution of 0.1 optical density at $600_{nm}$($OD600_{nm}$), incubated in an Erlenmeyer flask at 180 rpm, 37° C. Recombinant polysaccharide was expressed constitutively, hemolysin A was induced with 0.6% arabinose from a pBAD promoter and PglB with 1 mM isopropyl-β-D-thiogalactopyranoside (IPTG) at an optical density $OD600_{nm}$ of 0.64 and shaken overnight at 180 rpm and 37° C. Cells were harvested, spun down at 4° C., 9000 rpm for 15 minutes and washed with 110 ml 0.9% sodium chloride and an equivalent of 4200 $OD600_{nm}$ were extracted by an osmotic shock procedure. Cells were resuspended in 14 ml ⅓×TBS (Tris buffered saline, Fisher Scientific) and 7 ml resuspension buffer (75% (w/v) sucrose, 30 mM EDTA, 600 mM Tris-HCl pH 8.5) and rotated for 30 minutes at 4° C. Cells were pelleted by centrifugation at 8000 rpm for 30 minutes at 4° C. and resuspended in 21 ml osmotic shock buffer (10 mM Tris-HCl pH 8.0) followed by another incubation of 30 minutes at 4° C. Cells were spun down again by centrifugation, supernatants were recovered and filtered with a 0.2 micrometer filter. 2 ml of the filtrate were supplemented with a 5M sodium chloride solution to a final concentration of 50 mM, the pH was set to 5.5 with 1M citric acid by adjusting the volume to 4 ml. The sample was spun down by centrifugation at 14000 rpm, at 4° C. for 5 minutes. A purification column was prepared (*Proteus* FliQ FPLC column; 1 ml; generon) with 1 ml of a cation exchange resin (Nuvia HR-S, Biorad) and equilibrated with 20 mM Citrate, 50 mM NaCl, pH 5.5 on an FPLC system (Aekta, Amersham Pharmacia). 2 ml of the sample was applied with a 2 ml superloop, the column was washed with 5 ml 20 mM Citrate, 50 mM NaCl, pH 5.5 and the bioconjugate was eluted applying a gradient to 20 mM Citrate, 500 mM NaCl, pH 5.5 in 10 column volumes. Flow-through and wash fractions collected were 500 microliter, elution fractions had a volume of 350 microliter. 45 microliter of the chromatography fractions were supplemented with 15 microliter 4 times concentrated Laemmli buffer to obtain a final concentration of 62.5 mM Tris-HCl pH 6.8, 2% (w/v) sodium dodecyl sulfate, 5% (w/v) beta-mercaptoethanol, 10% (v/v) glycerol, 0.005% (w/v) bromphenol blue. Samples were boiled at 95° C. for 15 minutes. 20 microliters thereof were separated by 4-12% SDS-PAGE (Nu-PAGE, 4-12% Bis-Tris Gel, life technologies) with MOPS running buffer (50 mM MOPS, 50 mM Tris Base, 0.1% SDS, 1 mM EDTA, pH 7.7) at 200 Volt for 45 minutes for the Western Blot shown in FIG. 10) A). Proteins were then transferred onto a nitrocellulose membrane using the iBLOT gel transfer stacks (Novex, by Life Technologies). The nitrocellulose was blocked with 10% (w/v) milk powder dissolved in PBST (10 mM phosphate buffer pH 7.5, 137 mM sodium chloride, 2.7 mM potassium chloride purchased from Ambresco E703-500 ml, 0.1%/v/v) tween) for 20 minutes at room temperature followed by an immunoblot detection using a primary rabbit anti-HIa antibody (polyclonal purified IgG, Glycovaxyn Nr 160) at 2.5 ug/ml in PBST for 1 hour at room temperature. The membrane was washed twice with PBST and incubated with a secondary goat anti-rabbit horse radish peroxidase (HRP) coupled antibody (Biorad, 170-6515) in PBST for 1 hour at room temperature. The membrane was washed 3 times with PBST for 5 minutes and protein bands were visualized by addition of TBM (TMB one component HRP membrane substrate) and the reaction was stopped with deionized water.

From the boiled samples, 40 microliters were loaded on a second 4-12% SDS-PAGE gel for SimplyBlues staining (Nu-PAGE, 4-12% Bis-Tris Gel, life technologies) and proteins were separated in MOPS running buffer (50 mM MOPS, 50 mM Tris Base, 0.1% SDS, 1 mM EDTA, pH 7.7) at 200 Volt for 45 minutes. The gel was stained two consecutive times with 10 ml SimplyBlue SafeStain (Life Technologies) followed by a destaining step using deionized water. The results are shown in FIG. 10.

The present disclosure is not to be limited in scope by the specific embodiments described herein. Indeed, various modifications of the subject matter provided herein, in addition to those described, will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

The invention claimed is:

1. An HIa protein comprising a first amino acid sequence being at least 80% identical to SEQ ID NO: 1, the HIa protein comprising: a) a substitution of histidine at position 48 of SEQ ID NO: 1 with cysteine, b) a substitution of glycine at position 122 of SEQ ID NO: 1 with cysteine, and c) optionally a substitution of histidine at position 35 of SEQ ID NO: 1.

2. The HIa protein of claim 1, the histidine at position 35 of SEQ ID NO: 1 being substituted.

3. The HIa protein of claim 1 comprising: A) D/E-X-N-Z-S/T (SEQ ID NO: 11), wherein X and Z are independently any amino acid apart from proline, or B) K-D/E-X-N-Z-S/T-K (SEQ ID NO: 12), wherein X and Z are independently any amino acid apart from proline.

4. The HIa protein of claim 1, the first amino acid sequence being at least 85% identical to the amino acid sequence of SEQ ID NO: 3.

5. The HIa protein of claim 1 further comprising a peptide tag optionally comprising a hex-histidine tag or a histidine-arginine repeat and optionally being at the C-terminus of the HIa protein.

6. The HIa protein of claim 5, the first amino acid sequence being at least 97% identical to any one of SEQ ID NOs: 5, 6, 9, or 10.

7. The HIa protein of claim 1 further comprising a signal sequence, which is capable of directing the HIa protein to the periplasm of a host cell, optionally the signal sequence being selected from any one of SEQ ID NOs: 13-21, and optionally the signal sequence being at the N-terminus of the HIa protein.

8. The HIa protein of claim 7 further comprising one or two amino acids between the signal sequence and the first amino acid sequence wherein optionally the HIa protein comprises a second amino acid sequence being at least 97% identical to SEQ ID NO: 5 or SEQ ID NO: 9.

9. The HIa protein of claim 1 further comprising one or two amino acids at the N-terminus of the HIa protein.

10. The HIa protein of claim 9 comprising a third amino acid sequence being at least 97% to SEQ ID NO: 6 or SEQ ID NO: 10.

11. A conjugate comprising an antigen and the HIa protein of claim 1, wherein the HIa protein is linked to the antigen.

12. A polynucleotide encoding the HIa protein of claim 1.

13. A vector comprising the polynucleotide of claim 12.

14. A host cell comprising:

i) one or more nucleic acids that encode glycosyltransferase(s);

ii) a nucleic acid that encodes an oligosaccharyl transferase;

iii) a nucleic acid that encodes the HIa protein according to claim 1;

and optionally iv) a nucleic acid that encodes a polymerase.

15. A method comprising (i) culturing the host cell of claim 14 under conditions suitable for the production of proteins, thereby producing a composition comprising the host cell and a bioconjugate comprising a saccharide and the HIa protein, the HIa protein being linked to the saccharide, and (ii) isolating the bioconjugate from the host cell.

16. A bioconjugate produced by the method of claim 15, wherein said bioconjugate comprises a saccharide linked to a HIa protein.

17. An immunogenic composition comprising an immunologically effective amount of the HIa protein of claim 1.

18. The immunogenic composition of claim 17 further comprising a pharmaceutically acceptable excipient or carrier.

19. A method for the treatment of *Staphylococcus aureus* infection in a subject in need thereof, the method comprising administering to the subject a therapeutically effective amount of the HIa protein of claim 1.

20. A method of inducing an immune response to *Staphylococcus aureus* in a subject, the method comprising administering to the subject an effective amount to induce the immune response of the HIa protein of claim 1.

* * * * *

SEQUENCE LISTING

```
<160> NUMBER OF SEQ ID NOS: 30

<210> SEQ ID NO 1
<211> LENGTH: 293
<212> TYPE: PRT
```

<213> ORGANISM: Staphylococcus aureus

<400> SEQUENCE: 1

Ala Asp Ser Asp Ile Asn Ile Lys Thr Gly Thr Thr Asp Ile Gly Ser
1 5 10 15

Asn Thr Thr Val Lys Thr Gly Asp Leu Val Thr Tyr Asp Lys Glu Asn
20 25 30

Gly Met His Lys Lys Val Phe Tyr Ser Phe Ile Asp Asp Lys Asn His
35 40 45

Asn Lys Lys Leu Leu Val Ile Arg Thr Lys Gly Thr Ile Ala Gly Gln
50 55 60

Tyr Arg Val Tyr Ser Glu Glu Gly Ala Asn Lys Ser Gly Leu Ala Trp
65 70 75 80

Pro Ser Ala Phe Lys Val Gln Leu Gln Leu Pro Asp Asn Glu Val Ala
85 90 95

Gln Ile Ser Asp Tyr Tyr Pro Arg Asn Ser Ile Asp Thr Lys Glu Tyr
100 105 110

Met Ser Thr Leu Thr Tyr Gly Phe Asn Gly Asn Val Thr Gly Asp Asp
115 120 125

Thr Gly Lys Ile Gly Gly Leu Ile Gly Ala Asn Val Ser Ile Gly His
130 135 140

Thr Leu Lys Tyr Val Gln Pro Asp Phe Lys Thr Ile Leu Glu Ser Pro
145 150 155 160

Thr Asp Lys Lys Val Gly Trp Lys Val Ile Phe Asn Asn Met Val Asn
165 170 175

Gln Asn Trp Gly Pro Tyr Asp Arg Asp Ser Trp Asn Pro Val Tyr Gly
180 185 190

Asn Gln Leu Phe Met Lys Thr Arg Asn Gly Ser Met Lys Ala Ala Asp
195 200 205

Asn Phe Leu Asp Pro Asn Lys Ala Ser Ser Leu Leu Ser Ser Gly Phe
210 215 220

Ser Pro Asp Phe Ala Thr Val Ile Thr Met Asp Arg Lys Ala Ser Lys
225 230 235 240

Gln Gln Thr Asn Ile Asp Val Ile Tyr Glu Arg Val Arg Asp Asp Tyr
245 250 255

Gln Leu His Trp Thr Ser Thr Asn Trp Lys Gly Thr Asn Thr Lys Asp
260 265 270

Lys Trp Ile Asp Arg Ser Ser Glu Arg Tyr Lys Ile Asp Trp Glu Lys
275 280 285

Glu Glu Met Thr Asn
290

<210> SEQ ID NO 2
<211> LENGTH: 293
<212> TYPE: PRT
<213> ORGANISM: Artificial Sequence
<220> FEATURE:
<223> OTHER INFORMATION: Amino acid sequence of mature Hla H48C/G122C

<400> SEQUENCE: 2

Ala Asp Ser Asp Ile Asn Ile Lys Thr Gly Thr Thr Asp Ile Gly Ser
1 5 10 15

Asn Thr Thr Val Lys Thr Gly Asp Leu Val Thr Tyr Asp Lys Glu Asn
20 25 30

Gly Met His Lys Lys Val Phe Tyr Ser Phe Ile Asp Asp Lys Asn Cys
35 40 45

Asn Lys Lys Leu Leu Val Ile Arg Thr Lys Gly Thr Ile Ala Gly Gln
50 55 60

Tyr Arg Val Tyr Ser Glu Glu Gly Ala Asn Lys Ser Gly Leu Ala Trp
65 70 75 80

Pro Ser Ala Phe Lys Val Gln Leu Gln Leu Pro Asp Asn Glu Val Ala
85 90 95

Gln Ile Ser Asp Tyr Tyr Pro Arg Asn Ser Ile Asp Thr Lys Glu Tyr
100 105 110

Met Ser Thr Leu Thr Tyr Gly Phe Asn Cys Asn Val Thr Gly Asp Asp
115 120 125

Thr Gly Lys Ile Gly Gly Leu Ile Gly Ala Asn Val Ser Ile Gly His
130 135 140

Thr Leu Lys Tyr Val Gln Pro Asp Phe Lys Thr Ile Leu Glu Ser Pro
145 150 155 160

Thr Asp Lys Lys Val Gly Trp Lys Val Ile Phe Asn Asn Met Val Asn
165 170 175

Gln Asn Trp Gly Pro Tyr Asp Arg Asp Ser Trp Asn Pro Val Tyr Gly
180 185 190

Asn Gln Leu Phe Met Lys Thr Arg Asn Gly Ser Met Lys Ala Ala Asp
195 200 205

Asn Phe Leu Asp Pro Asn Lys Ala Ser Ser Leu Leu Ser Ser Gly Phe
210 215 220

Ser Pro Asp Phe Ala Thr Val Ile Thr Met Asp Arg Lys Ala Ser Lys
225 230 235 240

Gln Gln Thr Asn Ile Asp Val Ile Tyr Glu Arg Val Arg Asp Asp Tyr
245 250 255

Gln Leu His Trp Thr Ser Thr Asn Trp Lys Gly Thr Asn Thr Lys Asp
260 265 270

Lys Trp Ile Asp Arg Ser Ser Glu Arg Tyr Lys Ile Asp Trp Glu Lys
275 280 285

Glu Glu Met Thr Asn
290

<210> SEQ ID NO 3
<211> LENGTH: 293
<212> TYPE: PRT
<213> ORGANISM: Artificial Sequence
<220> FEATURE:
<223> OTHER INFORMATION: Amino acid sequence of mature Hla H35L/H48C/G122C

<400> SEQUENCE: 3

Ala Asp Ser Asp Ile Asn Ile Lys Thr Gly Thr Thr Asp Ile Gly Ser
1 5 10 15

Asn Thr Thr Val Lys Thr Gly Asp Leu Val Thr Tyr Asp Lys Glu Asn
20 25 30

Gly Met Leu Lys Lys Val Phe Tyr Ser Phe Ile Asp Asp Lys Asn Cys
35 40 45

Asn Lys Lys Leu Leu Val Ile Arg Thr Lys Gly Thr Ile Ala Gly Gln
50 55 60

Tyr Arg Val Tyr Ser Glu Glu Gly Ala Asn Lys Ser Gly Leu Ala Trp
65 70 75 80

Pro Ser Ala Phe Lys Val Gln Leu Gln Leu Pro Asp Asn Glu Val Ala
85 90 95

Gln Ile Ser Asp Tyr Tyr Pro Arg Asn Ser Ile Asp Thr Lys Glu Tyr

```
            100                 105                 110

Met Ser Thr Leu Thr Tyr Gly Phe Asn Cys Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290


<210> SEQ ID NO 4
<211> LENGTH: 313
<212> TYPE: PRT
<213> ORGANISM: Artificial Sequence
<220> FEATURE:
<223> OTHER INFORMATION: Amino acid sequence of Hla H35L/H48C/G122C with
      N-terminal S and Flgl signal sequence

<400> SEQUENCE: 4

Met Ile Lys Phe Leu Ser Ala Leu Ile Leu Leu Leu Val Thr Thr Ala
1               5                   10                  15

Ala Gln Ala Ser Ala Asp Ser Asp Ile Asn Ile Lys Thr Gly Thr Thr
            20                  25                  30

Asp Ile Gly Ser Asn Thr Thr Val Lys Thr Gly Asp Leu Val Thr Tyr
        35                  40                  45

Asp Lys Glu Asn Gly Met Leu Lys Lys Val Phe Tyr Ser Phe Ile Asp
    50                  55                  60

Asp Lys Asn Cys Asn Lys Lys Leu Leu Val Ile Arg Thr Lys Gly Thr
65                  70                  75                  80

Ile Ala Gly Gln Tyr Arg Val Tyr Ser Glu Glu Gly Ala Asn Lys Ser
                85                  90                  95

Gly Leu Ala Trp Pro Ser Ala Phe Lys Val Gln Leu Gln Leu Pro Asp
            100                 105                 110

Asn Glu Val Ala Gln Ile Ser Asp Tyr Tyr Pro Arg Asn Ser Ile Asp
        115                 120                 125

Thr Lys Glu Tyr Met Ser Thr Leu Thr Tyr Gly Phe Asn Cys Asn Val
    130                 135                 140

Thr Gly Asp Asp Thr Gly Lys Ile Gly Gly Leu Ile Gly Ala Asn Val
145                 150                 155                 160
```

-continued

```
Ser Ile Gly His Thr Leu Lys Tyr Val Gln Pro Asp Phe Lys Thr Ile
                165                 170                 175

Leu Glu Ser Pro Thr Asp Lys Lys Val Gly Trp Lys Val Ile Phe Asn
            180                 185                 190

Asn Met Val Asn Gln Asn Trp Gly Pro Tyr Asp Arg Asp Ser Trp Asn
        195                 200                 205

Pro Val Tyr Gly Asn Gln Leu Phe Met Lys Thr Arg Asn Gly Ser Met
    210                 215                 220

Lys Ala Ala Asp Asn Phe Leu Asp Pro Asn Lys Ala Ser Ser Leu Leu
225                 230                 235                 240

Ser Ser Gly Phe Ser Pro Asp Phe Ala Thr Val Ile Thr Met Asp Arg
                245                 250                 255

Lys Ala Ser Lys Gln Gln Thr Asn Ile Asp Val Ile Tyr Glu Arg Val
            260                 265                 270

Arg Asp Asp Tyr Gln Leu His Trp Thr Ser Thr Asn Trp Lys Gly Thr
        275                 280                 285

Asn Thr Lys Asp Lys Trp Ile Asp Arg Ser Ser Glu Arg Tyr Lys Ile
    290                 295                 300

Asp Trp Glu Lys Glu Glu Met Thr Asn
305                 310


<210> SEQ ID NO 5
<211> LENGTH: 319
<212> TYPE: PRT
<213> ORGANISM: Artificial Sequence
<220> FEATURE:
<223> OTHER INFORMATION: Amino acid sequence of Hla H35L/H48C/G122C with
      N-terminal S and Flgl signal sequence and C-terminal GSHRHR

<400> SEQUENCE: 5

Met Ile Lys Phe Leu Ser Ala Leu Ile Leu Leu Leu Val Thr Thr Ala
1               5                   10                  15

Ala Gln Ala Ser Ala Asp Ser Asp Ile Asn Ile Lys Thr Gly Thr Thr
            20                  25                  30

Asp Ile Gly Ser Asn Thr Thr Val Lys Thr Gly Asp Leu Val Thr Tyr
        35                  40                  45

Asp Lys Glu Asn Gly Met Leu Lys Lys Val Phe Tyr Ser Phe Ile Asp
    50                  55                  60

Asp Lys Asn Cys Asn Lys Lys Leu Leu Val Ile Arg Thr Lys Gly Thr
65                  70                  75                  80

Ile Ala Gly Gln Tyr Arg Val Tyr Ser Glu Glu Gly Ala Asn Lys Ser
                85                  90                  95

Gly Leu Ala Trp Pro Ser Ala Phe Lys Val Gln Leu Gln Leu Pro Asp
            100                 105                 110

Asn Glu Val Ala Gln Ile Ser Asp Tyr Tyr Pro Arg Asn Ser Ile Asp
        115                 120                 125

Thr Lys Glu Tyr Met Ser Thr Leu Thr Tyr Gly Phe Asn Cys Asn Val
    130                 135                 140

Thr Gly Asp Asp Thr Gly Lys Ile Gly Gly Leu Ile Gly Ala Asn Val
145                 150                 155                 160

Ser Ile Gly His Thr Leu Lys Tyr Val Gln Pro Asp Phe Lys Thr Ile
                165                 170                 175

Leu Glu Ser Pro Thr Asp Lys Lys Val Gly Trp Lys Val Ile Phe Asn
            180                 185                 190

Asn Met Val Asn Gln Asn Trp Gly Pro Tyr Asp Arg Asp Ser Trp Asn
        195                 200                 205
```

```
Pro Val Tyr Gly Asn Gln Leu Phe Met Lys Thr Arg Asn Gly Ser Met
    210                 215                 220

Lys Ala Ala Asp Asn Phe Leu Asp Pro Asn Lys Ala Ser Ser Leu Leu
225                 230                 235                 240

Ser Ser Gly Phe Ser Pro Asp Phe Ala Thr Val Ile Thr Met Asp Arg
                245                 250                 255

Lys Ala Ser Lys Gln Gln Thr Asn Ile Asp Val Ile Tyr Glu Arg Val
            260                 265                 270

Arg Asp Asp Tyr Gln Leu His Trp Thr Ser Thr Asn Trp Lys Gly Thr
        275                 280                 285

Asn Thr Lys Asp Lys Trp Ile Asp Arg Ser Ser Glu Arg Tyr Lys Ile
    290                 295                 300

Asp Trp Glu Lys Glu Glu Met Thr Asn Gly Ser His Arg His Arg
305                 310                 315


<210> SEQ ID NO 6
<211> LENGTH: 300
<212> TYPE: PRT
<213> ORGANISM: Artificial Sequence
<220> FEATURE:
<223> OTHER INFORMATION: Amino acid sequence of Hla H35L/H48C/G122C with
      N-terminal S and C-terminal GSHRHR

<400> SEQUENCE: 6

Ser Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met Leu Lys Lys Val Phe Tyr Ser Phe Ile Asp Asp Lys Asn
        35                  40                  45

Cys Asn Lys Lys Leu Leu Val Ile Arg Thr Lys Gly Thr Ile Ala Gly
    50                  55                  60

Gln Tyr Arg Val Tyr Ser Glu Glu Gly Ala Asn Lys Ser Gly Leu Ala
65                  70                  75                  80

Trp Pro Ser Ala Phe Lys Val Gln Leu Gln Leu Pro Asp Asn Glu Val
                85                  90                  95

Ala Gln Ile Ser Asp Tyr Tyr Pro Arg Asn Ser Ile Asp Thr Lys Glu
            100                 105                 110

Tyr Met Ser Thr Leu Thr Tyr Gly Phe Asn Cys Asn Val Thr Gly Asp
        115                 120                 125

Asp Thr Gly Lys Ile Gly Gly Leu Ile Gly Ala Asn Val Ser Ile Gly
    130                 135                 140

His Thr Leu Lys Tyr Val Gln Pro Asp Phe Lys Thr Ile Leu Glu Ser
145                 150                 155                 160

Pro Thr Asp Lys Lys Val Gly Trp Lys Val Ile Phe Asn Asn Met Val
                165                 170                 175

Asn Gln Asn Trp Gly Pro Tyr Asp Arg Asp Ser Trp Asn Pro Val Tyr
            180                 185                 190

Gly Asn Gln Leu Phe Met Lys Thr Arg Asn Gly Ser Met Lys Ala Ala
        195                 200                 205

Asp Asn Phe Leu Asp Pro Asn Lys Ala Ser Ser Leu Leu Ser Ser Gly
    210                 215                 220

Phe Ser Pro Asp Phe Ala Thr Val Ile Thr Met Asp Arg Lys Ala Ser
225                 230                 235                 240

Lys Gln Gln Thr Asn Ile Asp Val Ile Tyr Glu Arg Val Arg Asp Asp
```

-continued

```
                245                 250                 255

Tyr Gln Leu His Trp Thr Ser Thr Asn Trp Lys Gly Thr Asn Thr Lys
            260                 265                 270

Asp Lys Trp Ile Asp Arg Ser Ser Glu Arg Tyr Lys Ile Asp Trp Glu
        275                 280                 285

Lys Glu Glu Met Thr Asn Gly Ser His Arg His Arg
    290                 295                 300


<210> SEQ ID NO 7
<211> LENGTH: 299
<212> TYPE: PRT
<213> ORGANISM: Artificial Sequence
<220> FEATURE:
<223> OTHER INFORMATION: Amino acid sequence of mature Hla
      H35L/H48C/G122C with KDQNRTK substitution for residue K131

<400> SEQUENCE: 7

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn Cys
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Cys Asn Val Thr Gly Asp Asp
        115                 120                 125

Thr Gly Lys Asp Gln Asn Arg Thr Lys Ile Gly Gly Leu Ile Gly Ala
    130                 135                 140

Asn Val Ser Ile Gly His Thr Leu Lys Tyr Val Gln Pro Asp Phe Lys
145                 150                 155                 160

Thr Ile Leu Glu Ser Pro Thr Asp Lys Lys Val Gly Trp Lys Val Ile
                165                 170                 175

Phe Asn Asn Met Val Asn Gln Asn Trp Gly Pro Tyr Asp Arg Asp Ser
            180                 185                 190

Trp Asn Pro Val Tyr Gly Asn Gln Leu Phe Met Lys Thr Arg Asn Gly
        195                 200                 205

Ser Met Lys Ala Ala Asp Asn Phe Leu Asp Pro Asn Lys Ala Ser Ser
    210                 215                 220

Leu Leu Ser Ser Gly Phe Ser Pro Asp Phe Ala Thr Val Ile Thr Met
225                 230                 235                 240

Asp Arg Lys Ala Ser Lys Gln Gln Thr Asn Ile Asp Val Ile Tyr Glu
                245                 250                 255

Arg Val Arg Asp Asp Tyr Gln Leu His Trp Thr Ser Thr Asn Trp Lys
            260                 265                 270

Gly Thr Asn Thr Lys Asp Lys Trp Ile Asp Arg Ser Ser Glu Arg Tyr
        275                 280                 285

Lys Ile Asp Trp Glu Lys Glu Glu Met Thr Asn
    290                 295
```

<210> SEQ ID NO 8
<211> LENGTH: 319
<212> TYPE: PRT
<213> ORGANISM: Artificial Sequence
<220> FEATURE:
<223> OTHER INFORMATION: Amino acid sequence of Hla H35L/H48C/G122C with N-terminal S, Flgl signal sequence, and KDQNRTK substitution for residue K131

<400> SEQUENCE: 8

```
Met Ile Lys Phe Leu Ser Ala Leu Ile Leu Leu Leu Val Thr Thr Ala
1               5                   10                  15

Ala Gln Ala Ser Ala Asp Ser Asp Ile Asn Ile Lys Thr Gly Thr Thr
            20                  25                  30

Asp Ile Gly Ser Asn Thr Thr Val Lys Thr Gly Asp Leu Val Thr Tyr
        35                  40                  45

Asp Lys Glu Asn Gly Met Leu Lys Lys Val Phe Tyr Ser Phe Ile Asp
    50                  55                  60

Asp Lys Asn Cys Asn Lys Lys Leu Leu Val Ile Arg Thr Lys Gly Thr
65                  70                  75                  80

Ile Ala Gly Gln Tyr Arg Val Tyr Ser Glu Glu Gly Ala Asn Lys Ser
                85                  90                  95

Gly Leu Ala Trp Pro Ser Ala Phe Lys Val Gln Leu Gln Leu Pro Asp
            100                 105                 110

Asn Glu Val Ala Gln Ile Ser Asp Tyr Tyr Pro Arg Asn Ser Ile Asp
        115                 120                 125

Thr Lys Glu Tyr Met Ser Thr Leu Thr Tyr Gly Phe Asn Cys Asn Val
    130                 135                 140

Thr Gly Asp Asp Thr Gly Lys Asp Gln Asn Arg Thr Lys Ile Gly Gly
145                 150                 155                 160

Leu Ile Gly Ala Asn Val Ser Ile Gly His Thr Leu Lys Tyr Val Gln
                165                 170                 175

Pro Asp Phe Lys Thr Ile Leu Glu Ser Pro Thr Asp Lys Lys Val Gly
            180                 185                 190

Trp Lys Val Ile Phe Asn Asn Met Val Asn Gln Asn Trp Gly Pro Tyr
        195                 200                 205

Asp Arg Asp Ser Trp Asn Pro Val Tyr Gly Asn Gln Leu Phe Met Lys
    210                 215                 220

Thr Arg Asn Gly Ser Met Lys Ala Ala Asp Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
            260                 265                 270

Val Ile Tyr Glu Arg Val Arg Asp Asp Tyr Gln Leu His Trp Thr Ser
        275                 280                 285

Thr Asn Trp Lys Gly Thr Asn Thr Lys Asp Lys Trp Ile Asp Arg Ser
    290                 295                 300

Ser Glu Arg Tyr Lys Ile Asp Trp Glu Lys Glu Glu Met Thr Asn
305                 310                 315
```

<210> SEQ ID NO 9
<211> LENGTH: 325
<212> TYPE: PRT
<213> ORGANISM: Artificial Sequence
<220> FEATURE:
<223> OTHER INFORMATION: Amino acid sequence of Hla H35L/H48C/G122C with N-terminal S, Flgl signal sequence, C-terminal GSHRHR, and KDQNRTK substitution for residue K131

<400> SEQUENCE: 9

```
Met Ile Lys Phe Leu Ser Ala Leu Ile Leu Leu Leu Val Thr Thr Ala
1               5                   10                  15

Ala Gln Ala Ser Ala Asp Ser Asp Ile Asn Ile Lys Thr Gly Thr Thr
            20                  25                  30

Asp Ile Gly Ser Asn Thr Thr Val Lys Thr Gly Asp Leu Val Thr Tyr
        35                  40                  45

Asp Lys Glu Asn Gly Met Leu Lys Lys Val Phe Tyr Ser Phe Ile Asp
    50                  55                  60

Asp Lys Asn Cys Asn Lys Lys Leu Leu Val Ile Arg Thr Lys Gly Thr
65                  70                  75                  80

Ile Ala Gly Gln Tyr Arg Val Tyr Ser Glu Glu Gly Ala Asn Lys Ser
                85                  90                  95

Gly Leu Ala Trp Pro Ser Ala Phe Lys Val Gln Leu Gln Leu Pro Asp
            100                 105                 110

Asn Glu Val Ala Gln Ile Ser Asp Tyr Tyr Pro Arg Asn Ser Ile Asp
        115                 120                 125

Thr Lys Glu Tyr Met Ser Thr Leu Thr Tyr Gly Phe Asn Cys Asn Val
    130                 135                 140

Thr Gly Asp Asp Thr Gly Lys Asp Gln Asn Arg Thr Lys Ile Gly Gly
145                 150                 155                 160

Leu Ile Gly Ala Asn Val Ser Ile Gly His Thr Leu Lys Tyr Val Gln
                165                 170                 175

Pro Asp Phe Lys Thr Ile Leu Glu Ser Pro Thr Asp Lys Lys Val Gly
            180                 185                 190

Trp Lys Val Ile Phe Asn Asn Met Val Asn Gln Asn Trp Gly Pro Tyr
        195                 200                 205

Asp Arg Asp Ser Trp Asn Pro Val Tyr Gly Asn Gln Leu Phe Met Lys
    210                 215                 220

Thr Arg Asn Gly Ser Met Lys Ala Ala Asp Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
            260                 265                 270

Val Ile Tyr Glu Arg Val Arg Asp Asp Tyr Gln Leu His Trp Thr Ser
        275                 280                 285

Thr Asn Trp Lys Gly Thr Asn Thr Lys Asp Lys Trp Ile Asp Arg Ser
    290                 295                 300

Ser Glu Arg Tyr Lys Ile Asp Trp Glu Lys Glu Glu Met Thr Asn Gly
305                 310                 315                 320

Ser His Arg His Arg
                325
```

<210> SEQ ID NO 10
<211> LENGTH: 306
<212> TYPE: PRT
<213> ORGANISM: Artificial Sequence
<220> FEATURE:
<223> OTHER INFORMATION: Amino acid sequence of Hla H35L/H48C/G122C with N-terminal S, C-terminal GSHRHR, and KDQNRTK substitution for residue K131

<400> SEQUENCE: 10

```
Ser Ala Asp Ser Asp Ile Asn Ile Lys Thr Gly Thr Thr Asp Ile Gly
1               5                   10                  15

Ser Asn Thr Thr Val Lys Thr Gly Asp Leu Val Thr Tyr Asp Lys Glu
            20                  25                  30

Asn Gly Met Leu Lys Lys Val Phe Tyr Ser Phe Ile Asp Asp Lys Asn
        35                  40                  45

Cys Asn Lys Lys Leu Leu Val Ile Arg Thr Lys Gly Thr Ile Ala Gly
    50                  55                  60

Gln Tyr Arg Val Tyr Ser Glu Glu Gly Ala Asn Lys Ser Gly Leu Ala
65                  70                  75                  80

Trp Pro Ser Ala Phe Lys Val Gln Leu Gln Leu Pro Asp Asn Glu Val
                85                  90                  95

Ala Gln Ile Ser Asp Tyr Tyr Pro Arg Asn Ser Ile Asp Thr Lys Glu
            100                 105                 110

Tyr Met Ser Thr Leu Thr Tyr Gly Phe Asn Cys Asn Val Thr Gly Asp
        115                 120                 125

Asp Thr Gly Lys Asp Gln Asn Arg Thr Lys Ile Gly Gly Leu Ile Gly
    130                 135                 140

Ala Asn Val Ser Ile Gly His Thr Leu Lys Tyr Val Gln Pro Asp Phe
145                 150                 155                 160

Lys Thr Ile Leu Glu Ser Pro Thr Asp Lys Lys Val Gly Trp Lys Val
                165                 170                 175

Ile Phe Asn Asn Met Val Asn Gln Asn Trp Gly Pro Tyr Asp Arg Asp
            180                 185                 190

Ser Trp Asn Pro Val Tyr Gly Asn Gln Leu Phe Met Lys Thr Arg Asn
        195                 200                 205

Gly Ser Met Lys Ala Ala Asp Asn Phe Leu Asp Pro Asn Lys Ala Ser
    210                 215                 220

Ser Leu Leu Ser Ser Gly Phe Ser Pro Asp Phe Ala Thr Val Ile Thr
225                 230                 235                 240

Met Asp Arg Lys Ala Ser Lys Gln Gln Thr Asn Ile Asp Val Ile Tyr
                245                 250                 255

Glu Arg Val Arg Asp Asp Tyr Gln Leu His Trp Thr Ser Thr Asn Trp
            260                 265                 270

Lys Gly Thr Asn Thr Lys Asp Lys Trp Ile Asp Arg Ser Ser Glu Arg
        275                 280                 285

Tyr Lys Ile Asp Trp Glu Lys Glu Glu Met Thr Asn Gly Ser His Arg
    290                 295                 300

His Arg
305
```

```
<210> SEQ ID NO 11
<211> LENGTH: 5
<212> TYPE: PRT
<213> ORGANISM: Artificial Sequence
<220> FEATURE:
<223> OTHER INFORMATION: glycosite
<220> FEATURE:
<221> NAME/KEY: MOD_RES
<222> LOCATION: (1)..(1)
<223> OTHER INFORMATION: Xaa can be Asp or Glu
<220> FEATURE:
<221> NAME/KEY: MOD_RES
<222> LOCATION: (2)..(2)
<223> OTHER INFORMATION: Xaa can be any naturally occurring amino acid
      except proline
<220> FEATURE:
<221> NAME/KEY: MOD_RES
```

```
<222> LOCATION: (4)..(4)
<223> OTHER INFORMATION: Xaa can be any naturally occurring amino acid
      except proline
<220> FEATURE:
<221> NAME/KEY: MOD_RES
<222> LOCATION: (5)..(5)
<223> OTHER INFORMATION: Xaa can be Ser or Thr

<400> SEQUENCE: 11

Xaa Xaa Asn Xaa Xaa
1               5


<210> SEQ ID NO 12
<211> LENGTH: 7
<212> TYPE: PRT
<213> ORGANISM: Artificial Sequence
<220> FEATURE:
<223> OTHER INFORMATION: glycosite
<220> FEATURE:
<221> NAME/KEY: MOD_RES
<222> LOCATION: (2)..(2)
<223> OTHER INFORMATION: Xaa can be Asp or Glu
<220> FEATURE:
<221> NAME/KEY: MOD_RES
<222> LOCATION: (3)..(3)
<223> OTHER INFORMATION: Xaa can be any naturally occurring amino acid
      except proline
<220> FEATURE:
<221> NAME/KEY: MOD_RES
<222> LOCATION: (5)..(5)
<223> OTHER INFORMATION: Xaa can be any naturally occurring amino acid
      except proline
<220> FEATURE:
<221> NAME/KEY: MOD_RES
<222> LOCATION: (6)..(6)
<223> OTHER INFORMATION: Xaa can be Ser or Thr

<400> SEQUENCE: 12

Lys Xaa Xaa Asn Xaa Xaa Lys
1               5


<210> SEQ ID NO 13
<211> LENGTH: 19
<212> TYPE: PRT
<213> ORGANISM: Escherichia coli

<400> SEQUENCE: 13

Met Ile Lys Phe Leu Ser Ala Leu Ile Leu Leu Leu Val Thr Thr Ala
1               5                   10                  15

Ala Gln Ala


<210> SEQ ID NO 14
<211> LENGTH: 21
<212> TYPE: PRT
<213> ORGANISM: Escherichia coli

<400> SEQUENCE: 14

Met Lys Lys Thr Ala Ile Ala Ile Ala Val Ala Leu Ala Gly Phe Ala
1               5                   10                  15

Thr Val Ala Gln Ala
            20


<210> SEQ ID NO 15
<211> LENGTH: 26
<212> TYPE: PRT
<213> ORGANISM: Escherichia coli

<400> SEQUENCE: 15
```

-continued

Met Lys Ile Lys Thr Gly Ala Arg Ile Leu Ala Leu Ser Ala Leu Thr
1 5 10 15

Thr Met Met Phe Ser Ala Ser Ala Leu Ala
20 25

<210> SEQ ID NO 16
<211> LENGTH: 22
<212> TYPE: PRT
<213> ORGANISM: Erwinia carotovora

<400> SEQUENCE: 16

Met Lys Tyr Leu Leu Pro Thr Ala Ala Ala Gly Leu Leu Leu Leu Ala
1 5 10 15

Ala Gln Pro Ala Met Ala
20

<210> SEQ ID NO 17
<211> LENGTH: 23
<212> TYPE: PRT
<213> ORGANISM: Escherichia coli

<400> SEQUENCE: 17

Met Ser Phe Lys Lys Ile Ile Lys Ala Phe Val Ile Met Ala Ala Leu
1 5 10 15

Val Ser Val Gln Ala His Ala
20

<210> SEQ ID NO 18
<211> LENGTH: 28
<212> TYPE: PRT
<213> ORGANISM: Bacillus subtilis

<400> SEQUENCE: 18

Met Phe Lys Phe Lys Lys Lys Phe Leu Val Gly Leu Thr Ala Ala Phe
1 5 10 15

Met Ser Ile Ser Met Phe Ser Ala Thr Ala Ser Ala
20 25

<210> SEQ ID NO 19
<211> LENGTH: 19
<212> TYPE: PRT
<213> ORGANISM: Escherichia coli

<400> SEQUENCE: 19

Met Lys Lys Ile Trp Leu Ala Leu Ala Gly Leu Val Leu Ala Phe Ser
1 5 10 15

Ala Ser Ala

<210> SEQ ID NO 20
<211> LENGTH: 21
<212> TYPE: PRT
<213> ORGANISM: Escherichia coli

<400> SEQUENCE: 20

Met Lys Gln Ala Leu Arg Val Ala Phe Gly Phe Leu Ile Leu Trp Ala
1 5 10 15

Ser Val Leu His Ala
20

<210> SEQ ID NO 21
<211> LENGTH: 26
<212> TYPE: PRT

```
<213> ORGANISM: Escherichia coli

<400> SEQUENCE: 21

Met Lys Met Asn Lys Lys Val Leu Leu Thr Ser Thr Met Ala Ala Ser
1               5                   10                  15

Leu Leu Ser Val Ala Ser Val Gln Ala Ser
            20                  25


<210> SEQ ID NO 22
<211> LENGTH: 305
<212> TYPE: PRT
<213> ORGANISM: Artificial Sequence
<220> FEATURE:
<223> OTHER INFORMATION: Amino acid sequence of mature Hla
      H35L/H48C/G122C with C-terminal GSHRHR and KDQNRTK substitution
      for residue K131

<400> SEQUENCE: 22

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn Cys
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Cys Asn Val Thr Gly Asp Asp
        115                 120                 125

Thr Gly Lys Asp Gln Asn Arg Thr Lys Ile Gly Gly Leu Ile Gly Ala
    130                 135                 140

Asn Val Ser Ile Gly His Thr Leu Lys Tyr Val Gln Pro Asp Phe Lys
145                 150                 155                 160

Thr Ile Leu Glu Ser Pro Thr Asp Lys Lys Val Gly Trp Lys Val Ile
                165                 170                 175

Phe Asn Asn Met Val Asn Gln Asn Trp Gly Pro Tyr Asp Arg Asp Ser
            180                 185                 190

Trp Asn Pro Val Tyr Gly Asn Gln Leu Phe Met Lys Thr Arg Asn Gly
        195                 200                 205

Ser Met Lys Ala Ala Asp Asn Phe Leu Asp Pro Asn Lys Ala Ser Ser
    210                 215                 220

Leu Leu Ser Ser Gly Phe Ser Pro Asp Phe Ala Thr Val Ile Thr Met
225                 230                 235                 240

Asp Arg Lys Ala Ser Lys Gln Gln Thr Asn Ile Asp Val Ile Tyr Glu
                245                 250                 255

Arg Val Arg Asp Asp Tyr Gln Leu His Trp Thr Ser Thr Asn Trp Lys
            260                 265                 270

Gly Thr Asn Thr Lys Asp Lys Trp Ile Asp Arg Ser Ser Glu Arg Tyr
        275                 280                 285

Lys Ile Asp Trp Glu Lys Glu Glu Met Thr Asn Gly Ser His Arg His
    290                 295                 300
```

Arg
305

<210> SEQ ID NO 23
<211> LENGTH: 7
<212> TYPE: PRT
<213> ORGANISM: Artificial Sequence
<220> FEATURE:
<223> OTHER INFORMATION: KDQNRTK glycosite

<400> SEQUENCE: 23

Lys Asp Gln Asn Arg Thr Lys
1               5

<210> SEQ ID NO 24
<211> LENGTH: 7
<212> TYPE: PRT
<213> ORGANISM: Artificial Sequence
<220> FEATURE:
<223> OTHER INFORMATION: KDQNATK glycosite

<400> SEQUENCE: 24

Lys Asp Gln Asn Arg Thr Lys
1               5

<210> SEQ ID NO 25
<211> LENGTH: 4
<212> TYPE: PRT
<213> ORGANISM: Artificial Sequence
<220> FEATURE:
<223> OTHER INFORMATION: HRHR C-terminal tag

<400> SEQUENCE: 25

His Arg His Arg
1

<210> SEQ ID NO 26
<211> LENGTH: 6
<212> TYPE: PRT
<213> ORGANISM: Artificial Sequence
<220> FEATURE:
<223> OTHER INFORMATION: GSHRHR C-terminal tag

<400> SEQUENCE: 26

Gly Ser His Arg His Arg
1               5

<210> SEQ ID NO 27
<211> LENGTH: 293
<212> TYPE: PRT
<213> ORGANISM: Artificial Sequence
<220> FEATURE:
<223> OTHER INFORMATION: Mature Hla H35L/Y102C/G126C

<400> SEQUENCE: 27

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

```
Pro Ser Ala Phe Lys Val Gln Leu Gln Leu Pro Asp Asn Glu Val Ala
                85                  90                  95

Gln Ile Ser Asp Tyr Cys Pro Arg Asn Ser Ile Asp Thr Lys Glu Tyr
            100                 105                 110

Met Ser Thr Leu Thr Tyr Gly Phe Asn Gly Asn Val Thr Cys Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290
```

<210> SEQ ID NO 28
<211> LENGTH: 293
<212> TYPE: PRT
<213> ORGANISM: Artificial Sequence
<220> FEATURE:
<223> OTHER INFORMATION: Mature HlaH35L/G122C/H48C

<400> SEQUENCE: 28

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn Cys
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Cys Asn Val Thr Gly Asp Asp
        115                 120                 125

Thr Gly Lys Ile Gly Gly Leu Ile Gly Ala Asn Val Ser Ile Gly His
    130                 135                 140
```

-continued

Thr Leu Lys Tyr Val Gln Pro Asp Phe Lys Thr Ile Leu Glu Ser Pro
145 150 155 160

Thr Asp Lys Lys Val Gly Trp Lys Val Ile Phe Asn Asn Met Val Asn
165 170 175

Gln Asn Trp Gly Pro Tyr Asp Arg Asp Ser Trp Asn Pro Val Tyr Gly
180 185 190

Asn Gln Leu Phe Met Lys Thr Arg Asn Gly Ser Met Lys Ala Ala Asp
195 200 205

Asn Phe Leu Asp Pro Asn Lys Ala Ser Ser Leu Leu Ser Ser Gly Phe
210 215 220

Ser Pro Asp Phe Ala Thr Val Ile Thr Met Asp Arg Lys Ala Ser Lys
225 230 235 240

Gln Gln Thr Asn Ile Asp Val Ile Tyr Glu Arg Val Arg Asp Asp Tyr
245 250 255

Gln Leu His Trp Thr Ser Thr Asn Trp Lys Gly Thr Asn Thr Lys Asp
260 265 270

Lys Trp Ile Asp Arg Ser Ser Glu Arg Tyr Lys Ile Asp Trp Glu Lys
275 280 285

Glu Glu Met Thr Asn
290

<210> SEQ ID NO 29
<211> LENGTH: 293
<212> TYPE: PRT
<213> ORGANISM: Artificial Sequence
<220> FEATURE:
<223> OTHER INFORMATION: Mature Hla H35L/G122C/L52C

<400> SEQUENCE: 29

Ala Asp Ser Asp Ile Asn Ile Lys Thr Gly Thr Thr Asp Ile Gly Ser
1 5 10 15

Asn Thr Thr Val Lys Thr Gly Asp Leu Val Thr Tyr Asp Lys Glu Asn
20 25 30

Gly Met Leu Lys Lys Val Phe Tyr Ser Phe Ile Asp Asp Lys Asn His
35 40 45

Asn Lys Lys Cys Leu Val Ile Arg Thr Lys Gly Thr Ile Ala Gly Gln
50 55 60

Tyr Arg Val Tyr Ser Glu Glu Gly Ala Asn Lys Ser Gly Leu Ala Trp
65 70 75 80

Pro Ser Ala Phe Lys Val Gln Leu Gln Leu Pro Asp Asn Glu Val Ala
85 90 95

Gln Ile Ser Asp Tyr Tyr Pro Arg Asn Ser Ile Asp Thr Lys Glu Tyr
100 105 110

Met Ser Thr Leu Thr Tyr Gly Phe Asn Cys Asn Val Thr Gly Asp Asp
115 120 125

Thr Gly Lys Ile Gly Gly Leu Ile Gly Ala Asn Val Ser Ile Gly His
130 135 140

Thr Leu Lys Tyr Val Gln Pro Asp Phe Lys Thr Ile Leu Glu Ser Pro
145 150 155 160

Thr Asp Lys Lys Val Gly Trp Lys Val Ile Phe Asn Asn Met Val Asn
165 170 175

Gln Asn Trp Gly Pro Tyr Asp Arg Asp Ser Trp Asn Pro Val Tyr Gly
180 185 190

Asn Gln Leu Phe Met Lys Thr Arg Asn Gly Ser Met Lys Ala Ala Asp
195 200 205

```
Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Ile Asp Arg Ser Ser Glu Arg Tyr Lys Ile Asp Trp Glu Lys
        275                 280                 285

Glu Glu Met Thr Asn
    290


<210> SEQ ID NO 30
<211> LENGTH: 293
<212> TYPE: PRT
<213> ORGANISM: Artificial Sequence
<220> FEATURE:
<223> OTHER INFORMATION: Mature HlaH35L

<400> SEQUENCE: 30

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met Leu Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270
```

-continued

```
Lys Trp Ile Asp Arg Ser Ser Glu Arg Tyr Lys Ile Asp Trp Glu Lys
        275                 280                 285

Glu Glu Met Thr Asn
    290
```